US007034182B2

(12) United States Patent
Fang et al.

(10) Patent No.: US 7,034,182 B2
(45) Date of Patent: Apr. 25, 2006

(54) COMPOUNDS TO TREAT ALZHEIMER'S DISEASE

(75) Inventors: Lawrence Y. Fang, Foster City, CA (US); Varghese John, San Francisco, CA (US)

(73) Assignee: Elan Pharmaceuticals, Inc., South San Francisco, CA (US)

( * ) Notice: Subject to any disclaimer, the term of this patent is extended or adjusted under 35 U.S.C. 154(b) by 158 days.

(21) Appl. No.: 09/896,874

(22) Filed: Jun. 29, 2001

(65) Prior Publication Data

US 2002/0016320 A1 Feb. 7, 2002

Related U.S. Application Data

(60) Provisional application No. 60/215,323, filed on Jun. 30, 2000.

(51) Int. Cl.
*C07C 243/12* (2006.01)
*A61K 31/16* (2006.01)

(52) U.S. Cl. ........................................ 564/147; 514/614
(58) Field of Classification Search ................ 564/147; 514/614
See application file for complete search history.

(56) References Cited

U.S. PATENT DOCUMENTS

| 4,224,179 A | 9/1980 | Schneider |
| 4,231,877 A | 11/1980 | Yamauchi et al. |
| 4,235,871 A | 11/1980 | Papahadjopoulos et al. |

(Continued)

FOREIGN PATENT DOCUMENTS

| DE | 3610593 A1 | 10/1987 |
| DE | 3721 855 A1 | 9/1988 |
| DE | 40 03 575 A1 | 8/1991 |

(Continued)

OTHER PUBLICATIONS

Chevallier N. et al., Cathepsin D displays in vitro β–secretase–like specificity, Brain Research 750 (1997), pp. 11–19.
Kick E. K. et al., Structure–based design and combinatorial chemistry yield low nanomolar inhibitors of cathepsin D, Chemistry and Biology, Apr. 1997, 4: 297–307.
Ng J.S. et al., A practical synthesis of an HIV protease inhibitor intermediate—Diasteroselective epoxide formation from chiral α–aminoaldehyrds, Tetrahedron vol. 51, No. 23, pp. 6397–6410, 1995.
Copy of PCT International Search Report dated Oct. 17, 2001.
Shugo et al., Chemical and Pharmaceutical Bulletin, vol. 40, No. 2, 1992 XP002178294—Abstract.
Raddatz, J. of Med. Chem., vol. 34, No. 11, 1991, pp. 3267–3280 XP002178295—Abstract.
Nishi et al., Chemistry Letters, 1989, pp. 1993–1996 XP002178296—Abstract.
Harbeson et al., J. of Med. Chem., vol. 32, No. 6, 1989, pp. 1378–1392 XP002178297—Abstract.
Thaisrivongs et al., J. Med. Chem., vol. 31, No. 7, 1988, pp. 1369–1376 XP002178298—Abstract.
Nakano et al., Bulletin of the Chemical Society of Japan, vol. 63, No. 8, 1990, 2224–2232 XP002178299—Abstract.
Kaltenbronn et al., J. Med. Chem., vol. 33, No. 2, 1990, pp. 838–845 XP002178300—Abstract.
Ping et al., J. Med. Chem., vol. 39, No. 10, 1996, pp. 1991–2007 XP002178301—Abstract.
Plummer et al., Bioorganic & Medicinal Chemistry Letters, vol. 9, No. 6, 1999, pp. 835–840 XP002178302—Abstract.
Abbenante, et al., *Biochemical and Biophysical Research Communications*, 2000, 268,pp. 133135 Inhibitors of β–Amyloid Formation Based on theβ–Secretase Cleavage Site [439].
Alterman et al., *J. Med. Chem*, 1998, 41, 37823792 Design and Synthesis of New Potent $C_2$–Symmetric HIV–1 Protease Inhibitors. Use of L–Mannaric Acid asa Peptidomimetic Scaffold [868].
Amblard et al., *J. Med. Chem.*, 1999, 42:20, pp. 4193–4201. Synthesis and Characterization fo Bradykinin $B_2$ Receptor Agonists Containing Constrained Dipeptide Mimics [730].
Arrowsmith et al., *Tetrahedron Letters*, 1987, 28:45, pp. 5569–5572 Amino–Alcohol Dipeptide Analogues: A Simple Synthesis of a Versatile Isotere for the Development of Proteinase Inhibitors [584].
Askin et al., *The Journal of Organic Chemistry*, 1992, 57:10, pp. 2771–2773. Highly Disastrous Alkylations of Chiral Amide Enolates: New Routes to Hydroxyethylene Dipeptide Isostere Inhibitors of HIV–1 Protease [561].
Balicki et al., *Synth. Comm.*, 1993, 23(22), pp. 3149–3155 Mild and Efficient Conversion of Nitriles to Amides with Basic Urea–Hydrogen Peroxide Adduct [874].
Barton, *Protective Groups in Organic Chemistry*, 1976, Chpt. 2, pp. 43–93 Protection of N–H Bonds and $NR_3$ [718].

(Continued)

*Primary Examiner*—Shailendra Kumar
(74) *Attorney, Agent, or Firm*—McDonnell Boehnen Hulbert & Berghoff LLP

(57) ABSTRACT

The present invention is substituted amines of formula (XV)

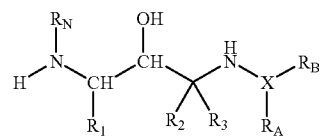

(XV)

useful in treating Alzheimer's disease and other similar diseases.

45 Claims, No Drawings

U.S. PATENT DOCUMENTS

| | | |
|---|---|---|
| 4,247,411 A | 1/1981 | Vanlerberghe et al. |
| 4,394,448 A | 7/1983 | Szoka, Jr. et al. |
| 4,399,216 A | 8/1983 | Axel et al. |
| 4,522,811 A | 6/1985 | Eppstein et al. |
| 4,616,088 A | 10/1986 | Ryono et al. |
| 4,636,491 A | 1/1987 | Bock et al. |
| 4,665,193 A | 5/1987 | Ryono et al. |
| 4,668,770 A | 5/1987 | Boger et al. |
| 4,673,567 A | 6/1987 | Jizomoto |
| 4,676,980 A | 6/1987 | Segal et al. |
| 4,736,866 A | 4/1988 | Leder et al. |
| 4,749,792 A | 6/1988 | Natarajan et al. |
| 4,753,788 A | 6/1988 | Gamble |
| 4,814,270 A | 3/1989 | Piran |
| 4,816,567 A | 3/1989 | Cabilly et al. |
| 4,870,009 A | 9/1989 | Evans et al. |
| 4,880,781 A | 11/1989 | Hester, Jr. et al. |
| 4,897,355 A | 1/1990 | Eppstein et al. |
| 4,935,405 A * | 6/1990 | Hoover et al. ................. 514/19 |
| 5,010,182 A | 4/1991 | Brake et al. |
| 5,142,056 A | 8/1992 | Kempe et al. |
| 5,145,684 A | 9/1992 | Liversidge et al. |
| 5,162,538 A | 11/1992 | Voges et al. |
| 5,175,281 A | 12/1992 | McCall et al. |
| 5,250,565 A | 10/1993 | Brooks et al. |
| 5,364,934 A | 11/1994 | Drayna et al. |
| 5,374,652 A | 12/1994 | Buzzetti et al. |
| 5,376,542 A | 12/1994 | Schlegal |
| 5,387,742 A | 2/1995 | Cordell |
| 5,441,870 A | 8/1995 | Seubert et al. |
| 5,461,067 A | 10/1995 | Norbeck et al. |
| 5,475,138 A | 12/1995 | Pal et al. |
| 5,481,011 A | 1/1996 | Chen et al. |
| 5,482,947 A | 1/1996 | Talley et al. |
| 5,502,061 A | 3/1996 | Hui et al. |
| 5,502,187 A | 3/1996 | Ayer et al. |
| 5,508,294 A | 4/1996 | Vazquez et al. |
| 5,510,349 A | 4/1996 | Talley et al. |
| 5,510,388 A | 4/1996 | Vazquez et al. |
| 5,516,784 A | 5/1996 | Bennett et al. |
| 5,521,219 A | 5/1996 | Vazquez et al. |
| 5,545,640 A | 8/1996 | Beaulieu et al. |
| 5,593,846 A | 1/1997 | Schenk et al. |
| 5,602,169 A | 2/1997 | Hewawasam et al. |
| 5,602,175 A | 2/1997 | Talley et al. |
| 5,604,102 A | 2/1997 | McConlogue et al. |
| 5,610,190 A | 3/1997 | Talley et al. |
| 5,612,486 A | 3/1997 | McConlogue et al. |
| 5,625,031 A | 4/1997 | Webster et al. |
| 5,631,405 A | 5/1997 | Pal et al. |
| 5,639,769 A | 6/1997 | Vazquez et al. |
| 5,648,511 A | 7/1997 | Ng et al. |
| 5,663,200 A | 9/1997 | Bold et al. |
| 5,703,129 A | 12/1997 | Felsenstein et al. |
| 5,708,004 A | 1/1998 | Talley et al. |
| 5,720,936 A | 2/1998 | Wadsworth et al. |
| 5,721,130 A | 2/1998 | Seubert et al. |
| 5,733,882 A | 3/1998 | Carr et al. |
| 5,744,346 A | 4/1998 | Chrysler et al. |
| 5,753,652 A | 5/1998 | Fassler et al. |
| 5,760,064 A | 6/1998 | Vazquez et al. |
| 5,760,076 A | 6/1998 | Vazquez et al. |
| 5,766,846 A | 6/1998 | Schlossmacher et al. |
| 5,807,870 A | 9/1998 | Anderson et al. |
| 5,807,891 A | 9/1998 | Bold et al. |
| 5,811,633 A | 9/1998 | Wadsworth et al. |
| 5,827,891 A | 10/1998 | Dressman et al. |
| 5,830,897 A | 11/1998 | Vazquez et al. |
| 5,831,117 A | 11/1998 | Ng et al. |
| 5,847,169 A | 12/1998 | Nummy et al. |
| 5,849,911 A | 12/1998 | Fassler et al. |
| 5,850,003 A | 12/1998 | McLonlogue et al. |
| 5,863,902 A | 1/1999 | Munoz et al. |
| 5,872,101 A | 2/1999 | Munoz et al. |
| 5,877,015 A | 3/1999 | Hardy et al. |
| 5,877,399 A | 3/1999 | Hsiao et al. |
| 5,886,046 A | 3/1999 | Hirschmann et al. |
| 5,912,410 A | 6/1999 | Cordell |
| 5,922,770 A | 7/1999 | Peschke et al. |
| 5,935,976 A | 8/1999 | Bold et al. |
| 5,942,400 A | 8/1999 | Anderson et al. |
| 5,962,419 A | 10/1999 | McDonald et al. |
| 5,965,588 A | 10/1999 | Vazquez et al. |
| 6,001,813 A | 12/1999 | Gyorkos et al. |
| 6,013,658 A | 1/2000 | Lau et al. |
| 6,022,872 A | 2/2000 | Vazquez et al. |
| 6,045,829 A | 4/2000 | Liversidge et al. |
| 6,051,684 A | 4/2000 | McDonald et al. |
| 6,060,476 A | 5/2000 | Vazquez et al. |
| 6,150,344 A | 11/2000 | Carroll et al. |
| 6,153,652 A | 11/2000 | Wu et al. |
| 6,191,166 B1 | 2/2001 | Audia et al. |
| 6,221,670 B1 | 4/2001 | Cordell et al. |
| 6,225,345 B1 | 5/2001 | Fassler et al. |
| 6,258,806 B1 | 7/2001 | Grobelny |

FOREIGN PATENT DOCUMENTS

| | | |
|---|---|---|
| EP | 0 036776 A2 | 9/1981 |
| EP | 0 073 657 B1 | 3/1983 |
| EP | 0 117 058 B1 | 8/1984 |
| EP | 0 117 060 A2 | 8/1984 |
| EP | 0 173 441 A1 | 5/1986 |
| EP | 0 209 897 A2 | 1/1987 |
| EP | 0 212 903 B1 | 3/1987 |
| EP | 0 264 106 B1 | 4/1988 |
| EP | 0 274 259 A2 | 7/1988 |
| EP | 0 320 205 A2 | 6/1989 |
| EP | 0 337 714 | 10/1989 |
| EP | 0 362 179 A2 | 4/1990 |
| EP | 0 372 537 A2 | 6/1990 |
| EP | 0432694 | 6/1991 |
| EP | 0 437 729 A2 | 7/1991 |
| EP | 0 609 625 A1 | 8/1994 |
| EP | 0 652 009 A1 | 5/1995 |
| GB | 2 203 740 A | 10/1988 |
| GB | 2 211 504 A | 7/1989 |
| JP | 7-126286 | 5/1995 |
| WO | WO 87/02986 | 5/1987 |
| WO | WO 87/04349 | 7/1987 |
| WO | WO 87/05330 | 9/1987 |
| WO | WO 89/00161 | 1/1989 |
| WO | WO 89/01488 | 2/1989 |
| WO | WO 89/05859 | 6/1989 |
| WO | WO 90/13646 | 11/1990 |
| WO | WO 91/00360 | 1/1991 |
| WO | WO 92/00750 | 1/1992 |
| WO | WO 92/17490 | 10/1992 |
| WO | WO 92/20373 | 11/1992 |
| WO | WO 93/02057 | 2/1993 |
| WO | WO 93/08829 | 5/1993 |
| WO | WO 93/17003 | 9/1993 |
| WO | WO 94/04492 | 3/1994 |
| WO | WO 95/06030 | 3/1995 |
| WO | WO 96/22287 | 7/1996 |
| WO | WO 96/35414 | 11/1996 |
| WO | WO 97/30072 | 8/1997 |
| WO | WO 98/22597 | 5/1998 |
| WO | WO 98/29401 | 7/1998 |
| WO | WO 98/33795 | 8/1998 |
| WO | WO 98/38167 | 9/1998 |
| WO | WO 98/50342 | 11/1998 |

| | | |
|---|---|---|
| WO | WO 99 36404 | 7/1999 |
| WO | WO 99/41266 | 8/1999 |
| WO | WO 99/54293 | 10/1999 |
| WO | WO 99/65870 | 12/1999 |
| WO | 9965870 | * 12/1999 |
| WO | WO 00/17369 | 3/2000 |
| WO | WO 00/47618 | 8/2000 |
| WO | WO 00/56335 | 9/2000 |
| WO | WO 00/61748 | 10/2000 |
| WO | WO 00/69262 | 11/2000 |
| WO | WO 00/77030 | 12/2000 |
| WO | WO 01/00663 | 1/2001 |
| WO | WO 01/00665 | 1/2001 |
| WO | WO 01/10387 A2 | 2/2001 |
| WO | WO 01/19797 A2 | 3/2001 |
| WO | WO 01/23533 A2 | 4/2001 |
| WO | WO 01/29563 A1 | 4/2001 |
| WO | WO 01/51659 A2 | 7/2001 |
| WO | WO 02/02505 | 1/2002 |

OTHER PUBLICATIONS

Basu et al., *Tetrahedron Letters*, 1998, 39, pp. 3005–3006 Efficient Transformation of Nitrile into Amide under Mild Condition [881].

Bennett et al., *Synlett*, 1993, 9, pp. 703–704 The Synthesis of Novel HIV–Protease Inhibitors via Silica Gel Asisted Addition of Amines to Epoxides [744].

Berge et al., *Journal of Pharmaceutical Science*, Jan. 1977, 66:1, pp. 1–19 Pharmaceutical Salts [735].

Blatt, *Organic Syntheses*, Collective vol. 2, pp. 312–315 Heptaldoxime [883].

Bodendorf et al., *The Journal of Biological Chemistry*, 2001, 276:15, pp. 12019–12023 A Splice Variant of β–Secretase Deficient in the Amyloidogenic Processing of the Amyloid Precursor Protein [493].

Bose et al., *Synth. Comm.*, 1997, 27(18), pp. 3119–3123 A Facile Hydration of Nitriles by Dimethyldioxirane [ 876].

Calderwood et al, *Tetrahedron Letters*, 1997, 38:7, pp. 1241–1244 Organocerium Reactions of Benzamides and Thiobenzamides: A Direct Synthesis of Tertiary Carbinamines [741].

Chen et al., *Tetrahedron –Mamnaric Acid Letters*, 1997, 38:18, pp. 3175–3178 A Practical Method for the Preparation of α'–Chloroketones of N–Carbamate Protected–α–Aminoacids [885].

Ciganek, *J. Org. Chem.*, 1992, 57:16, pp. 4521–4527 Tertiary Carbinamines by Addition of Organocerium Reagents to Nitriles and Ketimines [721].

Citron et al., *Nature*, 1992, 360:6405, pp. 672–674 Mutation of the β–amyloid Precursor Protein in Familial Alzheimer's Disease Increasesβ–Protein Production [722].

Cushman et al., *J. Med. Chem.*, 1997, 40:15, pp. 2323–2331 Synthesis of Analogs of 2–Methoxyestradiol with Enhanced Inhibitory Effects of Tubulin Polymerization and Cancer Cell Groth [734].

Deno, et al., *J. Am. Chem. Soc.*, 1970, 92:7, pp. 3700–3703 Protonated Cyclopropane Intermediates in the Ractions of Cyclopropanecarboxylic Acids [727].

Diedrich et al., *Tetrahedron Letters*, 1993, 34:39, pp. 6169–6172 Stereoselective Synthesis of A Hydroxyethylene Dipeptide Isostere [559].

Diercks et al., *J. Am. Chem. Soc.*, 1986, 108:11, pp. 3150–3152 Tris(benzocyclobutadieno)benzene, the Triangular [4]Phenylene with a Completely Bond–Fixed Cyclohexatriene Ring: Cobalt–Catalyzed Synthesis from Hexaethynlbenzene and Thermal Ring Opening to 1,2:5,6:9, 10–Tribenzo–3,4,7,8,11,12 hexadehydro[12]–annulene [728].

Dovey et al., *Journal of Neurochemistry*, 2001, 76, pp. 173–181 Functional Gamma–Sec retase Inhibitors Reduce Beta–Amyloid Peptide Levels in Brain 396.

Dragovich et al., *Journal of Medicinal Chemistry*, 1999, 42:7, pp. 1203–1212 Structure–Based Desing, Synthesis, and Biological Evaluation of Irreversible Human Rhinovirus 3C Protease Inhibitors [553].

Emilien, et al., *Neurological Review*,2000, 57, pp. 454–459 Prospects for Pharamcological Intervention in Alzheimer Disease [723].

Felman et al., *J. Med. Chem.* 1992, 35:7, pp. 1183–1190 Synthesis of Antiulcer Activity of Novel 5–(2–Ethenyl Substituted)–3(2H)furanones [724].

Games et al., *Letters to Nature*, Feb. 9, 1995, 373:6514, pp. 523–527 Alzheimer–type Neuropathology in Transgenic Mice Overexpressing V717Fβ–amyloid Precursor Protein [441].

Gao et al., *Tetrahedron Letters*, 1994, 50:4, pp. 979–988 Asymmetric Hetero Diels–Alder Reaction Catalyzed by Stable and Easily Prepared CAB Catalysts [882].

Getman et al., *J. Med. Chem.*, 1993, 36:2, pp. 288–291 Discovery of a Novel Class of Potent HIV–1 Protease Inhibitors Containing the (R)–(Hydroxyethyl)urea Isostere [732].

Ghosh et al., *J. Am. Chem. Soc.*, 2000, 122, pp. 3522–3523 Design of Potent Inhibitors for Human Brain Memapsin 2 β–Secretase). [588].

Ghosh et al, *J. Med. Chem.*, 1993, 36, pp. 2300–2310 Potent HIV Protease Inhibitors: The Development of Tetrahydrofuranylglycines as Novel $IP_3$–Ligands [869].

Gould, *International Journal of* Pharmaceutics, 1986, 33:1–3, pp. 201–217 Salt Selection for Basic Drugs [566].

Greene et al., *Protective Groups in Organic Synthesis: 2nd Ed.*, 1991, Chpt. 7, pp. 309–405 Protection for the Amino Group [747].

Greene, *Protective Groups in Organic Synthesis*, 1981, Chpt. 7, pp. 218–287 Protection for the Amino Group [719].

Hardy, *Nature Genetics*, 1992, 1, pp. 233–234 Framing β–Amyloid [725].

Heck, *Palladium Reagents in Organic Syntheses*, 1985, Chpt. 8.2, pp. 342–365 Carbonylatin of Aromatic Compounds to Acids, Acid Derivatives, Aldehydes and Ketones [870].

Henning, *Organic Synthesis Highlights II*, 1995, pp. 251–259 A. Synthetic Routes to Different Classes of Natural Products and Analogs Thereof—Synthesis of Hydroxyethylene Isoteric Dipeptides [565].

Hon et al., *Heterocycles*, 1990, 31:10, pp. 1745–1750 The Studies of Metal Ion Catalyzed Carbon–Hydrogen Insertion of α–Alkoxy–α'–Diazoketones Derived from Mandelic and Lactic Acids [539].

Hong et al., *Science*, 2000, 290:5489, pp. 150–153 Structure of the Protease Domain of Memapsin 2 (β–Secretase) Complexed with Inhibitor [440].

Hussain et al., *Molecular and Cellular Neuroscience*, 1999, 14, pp. 419–427 Identification of a Novel Aspartic Protease (Asp 2) as β–Secretase [726].

Kabalka et al., *Synth. Comm.*, 1990, 20(10), pp. 1445–1451 The Transformation of Nitriles into Amides [875].

Kaldor et al., *Bioorganic and Medicinal Chemistry Letters*, 1995, 5:7, pp. 721–726 Isophthalic Acid Derivatives: Amino Acid Surrogates for the Inhibition of HIV–1 Protease [587].

Kang et al., *Nature*, 1987, 325:6106, pp. 733–736 The Precursor of Alzheimer's Disease Amyloid A4 Portein Resembles a Cell–Surface Receptor [505].

Kitaguchi et al., *Nature*, Feb. 11, 1988, 331:6156, pp. 530–532 Novel Precursor of Alzheimer's Disease Amyloid Protein Shows Protease Inhibitory Activity [736].

Klumpp et al., *J. Am. Chem. Soc.*, 1979, 101:23 Lithiation of Cyclopropylcarbinols [871].

Lakouraj et al., *Indian Journal of Chemistry*, 1999, 38B, pp. 974–975 Selective Conversion of Nitriles to Amides by Amberlyst A–26 Supported Hydroperoxide [879].

Larock, *Comprehensive Orangic Transformations*, 1986, Chpt 4, pp. 972–985 Carboxylic Acids to Amides [555].

Li et al., *Nature*, 2000, 405, pp. 689–694 Photoactivated V–secretase Inhibitors Directed to the Active Site Covalently Label Presenilin 1 [24].

Li et al, *Nature*, 2000, 405:6787, pp. 689694 Photactivated Gamma Secretase Inhibitors Directed to the Active Site Covalently Label Presenilin I. [585].

Lin et al., *PNAS*, 2000, 97:4, pp. 1456–1460 Human Aspartic Protease Memapsin 2 Cleaves theβ–Amyloid Precursor Protein [687].

Luly et al., *Journal of Organic Chemistry*, 1987, 52:8, pp. 1487–1492 A Synthesis of Protected Aminoalkyl Epoxides from Alpha Amino Acids [558].

Luo et al., *Nature Neuroscience*, Mar. 2001, 4:3, pp. 231–232 Mice Deficient in BACE1, the Alzheimer's β–secretase, have Normal Phenotype and Abolishedβ–amyloid Generation [210].

March, *Advanced Organic Chemistry: Reactions, Mechanisms, and Structure*, 3d Ed., pp. 380–381 Aliphatic Nucleophilic Substitution [729].

Martin et al., *Tetrahedron Letters*, 1998, 39, pp. 1517–1520 Application of Almez–Mediated Amidation Reactions to Solution Phase Peptide Synthesis [540].

Mashraqui et al., *J. Am. Chem. Soc.*, 1982, 104, pp. 4461–4465 Cyclophanes. 14. Synthesis, Structure Assignment, and Conformational Properties of [2.2](2,5)Oxazolo– and Thiazolophanes [872].

McLendon et al., *The FASEB Journal*, 2000, 14:15, pp. 2383 2386 Cell–Free Assays for Gamma–Secretase Activity [359].

Miyaura et al., *Chem. Rev.*, 1995, 95, pp. 2457–2483 Palladium–Catalyzed Cross–Coupling Reactions of Organoboron Compounds [720].

Moersch et al., *Synthesis*, 1971, 12, pp. 647–649 The Synthesis of Alpha–Hydroxycarboxylic Acids by Aeration of Lithiated Carboxylic Acids in Tetrahydrofuran Solution [564].

Murahashi et al., *J. Org. Chem.*, 1992, 57:9, pp. 2521–2523 Ruthenium–Catalyzed Hydration of Nitriles and Transformation of δ–Keto Nitriles to Ene–Lactams [877].

Norman et al., *J. Med. Chem.*, 2000, 43, pp. 4288–4312 Structure–Activity Relationships of a Series of Pyrrolo [3,2–d]pyrimidine Derivatives and Related Compounds as Neuropeptide Y5 Receptor Antagonists [867].

Owa et al., *J. Med. Chem.*, 1999, 42, pp. 3789–3799 Discovery of Novel Antitumor Sulfonamides Targeting G1 Phase of the Cell Cycle [866].

Pirttilla et al., *Neuroscience Letter*, 1998, 249, pp. 21–24 Longitudinal Study of Cerebrospinal Fluid Amyloid Proteins and Apolipoprotein E in Patients with Probable Alzheimer's Disease [738].

Reetz et al., *Tetrahedron Letters*, 30:40, pp. 5425–5428 Protective Group Tuning in the Stereoselective Conversion of α–Amino Aldehydes into Aminoalkyl Epoxides [884].

Sabbagh et al., *Alzheimer's Disease Review*, 1997, 3, 1–19 β–Amyloid and Treatment Opportunities for Alzheimer's Disease [589].

Sakurai et al., *Chemical & Pharmaceutical Bulletin*, 1993, 41:8, pp. 1378–1386 Studies of HIV–1 Protease Inhibitors, II, Incorporation of Four Types of Hydroxyethylene Dipeptide Isosteres at the Scissile Site of Substrate Sequences [549].

Sakurai et al., *Tetrahedron Letters*, 1993, 34:10, pp. 5939–5942 A New Synthetic Route for the Gamma–Lactone Precursors of Hydroxyethylene Dipeptide Isosteres [563].

Sebti et al., *Tetrahedron Letters*, 1996, 37:36, pp. 6555–6556 Catalyse Heterogene de L'Hydratation des Nitriles en Amides par le Phosphate Naturel Dope par KF et le Phosphate Trisodique [878].

Selkoe, *Nature*, 1999, 399:6738, pp. A23–A31 Translating Cell Biology into Therapeutic Advances in Alzheimer's Diseasse [541].

Selkoe, *Neuron*, 1991, 6:4, pp. 487–498 The Molecular Pathology of Alzheimer's Disease [742].

Seubert, et al., *Nature*, Sep. 1992, 359:6393, pp. 325–327 Isolation and Quantification of Soluble Alzheimer's β–peptide from Biological Fluids [503].

Shearman et al., *Biochemistry*, 2000, 39, pp. 8698–9704 L–685, 458, an Aspartyl Protease Transition State Mimic, is a Potent Inhibitor of Amyloidβ–Protein Precursor γ–Secretase Activity [394].

Shibata et al., *Tetrahedron Letters*, 1997, 38:4, pp. 619–620 An Expeditious Synthesis of 2R,3S)–3–tertButoxycarbonylamino–1–isobutylamino–4–phenyl–2–butanol, a Key Buidling Block of HIV Protease Inhibitors [583].

Sinha, et al., *Nature*, Dec. 2, 1999, 402:6761, pp. 537540 Purification and Cloning of Amyloid Precursor Proteinβ–secretase from Human Brain [743].

Smith et al., *Advanced Organic Chemistry—Reactions, Mechanisms and Structure*, 2001, 5ed., Chpt. 19, pp. 1552–1554 Reduction of Carboxylic Acids and Esters to Alkanese [919].

Snyder et al., *J. Am. Chem. Soc.*, Jan.–Jun. 1938, pp. 105–111 Organoboron Coimpounds, and the Study of Reaction Mechanisms. Primary Aliphatic Boronic Acids [873].

Thurkauf et al.,*J. Med. Chem.*, 1990, 33, 1452–1458 Synthesis and Anticonvulsant Activity of 1–Phenylcyclohexylamine Analogues [749].

Tucker et al., *J. Med. Chem.*, 1992, 35:14, pp. 2525–2533 A Series of Potent HIV–1 Protease Inhibitors Containing a Hydroxyethyl Secondary Amine Transition State Isostere: Synthesis, Enzyme Inhibition, and Antiviral Activity [731].

Vassar et al., *Science*, Oct. 22, 1999, 286:5440, pp. 735–741 β–Secretase Cleavage of Alzheimer's Amyloid Precursor Protein by the Transmembrane Aspartic Protease BACE [750].

Vazquez et al., *J. of Med. Chem.*, 1995, 38:4, pp. 581–584 Inhibitors of HIV–1 Protease Containing the Novel and Potent ® Hydroxyethyl)sulfonamide Isostere [582].

Wang et al., *Synlett*, Jun. 2000, 6, pp. 902–904 Preparation of α–Chloroketones by the Chloroacetate Claisen Reaction [886].

Werner et al., *Organic Syntheses*, 1973, Collective vol. 5, pp. 273–276 Cyclobutylamine* [752].

Wilgus, et al., *Tetrahedron Letters*, 1995, 36:20, pp. 3469–3472 The Acid–Catalyzed and Uncatalyzed Hydrolysis of Nitriles on Unactivated Alumina [880].

Yan et al., *Nature*, Dec. 1999, 402:6761, pp. 533–537 Membrane–anchored Aspartyl Protease with Alzheimer's Disease β–secretase Activity [753].

U.S. Appl. No. 09/895871, filed Jun. 29, 2001, Fang et al.

U.S. Appl. No. 09/895843, filed Jun 29, 2001, Beck, et al.

U.S. Appl. No. 09/896,139, filed Jun. 29, 2001, Fang et al.

U.S. Appl. No. 10/152,601, filed May 22, 2002, Schostarez et al.

U.S. Appl. No. 10/291,318, filed Nov. 2002, Varghese et al.

\* cited by examiner

SEQUENCE LISTING

<160> NUMBER OF SEQ ID NOS: 9

<210> SEQ ID NO 1
<211> LENGTH: 12
<212> TYPE: PRT
<213> ORGANISM: Artificial Sequence
<220> FEATURE:
<223> OTHER INFORMATION: Synthetic

<400> SEQUENCE: 1

Ser Glu Val Asn Leu Asp Ala Glu Phe Arg Lys Lys
1               5                   10

<210> SEQ ID NO 2
<211> LENGTH: 12
<212> TYPE: PRT
<213> ORGANISM: Artificial Sequence
<220> FEATURE:
<223> OTHER INFORMATION: Synthetic

<400> SEQUENCE: 2

Ser Glu Val Lys Met Asp Ala Glu Phe Arg Lys Lys
1               5                   10

<210> SEQ ID NO 3
<211> LENGTH: 22
<212> TYPE: PRT
<213> ORGANISM: Artificial Sequence
<220> FEATURE:
<223> OTHER INFORMATION: Synthetic

<400> SEQUENCE: 3

Gly Leu Asn Ile Lys Thr Glu Glu Ile Ser Glu Ile Ser Tyr Glu Val
1               5                   10                  15

Glu Phe Arg Cys Lys Lys
            20

<210> SEQ ID NO 4
<211> LENGTH: 32
<212> TYPE: PRT
<213> ORGANISM: Artificial Sequence
<220> FEATURE:
<223> OTHER INFORMATION: Synthetic

<400> SEQUENCE: 4

Ala Asp Arg Gly Leu Thr Thr Arg Pro Gly Ser Gly Leu Thr Asn Ile
1               5                   10                  15

Lys Thr Glu Glu Ile Ser Glu Val Asn Leu Asp Ala Glu Phe Lys Lys
            20                  25                  30

<210> SEQ ID NO 5
<211> LENGTH: 32
<212> TYPE: PRT
<213> ORGANISM: Artificial Sequence
<220> FEATURE:
<223> OTHER INFORMATION: Synthetic

<400> SEQUENCE: 5

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Ala Lys Lys
            20                  25                  30

-continued

```
<210> SEQ ID NO 6
<211> LENGTH: 33
<212> TYPE: PRT
<213> ORGANISM: Artificial Sequence
<220> FEATURE:
<223> OTHER INFORMATION: Synthetic

<400> SEQUENCE: 6

Cys Gly Gly Ala Asp Arg Gly Leu Thr Thr Arg Pro Gly Ser Gly Leu
1               5                   10                  15

Thr Asn Ile Lys Thr Glu Glu Ile Ser Glu Val Asn Leu Asp Ala Glu
            20                  25                  30

Phe

<210> SEQ ID NO 7
<211> LENGTH: 29
<212> TYPE: PRT
<213> ORGANISM: Artificial Sequence
<220> FEATURE:
<223> OTHER INFORMATION: Synthetic

<400> SEQUENCE: 7

Cys Gly Gly Ala Asp Arg Gly Leu Thr Thr Arg Pro Gly Ser Gly Leu
1               5                   10                  15

Thr Asn Ile Lys Thr Glu Glu Ile Ser Glu Val Asn Leu
            20                  25

<210> SEQ ID NO 8
<211> LENGTH: 9
<212> TYPE: PRT
<213> ORGANISM: Artificial Sequence
<220> FEATURE:
<223> OTHER INFORMATION: Synthetic

<400> SEQUENCE: 8

Ser Glu Val Asn Leu Asp Ala Glu Phe
1               5

<210> SEQ ID NO 9
<211> LENGTH: 30
<212> TYPE: PRT
<213> ORGANISM: Artificial Sequence
<220> FEATURE:
<223> OTHER INFORMATION: Synthetic

<400> SEQUENCE: 9

Ala Asp Arg Gly Leu Thr Thr Arg Pro Gly Ser Gly Leu Thr Asn Ile
1               5                   10                  15

Lys Thr Glu Glu Ile Ser Glu Val Asn Leu Asp Ala Glu Phe
            20                  25                  30
```

COMPOUNDS TO TREAT ALZHEIMER'S DISEASE

CROSS-REFERENCE TO RELATED APPLICATIONS

This application claims priority to the following provisional applications: U.S. provisional application Serial No. 60/215,323, filed Jun. 30, 2000.

BACKGROUND OF THE INVENTION

1. Field of the Invention

The present invention is directed to compounds useful in treatment of Alzheimer's disease and similar diseases.

2. Description of the Related Art

Alzheimer's disease (AD) is a progressive degenerative disease of the brain primarily associated with aging. Clinical presentation of AD is characterized by loss of memory, cognition, reasoning, judgment, and orientation. As the disease progresses, motor, sensory, and linguistic abilities are also affected until there is global impairment of multiple cognitive functions. These cognitive losses occur gradually, but typically lead to severe impairment and eventual death in the range of four to twelve years.

Alzheimer's disease is characterized by two major pathologic observations in the brain: neurofibrillary tangles and beta amyloid (or neuritic) plaques, comprised predominantly of an aggregate of a peptide fragment know as A beta. Individuals with AD exhibit characteristic beta-amyloid deposits in the brain (beta amyloid plaques) and in cerebral blood vessels (beta amyloid angiopathy) as well as neurofibrillary tangles. Neurofibrillary tangles occur not only in Alzheimer's disease but also in other dementia-inducing disorders. On autopsy, large numbers of these lesions are generally found in areas of the human brain important for memory and cognition.

Smaller numbers of these lesions in a more restricted anatomical distribution are found in the brains of most aged humans who do not have clinical AD. Amyloidogenic plaques and vascular amyloid angiopathy also characterize the brains of individuals with Trisomy 21 (Down's Syndrome), Hereditary Cerebral Hemorrhage with Amyloidosis of the Dutch-Type (HCHWA-D), and other neurogenerative disorders. Beta-amyloid is a defining feature of AD, now believed to be a causative precursor or factor in the development of disease. Deposition of A beta in areas of the brain responsible for cognitive activities is a major factor in the development of AD. Beta-amyloid plaques are predominantly composed of amyloid beta peptide (A beta, also sometimes designated betaA4). A beta peptide is derived by proteolysis of the amyloid precursor protein (APP) and is comprised of 39–42 amino acids. Several proteases called secretases are involved in the processing of APP.

Cleavage of APP at the N-terminus of the A beta peptide by beta-secretase and at the C-terminus by one or more gamma-secretases constitutes the beta-amyloidogenic pathway, i.e. the pathway by which A beta is formed. Cleavage of APP by alpha-secretase produces alpha-sAPP, a secreted form of APP that does not result in beta-amyloid plaque formation. This alternate pathway precludes the formation of A beta peptide. A description of the proteolytic processing fragments of APP is found, for example, in U.S. Pat. Nos. 5,441,870; 5,721,130; and 5,942,400.

An aspartyl protease has been identified as the enzyme responsible for processing of APP at the beta-secretase cleavage site. The beta-secretase enzyme has been disclosed using varied nomenclature, including BACE, Asp, and Memapsin. See, for example, Sinha et.al., 1999, *Nature* 402:537–554 (p501) and published PCT application WO00/17369.

Several lines of evidence indicate that progressive cerebral deposition of beta-amyloid peptide (A beta) plays a seminal role in the pathogenesis of AD and can precede cognitive symptoms by years or decades. See, for example, Selkoe, 1991, *Neuron* 6:487. Release of A beta from neuronal cells grown in culture and the presence of A beta in cerebrospinal fluid (CSF) of both normal individuals and AD patients has been demonstrated. See, for example, Seubert et al., 1992, *Nature* 359:325–327.

It has been proposed that A beta peptide accumulates as a result of APP processing by beta-secretase, thus inhibition of this enzyme's activity is desirable for the treatment of AD. In vivo processing of APP at the beta-secretase cleavage site is thought to be a rate-limiting step in A beta production, and is thus a therapeutic target for the treatment of AD. See for example, Sabbagh, M., et al., 1997, *Alz. Dis. Rev.* 3, 1–19.

BACE1 knockout mice fail to produce A beta, and present a normal phenotype. When crossed with transgenic mice that overexpress APP, the progeny show reduced amounts of A beta in brain extracts as compared with control animals (Luo et.al., 2001 *Nature Neuroscience* 4:231–232). This evidence further supports the proposal that inhibition of beta-secretase activity and reduction of A beta in the brain provides a therapeutic method for the treatment of AD and other beta amyloid disorders.

Published PCT application WO00/47618 entitled "Beta-Secretase Enzyme Compositions and Methods" identifies the beta-secretase enzyme and methods of its use. This publication also discloses oligopeptide inhibitors that bind the enzyme's active site and are useful in affinity column purification of the enzyme. In addition, WO00/77030 discloses tetrapeptide inhibitors of beta-secretase activity that are based on a statine molecule.

Various pharmaceutical agents have been proposed for the treatment of Alzheimer's disease but without any real success. U.S. Pat. No. 5,175,281 discloses 21-aminosteroids as being useful for treating Alzheimer's disease. U.S. Pat. No. 5,502,187 discloses bicyclic heterocyclic amines as being useful for treating Alzheimer's disease.

U.S. Pat. Nos. 4,616,088 and 4,665,193 discloses hydroxyethylamine compounds as anti-hypertensive agents due to their ability to inhibit renin.

U.S. Pat. No. 4,636,491 discloses various tetrapeptides which are useful as renin inhibitors.

U.S. Pat. No. 4,749,792 discloses amino compounds useful as analgesics because of their ability to inhibit an enkephalin-degrading aminopeptidase.

U.S. Pat. No. 5,142,056 discloses peptide derivatives with a $C_2$-symmetric dihydroxyethylene core as retroviral protease inhibitors.

U.S. Pat. Nos. 5,461,067 and 5,753,652 disclose the synthesis of retroviral protease inhibitors.

U.S. Pat. Nos. 5,475,138 and 5,631,405 disclose processes and various intermediates useful in the synthesis of selected protease inhibitors.

U.S. Pat. No. 5,502,061 discloses HIV protease inhibitors containing an unsaturated carbocycle or heterocycle at the C-terminus.

U.S. Pat. No. 5,545,640 discloses compounds which inhibit HIV protease activity.

U.S. Pat. No. 5,516,784 discloses compounds active against retroviruses, including HIV.

U.S. Pat. No. 5,602,175 discloses hydroxyethylamine compounds as retroviral protease inhibitors.

U.S. Pat. No. 5,631,405 discloses a process for the formation of intermediates useful in the synthesis of selected protease inhibitors.

U.S. Pat. No. 5,733,882 and International Publications WO 93/02057 and WO 93/17003 disclose dipeptide analogs as retroviral protease inhibitors.

U.S. Pat. No. 5,760,076 discloses hydroxyethylamino sulfonamide compounds as retrovirus protease inhibitors.

U.S. Pat. No. 5,807,870 discloses hydroxyethylamine compounds for the inhibition of HIV protease.

U.S. Pat. No. 5,827,891 discloses HIV protease inhibitors.

U.S. Pat. No. 5,830,897 discloses hydroxyethylamino sulfonamide compounds as retrovirus protease inhibitors.

U.S. Pat. No. 5,831,117 discloses a process and intermediates useful in retroviral protease inhibitor intermediates.

U.S. Pat. No. 5,847,169 discloses a process for preparing aminoepoxides involving the activation of the terminal hydroxyl of an aminodiol.

U.S. Pat. No. 5,849,911 discloses hydroxyethylamine HIV protease inhibitors which form hydrazines with one of the amino groups; this amino group must also be alkylated.

U.S. Pat. No. 5,922,770 discloses peptide derivatives which are useful in treating disorders resulting from a deficiency in growth hormone.

U.S. Pat. No. 6,013,658 discloses peptide derivatives which are useful in treating disorders resulting from a deficiency in growth hormone.

U.S. Pat. No. 6,022,872 discloses hydroxyethylamino sulfonyl urea compounds as HIV protease inhibitors.

U.S. Pat. No. 6,060,476 discloses hydroxyethylamino sulfonamide compounds as HIV protease inhibitors.

International Publication WO 89/01488 discloses renin inhibiting peptides with a hydroxyethylene or dihydroxyethylene isostere in the 10,11-position of the renin substrate angiotensinogen.

International Publication WO92/00750 discloses retroviral protease inhibitors.

International Publication WO 94/04492 discloses hydroxyethylamine intermediates useful for the treatment of retroviral diseases such as HIV. This disclosure also presents epoxides as intermediates for the retroviral inhibitors.

International Publication WO 95/06030 discloses epoxides, chloromethyl ketones, and alcohols prepared as intermediates for HIV protease inhibitors, with a single protecting group on the amine and arylalkyl side chain substituted with alkyl, nitro, nitrile, alkoxy, and thioalkoxy; a preferred side chain is 4-fluorophenylmethyl.

International publication WO98/29401 discloses a method for the preparation of aminoepoxides from aminoaldehydes by which the aminoaldehyde continuously flows into a mixing zone containing an in situ generated halomethyl organometallic reagent.

International Publication WO98/33795 discloses non-peptide inhibitors of cathepsin D.

International Publication WO98/50342 discloses bis aminomethyl carbonyl compounds as inhibitors of cysteine and serine proteases.

International Publication WO00/056335 discloses non-peptide inhibitors of aspartyl proteases. These compounds influence processing of the amyloid precursor protein APP.

EP 0 609 625 discloses HIV protease inhibitors with only one noncyclized nitrogen atom.

Bioorganic & Medicinal Chemistry Letters, 5, 721–726 (1995) describes the synthesis of compounds useful for the inhibition of HIV protease in which the C-terminal nitrogen of the hydroxyethylamine compound is incorporated into a ring system such that a piperidine ring, with a amide substituent next to the nitrogen, is formed.

The hydroxyethylamine "nucleus" or isostere, which is present in the compounds of the present invention has been employed with success in the area of HIV protease inhibition. Many of these hydroxyethylamine compounds are known as well as how to make them. See for example, J. Am. Chem. Soc., 93, 288–291 (1993), Tetrahedron Letters, 28(45) 5569–5572 (1987), J. Med. Chem., 38(4), 581–584 (1994), Tetrahedron Letters, 38(4), 619–620 (1997).

U.S. Pat. No. 5,648,511 discloses a diprotected aralkyl epoxide.

U.S. Pat. Nos. 5,482,947, 5,508,294, 5,510,349, 5,510,388, 5,521,219, 5,610,190, 5,639,769, 5,760,064 and 5,965,588 disclose monoprotected (substituted) aralkyl epoxides.

Tetrahedron Lett., 30(40),5425–5428 (1989) discloses a process in which doubly protected alpha-amino aldehydes are transformed into the corresponding aminoalkyl epoxides.

J. Med. Chem., 36, 2300 (1993) discloses an azide substituted benzyl epoxide.

Tetrahedron Lett., 38, 3175 (1997) discloses a process for the preparation of N-BOC protected epoxides from protected amino acid esters.

J. Med. Chem., 35, 2525 (1992) discloses hydroxyethylamine inhibitors of HIV protease.

U.S. Pat. No. 5,481,011 discloses arylalkyl amino epoxides in which the amino group is protected by a carbamate functionality.

Synlett, 6, 902 (2000) discloses the preparation of alpha-chloroketones of aminoprotected-(substituted)benzyl esters.

U.S. Pat. No. 5,648,511 discloses a diprotected aralkyl alcohol.

U.S. Pat. Nos. 5,482,947, 5,508,294, 5,510,349, 5,510,388, 5,521,219, 5,610,190, 5,639,769, 5,760,064 and 5,965,588 disclose monoprotected (substituted) aralklyl alcohols.

U.S. Pat. Nos. 5,482,947, 5,508,294, 5,510,349, 5,510,388, 5,521,219, 5,610,190, 5,639,769, 5,760,064 and 5,965,588 disclose a process for removing the protecting group of the monoprotected (substituted) aralklyl alcohols to give the free amino alcohol product as the amine salt.

U.S. Pat. No. 5,648,511 discloses the removal of the amino protecting group of a protected amino-alcohol to give a free amino-alcohol.

U.S. Pat. No. 6,150,344 discloses phosphate containing compounds useful in treating Alzheimer's disease.

EP 652 009 A1 discloses inhibitors of aspartyl protease which inhibit beta-amyloid peptide production in cell culture and in vivo. The compounds which inhibit intracellular beta-amyloid peptide production are useful in treating Alzheimer's Disease.

WO00/69262 discloses a new beta-secretase and its use in assays to screen for potential drug candidates against Alzheimer's disease.

WO01/00663 discloses memapsin 2 (human beta-secretase) as well as catalytically active recombinant enzyme. In addition, a method of identifying inhibitors of memapsin 2, as well as two inhibitors are disclosed. Both inhibitors that are disclosed are peptides.

WO01/00665 discloses inhibitors of memapsin 2 that are useful in treating Alzheimer's disease.

WO01/19797 discloses lactams of the formula —C—C—CO—N-lactam-W—X—Y—Z which are useful in treating Alzheimer's disease.

EP 98/14450 and *J. Med. Chem.*, 41(18), 3387–3401 (1998) disclose aza analogs of HIV inhibitors.

At present there are no effective treatments for halting, preventing, or reversing the progression of Alzheimer's disease. Therefore, there is an urgent need for pharmaceutical agents capable of slowing the progression of Alzheimer's disease and/or preventing it in the first place.

Compounds that are effective inhibitors of beta-secretase, that inhibit beta-secretase-mediated cleavage of APP, that are effective inhibitors of A beta production, and/or are effective to reduce amyloid beta deposits or plaques, are needed for the treatment and prevention of disease characterized by amyloid beta deposits or plaques, such as AD.

SUMMARY OF THE INVENTION

Disclosed is a substituted amine of formula (XV)

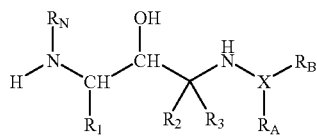

(XV)

where $R_1$ is:
(I) $C_1$–$C_6$ alkyl, optionally substituted with one, two or three substituents selected from the group consisting of $C_1$–$C_3$ alkyl, $C_1$–$C_7$ alkyl (optionally substituted with $C_1$–$C_3$ alkyl and $C_1$–$C_3$ alkoxy), —F, —Cl, —Br, —I, —OH, —SH, —C≡N, —CF$_3$, $C_1$–$C_3$ alkoxy, —NR$_{1-a}$R$_{1-b}$ where R$_{1-a}$ and R$_{1-b}$ are —H or $C_1$–$C_6$ alkyl, and —OC=O NR$_{1-a}$R$_{1-b}$ where R$_{1-a}$ and R$_{1-b}$ are as defined above,
(II) —CH$_2$—S(O)$_{0-2}$—($C_1$–$C_6$ alkyl),
(III) —CH$_2$—CH$_2$—S(O)$_{0-2}$—($C_1$–$C_6$ alkyl),
(IV) $C_2$–$C_6$ alkenyl with one or two double bonds, optionally substituted with one, two or three substituents selected from the group consisting of —F, —Cl, —OH, —SH, —C≡N, —CF$_3$, $C_1$–$C_3$ alkoxy, and —NR$_{1-a}$R$_{1-b}$ where R$_{1-a}$ and R$_{1-b}$ are —H or $C_1$–$C_6$ alkyl,
(V) $C_2$–$C_6$ alkynyl with one or two triple bonds, optionally substituted with one, two or three substituents selected from the group consisting of —F, —Cl, —OH, —SH, —C≡N, —CF$_3$, $C_1$–$C_3$ alkoxy, and —NR$_{1-a}$R$_{1-b}$ where R$_{1-a}$ and R$_{1-b}$ are —H or $C_1$–$C_6$ alkyl,
(VI) —(CH$_2$)$_{n1}$—(R$_{1-aryl}$) where n$_1$ is zero or one and where R$_{1-aryl}$ is phenyl, 1-naphthyl, 2-naphthyl and indanyl, indenyl, dihydronaphthalyl, or tetralinyl optionally substituted with one, two, three or four of the following substituents on the aryl ring:
  (A) $C_1$–$C_6$ alkyl optionally substituted with one, two or three substituents selected from the group consisting of $C_1$–$C_3$ alkyl, —F, —Cl, —Br, —I, —OH, —SH, —C≡N, —CF$_3$, and $C_1$–$C_3$ alkoxy, and —NR$_{1-a}$R$_{1-b}$ where R$_{1-a}$ and R$_{1-b}$ are as defined above,
  (B) $C_2$–$C_6$ alkenyl with one or two double bonds, optionally substituted with one, two or three substituents selected from the group consisting of —F, —Cl, —OH, —SH, —C≡N, —CF$_3$, $C_1$–$C_3$ alkoxy, and —NR$_{1-a}$R$_{1-b}$ where R$_{1-a}$ and R$_{1-b}$ are —H or $C_1$–$C_6$ alkyl,
  (C) $C_2$–$C_6$ alkynyl with one or two triple bonds, optionally substituted with one, two or three substituents selected from the group consisting of —F, —Cl, —OH, —SH, —C≡N, —CF$_3$, $C_1$–$C_3$ alkoxy, and NR$_{1-a}$R$_{1-b}$ where R$_{1-a}$ and R$_{1-b}$ are —H or $C_1$–$C_6$ alkyl,
  (D) —F, Cl, —Br or —I,
  (F) —$C_1$–$C_6$ alkoxy optionally substituted with one, two or three of —F,
  (G) —NR$_{N-2}$R$_{N-3}$ where R$_{N-2}$ and R$_{N-3}$ are as defined below,
  (H) —OH,
  (I) —C≡N,
  (J) $C_3$–$C_7$ cycloalkyl, optionally substituted with one, two or three substituents selected from the group consisting of —F, —Cl, —OH, —SH, —C≡N, —CF$_3$, $C_1$–$C_3$ alkoxy, and —NR$_{1-a}$R$_{1-b}$ where R$_{1-a}$ and R$_{1-b}$ are —H or $C_1$–$C_6$ alkyl,
  (K) —CO—($C_1$–$C_4$ alkyl),
  (L) —SO$_2$—NR$_{1-a}$R$_{1-b}$ where R$_{1-a}$ and R$_{1-b}$ are as defined above,
  (M) —CO—NR$_{1-a}$R$_{1-b}$ where R$_{1-a}$ and R$_{1-b}$ are as defined above, or
  (N) —SO$_2$—($C_1$–$C_4$ alkyl),
(VII) —(CH$_2$)$_{n1}$-(R$_{1-heteroaryl}$) where n$_1$ is as defined above and where R$_{1-heteroaryl}$ is selected from the group consisting of:
  pyridinyl,
  pyrimidinyl,
  quinolinyl,
  benzothienyl,
  indolyl,
  indolinyl,
  pryidazinyl,
  pyrazinyl,
  isoquinolyl,
  quinazolinyl,
  quinoxalinyl,
  phthalazinyl,
  imidazolyl,
  isoxazolyl,
  pyrazolyl,
  oxazolyl,
  thiazolyl,
  indolizinyl,
  indazolyl,
  benzothiazolyl,
  benzimidazolyl,
  benzofuranyl,
  furanyl,
  thienyl,
  pyrrolyl,
  oxadiazolyl,
  thiadiazolyl,
  triazolyl,
  tetrazolyl,
  oxazolopyridinyl,
  imidazopyridinyl,
  isothiazolyl,
  naphthyridinyl,
  cinnolinyl,
  carbazolyl,
  beta-carbolinyl,
  isochromanyl,
  chromanyl,
  tetrahydroisoquinolinyl,
  isoindolinyl, isobenzotetrahydrofuranyl,
isobenzotetrahydrothienyl,
isobenzothienyl,
benzoxazolyl,
pyridopyridinyl,
benzotetrahydrofiuranyl,
benzotetrahydrothienyl,
purinyl,
benzodioxolyl,
triazinyl,
phenoxazinyl,
phenothiazinyl,
pteridinyl,
benzothiazolyl,
imidazopyridinyl,
niidazothiazolyl,
dihydrobenzisoxazinyl,
benzisoxazinyl,
benzoxazinyl,
dihydrobenzisothiazinyl,
benzopyranyl,
benzothiopyranyl,
coumarinyl,
isocoumarinyl,
chromonyl,
chromanonyl,
pyridinyl-N-oxide,
tetrahydroquinolinyl
dihydroquinolinyl
dihydroquinolinonyl
dihydroisoquinolinonyl
dihydrocoumarinyl
dihydroisocoumarinyl
isoindolinonyl
benzodioxanyl
benzoxazolinonyl
pyrrolyl N-oxide,
pyrimidinyl N-oxide,
pyridazinyl N-oxide,
pyrazinyl N-oxide,
quinolinyl N-oxide,
indolyl N-oxide,
indolinyl N-oxide,
isoquinolyl N-oxide,
quinazolinyl N-oxide,
quinoxalinyl N-oxide,
phthalazinyl N-oxide,
imidazolyl N-oxide,
isoxazolyl N-oxide,
oxazolyl N-oxide,
thiazolyl N-oxide,
indolizinyl N-oxide,
indazolyl N-oxide,
benzothiazolyl N-oxide,
benzimnidazolyl N-oxide,
pyrrolyl N-oxide,
oxadiazolyl N-oxide,
thiadiazolyl N-oxide,
triazolyl N-oxide,
tetrazolyl N-oxide,
benzothiopyranyl S-oxide, and
benzothiopyranyl S,S-dioxide,
where the $R_{1\text{-}heteroaryl}$ group is bonded to —$(CH_2)_{n1}$— by any ring atom of the parent $R_{1\text{-}heteroaryl}$ group substituted by hydrogen such that the new bond to the $R_{1\text{-}heteroaryl}$ group replaces the hydrogen atom and its bond, where heteroaryl is optionally substituted with one, two, three or four of:

(1) $C_1$–$C_6$ alkyl optionally substituted with one, two or three substituents selected from the group consisting of $C_1$–$C_3$ alkyl, —F, —Cl, —Br, —I, —OH, —SH, —C≡N, —$CF_3$, $C_1$–$C_3$ alkoxy, and —$NR_{1\text{-}a}R_{1\text{-}b}$ where $R_{1\text{-}a}$ and $R_{1\text{-}b}$ are as defined above,
(2) $C_2$–$C_6$ alkenyl with one or two double bonds, optionally substituted with one, two or three substituents selected from the group consisting of —F, —Cl, —OH, —SH, —C≡N, —$CF_3$, $C_1$–$C_3$ alkoxy, and —$NR_{1\text{-}a}R_{1\text{-}b}$ where $R_{1\text{-}a}$ and $R_{1\text{-}b}$ are —H or $C_1$–$C_6$ alkyl,
(3) $C_2$–$C_6$ alkynyl with one or two triple bonds, optionally substituted with one, two or three substituents selected from the group consisting of —F, —Cl, —OH, —SH, —C≡N, —$CF_3$, $C_1$–$C_3$ alkoxy, and —$NR_{1\text{-}a}R_{1\text{-}b}$ where $R_{1\text{-}a}$ and $R_{1\text{-}b}$ are —H or $C_1$–$C_6$ alkyl,
(4) —F, Cl, —Br or —I,
(6) —$C_1$–$C_6$ alkoxy optionally substituted with one, two, or three of —F,
(7) —$NR_{N\text{-}2}R_{N\text{-}3}$ where $R_{N\text{-}2}$ and $R_{N\text{-}3}$ are as defined below,
(8) —OH,
(9) —C≡N,
(10) $C_3$–$C_7$ cycloalkyl, optionally substituted with one, two or three substituents selected from the group consisting of —F, —Cl, —OH, —SH, —C≡N, —$CF_3$, $C_1$–$C_3$ alkoxy, and —$NR_{1\text{-}a}R_{1\text{-}b}$ where $R_{1\text{-}a}$ and $R_{1\text{-}b}$ are —H or $C_1$–$C_6$ alkyl,
(11) —CO—($C_1$–$C_4$ alkyl),
(12) —$SO_2$—$NR_{1\text{-}a}R_{1\text{-}b}$ where $R_{1\text{-}a}$ and $R_{1\text{-}b}$ are as defined above,
(13) —CO—$NR_{1\text{-}a}R_{1\text{-}b}$ where $R_{1\text{-}a}$ and $R_{1\text{-}b}$ are as defined above, or
(14) —$SO_2$—($C_1$–$C_4$ alkyl), with the proviso that when $n_1$ is zero $R_{1\text{-}heteroaryl}$ is not bonded to the carbon chain by nitrogen; or (VIII) —$(CH_2)_{n1}$—$(R_{1\text{-}heterocycle})$ where $n_1$ is as defined above and $R_{1\text{-}heterocycle}$ is selected from the group consisting of:
morpholinyl,
thiomorpholinyl,
thiomorpholinyl S-oxide,
thiomorpholinyl S,S-dioxide,
piperazinyl,
homopiperazinyl,
pyrrolidinyl,
pyrrolinyl,
tetrahydropyranyl,
piperidinyl,
tetrahydrofuranyl,
tetrahydrothienyl,
homopiperidinyl,
homomorpholinyl,
homothiomorpholinyl,
homothiomorpholinyl S,S-dioxide,
oxazolidinonyl,
dihydropyrazolyl,
dihydropyrrolyl,
dihydropyrazinyl,
dihydropyridinyl,
dihydropyrimidinyl,
dihydrofuryl,
dihydropyranyl,
tetrahydrothienyl S-oxide, tetrahydrothienyl S,S-dioxide, and
homothiomorpholinyl S-oxide,
where the $R_{1\text{-}heterocycle}$ group is bonded by any atom of the parent $R_{1\text{-}heterocycle}$ group substituted by hydrogen such that the new bond to the $R_{1\text{-}heterocycle}$ group replaces the hydrogen atom and its bond, where heterocycle is optionally substituted with one, two, three or four:
- (1) $C_1$–$C_6$ alkyl optionally substituted with one, two or three substituents selected from the group consisting of $C_1$–$C_3$ alkyl, —F, —Cl, —Br, —I, —OH, —SH, —C≡N, —CF$_3$, $C_1$–$C_3$ alkoxy, and —NR$_{1\text{-}a}$R$_{1\text{-}b}$ where $R_{1\text{-}a}$ and $R_{1\text{-}b}$ are as defined above,
- (2) $C_2$–$C_6$ alkenyl with one or two double bonds, optionally substituted with one, two or three substituents selected from the group consisting of —F, —Cl, —OH, —SH, —C≡N, —CF$_3$, $C_1$–$C_3$ alkoxy, and —NR$_{1\text{-}a}$R$_{1\text{-}b}$ where $R_{1\text{-}a}$ and $R_{1\text{-}b}$ are $C_1$–$C_6$ alkyl,
- (3) $C_2$–$C_6$ alkynyl with one or two triple bonds, optionally substituted with one, two or three substituents selected from the group consisting of —F, —Cl, —OH, —SH, —C≡N, —CF$_3$, $C_1$–$C_3$ alkoxy, and —NR$_{1\text{-}a}$R$_{1\text{-}b}$ where $R_{1\text{-}a}$ and $R_{1\text{-}b}$ are —H or $C_1$–$C_6$ alkyl,
- (4) —F, Cl, —Br or —I,
- (5) $C_1$–$C_6$ alkoxy,
- (6) —$C_1$–$C_6$ alkoxy optionally substituted with one, two, or three —F,
- (7) —NR$_{N\text{-}2}$R$_{N\text{-}3}$ where $R_{N\text{-}2}$ and $R_{N\text{-}3}$ are as defined below,
- (8) —OH,
- (9) —C≡N,
- (10) $C_3$–$C_7$ cycloalkyl, optionally substituted with one, two or three substituents selected from the group consisting of —F, —Cl, —OH, —SH, —C≡N, —CF$_3$, $C_1$–$C_3$ alkoxy, and —NR$_{1\text{-}a}$R$_{1\text{-}b}$ where $R_{1\text{-}a}$ and $R_{1\text{-}b}$ are —H or $C_1$–$C_6$ alkyl,
- (11) —CO—($C_1$–$C_4$ alkyl),
- (12) —SO$_2$—NR$_{1\text{-}a}$R$_{1\text{-}b}$ where $R_{1\text{-}a}$ and $R_{1\text{-}b}$ are as defined above,
- (13) —CO—NR$_{1\text{-}a}$R$_{1\text{-}b}$ where $R_{1\text{-}a}$ and $R_{1\text{-}b}$ are as defined above,
- (14) —SO$_2$—($C_1$–$C_4$ alkyl), or
- (15) =O, with the proviso that when $n_1$ is zero $R_{1\text{-}heterocycle}$ is not bonded to the carbon chain by nitrogen;

where $R_2$ is:
- (I) —H,
- (II) $C_1$–$C_6$ alkyl, optionally substituted with one, two or three substituents selected from the group consisting of $C_1$–$C_3$ alkyl, —F, —Cl, —Br, —I, —OH, —SH, —C≡N, —CF$_3$, $C_1$–$C_3$ alkoxy, and —NR$_{1\text{-}a}$R$_{1\text{-}b}$ where $R_{1\text{-}a}$ and $R_{1\text{-}b}$ are as defined above,
- (III) —(CH$_2$)$_{0\text{-}4}$—R$_{2\text{-}1}$ where $R_{2\text{-}1}$ is $R_{1\text{-}aryl}$ or $R_{1\text{-}heteroaryl}$ where $R_{1\text{-}aryl}$ and $R_{1\text{-}heteroaryl}$ are as defined above;
- (IV) $C_2$–$C_6$ alkenyl with one or two double bonds, optionally substituted with one, two or three substituents selected from the group consisting of —F, —Cl, —OH, —SH, —C≡N, —CF$_3$, $C_1$–$C_3$ alkoxy, and —NR$_{1\text{-}a}$R$_{1\text{-}b}$ where $R_{1\text{-}a}$ and $R_{1\text{-}b}$ are —H or $C_1$–$C_6$ alkyl,
- (V) $C_2$–$C_6$ alkynyl with one or two triple bonds, optionally substituted with one, two or three substituents selected from the group consisting of —F, —Cl, —OH, —SH, —C≡N, —CF$_3$, $C_1$–$C_3$ alkoxy, and —NR$_{1\text{-}a}$R$_{1\text{-}b}$ where $R_{1\text{-}a}$ and $R_{1\text{-}b}$ are —H or $C_1$–$C_6$ alkyl, or
- (VI) —(CH$_2$)$_{0\text{-}4}$—$C_3$–$C_7$ cycloalkyl, optionally substituted with one, two or three substituents selected from the group consisting of —F, —Cl, —OH, —SH, —C≡N, —CF$_3$, $C_1$–$C_3$ alkoxy, and —NR$_{1\text{-}a}$R$_{1\text{-}b}$ where $R_{1\text{-}a}$ and $R_{1\text{-}b}$ are —H or $C_1$–$C_6$ alkyl;

where $R_3$ is selected from the group consisting of:
- (I) —H,
- (II) $C_1$–$C_6$ alkyl, optionally substituted with one, two or three substituents selected from the group consisting of $C_1$–$C_3$ alkyl, —F, —Cl, —Br, —I, —OH, —SH, —C≡N, —CF$_3$, $C_1$–$C_3$ alkoxy, and —NR$_{1\text{-}a}$R$_{1\text{-}b}$ where $R_{1\text{-}a}$ and $R_{1\text{-}b}$ are as defined above,
- (III) —(CH$_2$)$_{0\text{-}4}$—R$_{2\text{-}1}$ where $R_{2\text{-}1}$ is $R_{1\text{-}aryl}$ or $R_{1\text{-}heteroaryl}$ where $R_{1\text{-}aryl}$ and $R_{1\text{-}heteroaryl}$ are as defined above,
- (IV) $C_2$–$C_6$ alkenyl with one or two double bonds,
- (V) $C_2$–$C_6$ alkynyl with one or two triple bonds; or
- (VI) —(CH$_2$)$_{0\text{-}4}$—$C_3$–$C_7$ cycloalkyl, optionally substituted with one, two or three substituents selected from the group consisting of —F, —Cl, —OH, —SH, —C≡N, —CF$_3$, $C_1$–$C_3$ alkoxy, and —NR$_{1\text{-}a}$R$_{1\text{-}b}$ where $R_{1\text{-}1}$ and $R_{1\text{-}b}$ are —H or $C_1$–$C_6$ alkyl,
- and where $R_2$ and $R_3$ are taken together with the carbon to which they are attached to form a carbocycle of three, four, five, six, or seven carbon atoms, optionally where one carbon atom is replaced by a heteroatom selected from the group consisting of —O—, —S—, —SO$_2$—, and —NR$_{N\text{-}2}$—, where $R_{N\text{-}2}$ is as defined below;

where $R_N$ is:
- (I) $R_{N\text{-}1}$—$X_N$— where $X_N$ is selected from the group consisting of:
  - (A) —CO—,
  - (B) —SO$_2$—,
  - (C) —(CR'R'')$_{1\text{-}6}$ where R' and R'' are the same or different and are —H and $C_1$–$C_4$ alkyl,
  - (D) —CO—(CR'R'')$_{1\text{-}6}$—$X_{N\text{-}1}$ where $X_{N\text{-}1}$ is selected from the group consisting of —O—, —S— and —NR'— and where R' and R'' are as defined above, and
  - (E) a single bond;

where $R_{N\text{-}1}$ is selected from the group consisting of:
- (A) $R_{N\text{-}aryl}$ where $R_{N\text{-}aryl}$ is phenyl, 1-naphthyl, 2-naphthyl, tetralinyl, indanyl, 6,7,8,9-tetrahydro-5H-benzo[a]cycloheptenyl, or dihydronaphthyl optionally substituted with one, two or three of the following substituents which can be the same or different and are:
  - (1) $C_1$–$C_6$ alkyl, optionally substituted with one, two or three substituents selected from the group consisting of $C_1$–$C_3$ alkyl, —F, —Cl, —Br, —I, —OH, —SH, —C≡N, —CF$_3$, $C_1$–$C_3$ alkoxy, and —NR$_{1\text{-}a}$R$_{1\text{-}b}$ where $R_{1\text{-}a}$ and $R_{1\text{-}b}$ are as defined above,
  - (2) —OH,
  - (3) —NO$_2$,
  - (4) —F, —Cl, —Br, —I,
  - (5) —CO—OH,
  - (6) —C≡N,
  - (7) —(CH$_2$)$_{0\text{-}4}$—CO—NR$_{N\text{-}2}$R$_{N\text{-}3}$ where $R_{N\text{-}2}$ and $R_{N\text{-}3}$ are the same or different and are selected from the group consisting of:
    - (a) —H,
    - (b) —$C_1$–$C_6$ alkyl optionally substituted with one substitutent selected from the group consisting of:

(i) —OH, and
(ii) —NH$_2$,
(c) —C$_1$–C$_6$ alkyl optionally substituted with one, two, or three —F, —Cl, —Br, or —I,
(d) —C$_3$–C$_7$ cycloalkyl,
(e) —(C$_1$–C$_2$ alkyl)-(C$_3$–C$_7$ cycloalkyl),
(f) —(C$_1$–C$_6$ alkyl)-O—(C$_1$–C$_3$ alkyl),
(g) —C$_2$–C$_6$ alkenyl with one or two double bonds,
(h) —C$_2$–C$_6$ alkynyl with one or two triple bonds,
(i) —C$_1$–C$_6$ alkyl chain with one double bond and one triple bond,
(j) —R$_{1\text{-}aryl}$ where R$_{1\text{-}aryl}$ is as defined above, and
(k) —R$_{1\text{-}heteroaryl}$ where R$_{1\text{-}heteroaryl}$ is as defined above,
(8) —(CH$_2$)$_{0\text{-}4}$—CO—(C$_1$–C$_{12}$ alkyl),
(9) —(CH$_2$)$_{0\text{-}4}$—CO—(C$_2$–C$_{12}$ alkenyl with one, two or three double bonds),
(10) —(CH$_2$)$_{0\text{-}4}$—CO—(C$_2$–C$_{12}$ alkynyl with one, two or three triple bonds),
(11) —(CH$_2$)$_{0\text{-}4}$—CO—(C$_3$–C$_7$ cycloalkyl),
(12) —(CH$_2$)$_{0\text{-}4}$—CO—R$_{1\text{-}aryl}$ where R$_{1\text{-}aryl}$ is as defined above,
(13) —(CH$_2$)$_{0\text{-}4}$—CO—R$_{1\text{-}heteroaryl}$ where R$_{1\text{-}heteroaryl}$ is as defined above,
(14) —(CH$_2$)$_{0\text{-}4}$—CO—R$_{1\text{-}heterocycle}$ where R$_{1\text{-}heterocycle}$ is as defined above,
(15) —(CH$_2$)$_{0\text{-}4}$—CO—R$_{N\text{-}4}$ where R$_{N\text{-}4}$ is selected from the group consisting of morpholinyl, thiomorpholinyl, piperazinyl, piperidinyl, homomorpholinyl, homothiomorpholinyl, homothiomorpholinyl S-oxide, homothiomorpholinyl S,S-dioxide, pyrrolinyl and pyrrolidinyl where each group is optionally substituted with one, two, three, or four of C$_1$–C$_6$ alkyl,
(16) —CH$_2$)$_{0\text{-}4}$—CO—O—R$_{N\text{-}5}$ where R$_{N\text{-}5}$ is selected from the group consisting of:
(a) C$_1$–C$_6$ alkyl,
(b) —(CH$_2$)$_{0\text{-}2}$—(R$_{1\text{-}aryl}$) where R$_{1\text{-}aryl}$ is as defined above,
(c) C$_2$–C$_6$ alkenyl containing one or two double bonds,
(d) C$_2$–C$_6$ alkynyl containing one or two triple bonds,
(e) C$_3$–C$_7$ cycloalkyl, and
(f) —(CH$_2$)$_{0\text{-}2}$—(R$_{1\text{-}heteroaryl}$) where R$_{1\text{-}heteroaryl}$ is as defined above,
(17) —(CH$_2$)$_{0\text{-}4}$—SO$_2$—NR$_{N\text{-}2}$R$_{N\text{-}3}$ where R$_{N\text{-}2}$ and R$_{N\text{-}3}$ are as defined above,
(18) —(CH$_2$)$_{0\text{-}4}$—SO—(C$_1$–C$_8$ alkyl),
(19) —(CH$_2$)$_{0\text{-}4}$—SO$_2$—(C$_1$–C$_{12}$ alkyl),
(20) —(CH$_2$)$_{0\text{-}4}$—SO$_2$—(C$_3$–C$_7$ cycloalkyl),
(21) —(CH$_2$)$_{0\text{-}4}$—N(H or R$_{N\text{-}5}$)—CO—O—R$_{N\text{-}5}$ where R$_{N\text{-}5}$ can be the same or different and is as defined above,
(22) —(CH$_2$)$_{0\text{-}4}$—N(H or R$_{N\text{-}5}$)—CO—N(R$_{N\text{-}5}$)$_2$, where R$_{N\text{-}5}$ can be the same or different and is as defined above,
(23) —(CH$_2$)$_{0\text{-}4}$—N—CS—N(R$_{N\text{-}5}$)$_2$, where R$_{N\text{-}5}$ can be the same or different and is as defined above,
(24) —(CH$_2$)$_{0\text{-}4}$—N(—H or R$_{N\text{-}5}$)—CO—R$_{N\text{-}2}$ where R$_{N\text{-}5}$ and R$_{N\text{-}2}$ can be the same or different and are as defined above,
(25) —(CH$_2$)$_{0\text{-}4}$—NR$_{N\text{-}2}$R$_{N\text{-}3}$ where R$_{N\text{-}2}$ and R$_{N\text{-}3}$ can be the same or different and are as defined above,
(26) —(CH$_2$)$_{0\text{-}4}$—R$_{N\text{-}4}$ where R$_{N\text{-}4}$ is as defined above,
(27) —(CH$_2$)$_{0\text{-}4}$—O—CO—(C$_1$–C$_6$ alkyl),
(28) —(CH$_2$)$_{0\text{-}4}$—O—P(O)—(OR$_{N\text{-}aryl\text{-}1}$)$_2$ where R$_{N\text{-}aryl\text{-}1}$ is —H or C$_1$–C$_4$ alkyl,
(29) —(CH$_2$)$_{0\text{-}4}$—O—CO—N(R$_{N\text{-}5}$)$_2$ where R$_{N\text{-}5}$ is as defined above,
(30) —(CH$_2$)$_{0\text{-}4}$—O—CS—N(R$_{N\text{-}5}$)$_2$ where R$_{N\text{-}5}$ is as defined above,
(31) —(CH$_2$)$_{0\text{-}4}$—O—(R$_{N\text{-}5}$)$_2$ where R$_{N\text{-}5}$ is as defined above,
(32) —(CH$_2$)$_{0\text{-}4}$—O—(R$_{N\text{-}5}$)$_2$—COOH where R$_{N\text{-}5}$ is as defined above,
(33) —(CH$_2$)$_{0\text{-}4}$—S—(R$_{N\text{-}5}$)$_2$ where R$_{N\text{-}5}$ is as defined above,
(34) —(CH$_2$)$_{0\text{-}4}$—O—(C$_1$–C$_6$ alkyl optionally substituted with one, two, three, four, or five of —F),
(35) C$_3$–C$_7$ cycloalkyl,
(36) C$_2$–C$_6$ alkenyl with one or two double bonds optionally substituted with C$_1$–C$_3$ alkyl, —F, —Cl, —Br, —I, —OH, —SH, —C≡N, —CF$_3$, C$_1$–C$_3$ alkoxy, or —NR$_{1\text{-}a}$R$_{1\text{-}b}$ where R$_{1\text{-}a}$ and R$_{1\text{-}b}$ are as defined above,
(37) C$_2$–C$_6$ alkynyl with one or two triple bonds optionally substituted with C$_1$–C$_3$ alkyl, —F, —Cl, —Br, —I, —OH, —SH, —C≡N, —CF$_3$, C$_1$–C$_3$ alkoxy, or —NR$_{1\text{-}a}$R$_{1\text{-}b}$ where R$_{1\text{-}a}$ and R$_{1\text{-}b}$ are as defined above,
(38) —(CH$_2$)$_{0\text{-}4}$—N(—H or R$_{N\text{-}5}$)—SO$_2$—R$_{N\text{-}2}$ where R$_{N\text{-}5}$ and R$_{N\text{-}2}$ can be the same of different and are as described above, or
(39) —(CH$_2$)$_{0\text{-}4}$—C$_3$–C$_7$ cycloalkyl,
(B) —R$_{N\text{-}heteroryl}$ where R$_{N\text{-}heteroaryl}$ is selected from the group consisting of:
pyridinyl,
pyrimidinyl,
quinolinyl,
benzothienyl,
indolyl,
indolinyl,
pryidazinyl,
pyrazinyl,
isoindolyl,
isoquinolyl,
quinazolinyl,
quinoxalinyl,
phthalazinyl,
imidazolyl,
isoxazolyl,
pyrazolyl,
oxazolyl,
thiazolyl,
indolizinyl,
indazolyl,
benzothiazolyl,
benzimidazolyl,
benzofuranyl,
furanyl,
thienyl,
pyrrolyl,
oxadiazolyl,
thiadiazolyl,
triazolyl,
tetrazolyl,
oxazolopyridinyl,
imidazopyridinyl,
isothiazolyl, naphthyridinyl,
cinnolinyl,
carbazolyl,
beta-carbolinyl,
isochromanyl,
chromanyl,
tetrahydroisoquinolinyl,
isoindolinyl,
isobenzotetrahydrofuranyl,
isobenzotetrahydrothienyl,
isobenzothienyl,
benzoxazolyl,
pyridopyridinyl,
benzotetrahydrofuranyl,
benzotetrahydrothienyl,
purinyl,
benzodioxolyl,
triazinyl,
phenoxazinyl,
phenothiazinyl,
pteridinyl,
benzothiazolyl,
imidazopyridinyl,
imidazothiazolyl,
dihydrobenzisoxazinyl,
benzisoxazinyl,
benzoxazinyl,
dihydrobenzisothiazinyl,
benzopyranyl,
benzothiopyranyl,
coumarinyl,
isocoumarinyl,
chromonyl,
chromanonyl,
pyridinyl-N-oxide,
tetrahydroquinolinyl,
dihydroquinolinyl,
dihydroquinolinonyl,
dihydroisoquinolinonyl,
dihydrocoumarinyl,
dihydroisocoumarinyl,
isoindolinonyl,
benzodioxanyl,
benzoxazolinonyl,
pyrrolyl N-oxide,
pyrimidinyl N-oxide,
pyridazinyl N-oxide,
pyrazinyl N-oxide,
quinolinyl N-oxide,
indolyl N-oxide,
indolinyl N-oxide,
isoquinolyl N-oxide,
quinazolinyl N-oxide,
quinoxalinyl N-oxide,
phthalazinyl N-oxide,
imidazolyl N-oxide,
isoxazolyl N-oxide,
oxazolyl N-oxide,
thiazolyl N-oxide,
indolizinyl N-oxide,
indazolyl N-oxide,
benzothiazolyl N-oxide,
benzimidazolyl N-oxide,
pyrrolyl N-oxide,
oxadiazolyl N-oxide,
thiadiazolyl N-oxide,
triazolyl N-oxide,
tetrazolyl N-oxide,
benzothiopyranyl S-oxide, and
benzothiopyranyl S,S-dioxide where the $R_{N\text{-}heteroaryl}$ group is bonded by any atom of the parent $R_{N\text{-}heteroaryl}$ group substituted by hydrogen such that the new bond to the $R_{N\text{-}heteroaryl}$ group replaces the hydrogen atom and its bond, where heteroaryl is optionally substituted with one, two, three, or four of:

(1) $C_1$–$C_6$ alkyl, optionally substituted with one, two or three substituents selected from the group consisting of $C_1$–$C_3$ alkyl, —F, —Cl, —Br, —I, —OH, —SH, —C≡N, —CF$_3$, $C_1$–$C_3$ alkoxy, and —NR$_{1\text{-}a}$R$_{1\text{-}b}$ where R$_{1\text{-}a}$ and R$_{1\text{-}b}$ are as defined above, (2) —OH, (3) —NO$_2$, (4) —F, —Cl, —Br, or —I, (5) —CO—OH, (6) —C≡N, (7) —(CH$_2$)$_{0\text{-}4}$—CO—NR$_{N\text{-}2}$R$_{N\text{-}3}$ where R$_{N\text{-}2}$ and R$_{N\text{-}3}$ are the same or different and are selected from the group consisting of:
  (a) —H,
  (b) —C$_1$–C$_6$ alkyl optionally substituted with one substitutent selected from the group consisting of:
    (i) —OH, and
    (ii) —NH$_2$,
  (c) —C$_1$–C$_6$ alkyl optionally substituted with one, two, or three —F, —Cl, —Br, —I,
  (d) —C$_3$–C$_7$ cycloalkyl,
  (e) —(C$_1$–C$_2$ alkyl)-(C$_3$–C$_7$ cycloalkyl),
  (f) —(C$_1$–C$_6$ alkyl)-O—(C$_1$–C$_3$ alkyl),
  (g) —C$_2$–C$_6$ alkenyl with one or two double bonds,
  (h) —C$_2$–C$_6$ alkynyl with one or two triple bonds,
  (i) —C$_1$–C$_6$ alkyl chain with one double bond and one triple bond,
  (j) —R$_{1\text{-}aryl}$ where R$_{1\text{-}aryl}$ is as defined above,
  (k) —R$_{1\text{-}heteroaryl}$ where R$_{1\text{-}heteroaryl}$ is as defined above, (8) —(CH$_2$)$_{0\text{-}4}$—CO—(C$_1$–C$_{12}$ alkyl), (9) —(CH$_2$)$_{0\text{-}4}$—CO—(C$_2$–C$_{12}$ alkenyl with one, two or three double bonds),

(10) —(CH$_2$)$_{0\text{-}4}$—CO—(C$_2$–C$_{12}$ alkynyl with one, two or three triple bonds),

(11) —(CH$_2$)$_{0\text{-}4}$—CO—(C$_3$–C$_7$ cycloalkyl),

(12) —(CH$_2$)$_{0\text{-}4}$—CO—R$_{1\text{-}aryl}$ where R$_{1\text{-}aryl}$ is as defined above,

(13) —(CH$_2$)$_{0\text{-}4}$—CO—R$_{1\text{-}heteroaryl}$ where R$_{1\text{-}heteroaryl}$ is as defined above,

(14) —(CH$_2$)$_{0\text{-}4}$—CO—R$_{1\text{-}heterocycle}$ where R$_{1\text{-}heterocycle}$ is as defined above,

(15) —(CH$_2$)$_{0\text{-}4}$—CO—R$_{N\text{-}4}$ where R$_{N\text{-}4}$ is selected from the group consisting of morpholinyl, thiomorpholinyl, piperazinyl, piperidinyl, homomorpholinyl, homothiomorpholinyl, homothiomorpholinyl S-oxide, homothiomorpholinyl S,S-dioxide, pyrrolinyl and pyrrolidinyl where each group is optionally substituted with one, two, three, or four of C$_1$–C$_6$ alkyl,

(16) —(CH$_2$)$_{0\text{-}4}$—CO—O—R$_{N\text{-}5}$ where R$_{N\text{-}5}$ is selected from the group consisting of:
  (a) C$_1$–C$_6$ alkyl,
  (b) —(CH$_2$)$_{0\text{-}2}$—(R$_{1\text{-}aryl}$) where R$_{1\text{-}aryl}$ is as defined above, (c) $C_2$–$C_6$ alkenyl containing one or two double bonds,
(d) $C_2$–$C_6$ alkynyl containing one or two triple bonds,
(e) $C_3$–$C_7$ cycloalkyl, and
(f) —$(CH_2)_{0-2}$—($R_{1\text{-}heteroaryl}$) where $R_{1\text{-}heteroaryl}$ is as defined above,
(17) —$(CH_2)_{0-4}$—$SO_2$—$NR_{N\text{-}2}R_{N\text{-}3}$ where $R_{N\text{-}2}$ and $R_{N\text{-}3}$ are as defined above,
(18) —$(CH_2)_{0-4}$—SO—($C_1$–$C_8$ alkyl),
(19) —$(CH_2)_{0-4}$—$SO_2$—($C_1$–$C_{12}$ alkyl),
(20) —$(CH_2)_{0-4}$—$SO_2$—($C_3$–$C_7$ cycloalkyl),
(21) —$(CH_2)_{0-4}$—N(H or $R_{N\text{-}5}$)—CO—O—$R_{N\text{-}5}$ where $R_{N\text{-}5}$ can be the same or different and is as defined above,
(22) —$(CH_2)_{0-4}$—N(H or $R_{N\text{-}5}$)—CO—N($R_{N\text{-}5}$)$_2$, where $R_{N\text{-}5}$ can be the same or different and is as defined above,
(23) —$(CH_2)_{0-4}$—N—CS—N($R_{N\text{-}5}$)$_2$, where $R_{N\text{-}5}$ can be the same or different and is as defined above,
(24) —$(CH_2)_{0-4}$—N(—H or $R_{N\text{-}5}$)—CO—$R_{N\text{-}2}$ where $R_{N\text{-}5}$ and $R_{N\text{-}2}$ can be the same or different and are as defined above,
(25) —$(CH_2)_{0-4}$—$NR_{N\text{-}2}R_{N\text{-}3}$ where $R_{N\text{-}2}$ and $R_{N\text{-}3}$ can be the same or different and are as defined above,
(26) —$(CH_2)_{0-4}$—$R_{N\text{-}4}$ where $R_{N\text{-}4}$ is as defined above,
(27) —$(CH_2)_{0-4}$—O—CO—($C_1$–$C_6$ alkyl),
(28) —$(CH_2)_{0-4}$—O—P(O)—($OR_{N\text{-}aryl\text{-}1}$)$_2$ where $R_{N\text{-}aryl\text{-}1}$ is —H or $C_1$–$C_4$ alkyl,
(29) —$(CH_2)_{0-4}$—O—CO—N($R_{N\text{-}5}$)$_2$ where $R_{N\text{-}5}$ is as defined above,
(30) —$(CH_2)_{0-4}$—O—CS—N($R_{N\text{-}5}$)$_2$ where $R_{N\text{-}5}$ is as defined above,
(31) —$(CH_2)_{0-4}$—O—($R_{N\text{-}5}$)$_2$ where $R_{N\text{-}5}$ is as defined above,
(32) —$(CH_2)_{0-4}$—O—($R_{N\text{-}5}$)$_2$—COOH where $R_{N\text{-}5}$ is as defined above,
(33) —$(CH_2)_{0-4}$—S—($R_{N\text{-}5}$)$_2$ where $R_{N\text{-}5}$ is as defined above,
(34) —$(CH_2)_{0-4}$O—($C_1$–$C_6$ alkyl optionally substituted with one, two, three, four, or five of —F),
(35) $C_3$–$C_7$ cycloalkyl,
(36) $C_2$–$C_6$ alkenyl with one or two double bonds optionally substituted with $C_1$–$C_3$ alkyl, —F, —Cl, —Br, —I, —OH, —SH, —C≡N, —$CF_3$, $C_1$–$C_3$ alkoxy, or —$NR_{1\text{-}a}R_{1\text{-}b}$ where $R_{1\text{-}a}$ and $R_{1\text{-}b}$ are as defined above,
(37) $C_2$–$C_6$ alkynyl with one or two triple bonds optionally substituted with $C_1$–$C_3$ alkyl, —F, —Cl, —Br, -I, -OH, -SH, —C≡N, —$CF_3$, $C_1$–$C_3$ alkoxy, or —$NR_{1\text{-}a}R_{1\text{-}b}$ where $R_{1\text{-}a}$ and $R_{1\text{-}b}$ are as defined above,
(38) —$(CH_2)_{0-4}$—N(—H or $R_{N\text{-}5}$)—$SO_2$-$R_{N\text{-}2}$ where $R_{N\text{-}5}$ and $R_{N\text{-}2}$ can be the same of different and are as defined above, or
(39) —$(CH_2)_{0-4}$—$C_3$–$C_7$ cycloalkyl,
(C) $R_{N\text{-}aryl}$—W—$R_{N\text{-}aryl}$, where $R_{N\text{-}aryl}$, and $R_{N\text{-}aryl}$ are as defined above,
(D) $R_{N\text{-}aryl}$—W—$R_{N\text{-}heteroaryl}$, where $R_{N\text{-}aryl}$, and $R_{N\text{-}heteroaryl}$, are as defined above,
(E) $R_{N\text{-}aryl}$—W—$R_{N\text{-}1\text{-}heterocycle}$, wherein $R_{N\text{-}1\text{-}heterocycle}$ is the same as $R_{1\text{-}heterocycle}$, and $R_{1\text{-}heterocycle}$, and $R_{1\text{-}heteroaryl}$ is as defined above
(F) $R_{N\text{-}heteroaryl}$—W—$R_{N\text{-}aryl}$, where $R_{N\text{-}aryl}$, and $R_{N\text{-}heteroaryl}$, are as defined above,
(G) $R_{N\text{-}heteroaryl}$—W—$R_{N\text{-}heteroaryl}$, where $R_{N\text{-}heteroaryl}$ is as defined above,
(H) $R_{N\text{-}heteroaryl}$—W—$R_{N\text{-}1\text{-}heterocycle}$, where $R_{N\text{-}heteroaryl}$, and $R_{N\text{-}1\text{-}heterocycle}$, are as defined above,
(I) $R_{N\text{-}heterocycle}$—W—$R_{N\text{-}aryl}$, wherein $R_{N\text{-}heterocycle}$ is the same as $R_{1\text{-}heterocycle}$, and $R_{1\text{-}heterocycle}$ is as defined above, and $R_{N\text{-}aryl}$ is as defined above,
(J) $R_{N\text{-}heterocycle}$—W—$R_{N\text{-}heteroaryl}$, where $R_{N\text{-}heteroaryl}$, and $R_{N\text{-}heterocycle}$, are as defined above, and
(K) $R_{N\text{-}heterocycle}$—W—$R_{N\text{-}1\text{-}heterocycle}$, where $R_{N\text{-}heterocycycle}$, and $R_{N\text{-}1\text{-}heterocycycle}$, are as defined above,
where W is
(1) —$(CH_2)_{0-4}$,
(2) —O—,
(3) —$S(O)_{0-2}$—,
(4) —N($R_{N\text{-}5}$)— where $R_{N\text{-}5}$ is as defined above, or
(5) —CO—;
(II) —CO—($C_1$–$C_{10}$ alkyl) where alkyl is optionally substituted with one three substitutents selected from the group consisting of:
(A) —OH,
(B) —$C_1$–$C_6$ alkoxy,
(C) —$C_1$–$C_6$ thioalkoxy,
(D) —CO—O—$R_{N\text{-}8}$ where $R_{N\text{-}8}$ is —H, $C_1$–$C_6$ alkyl or -phenyl,
(E) —CO—$NR_{N\text{-}2}R_{N\text{-}3}$ where $R_{N\text{-}2}$ and $R_{N\text{-}3}$ are the same or different and are as defined above,
(F) —CO—$R_{N\text{-}4}$ where $R_{N\text{-}4}$ is as defined above,
(G) —$SO_2$—($C_1$–$C_8$ alkyl),
(H) —$SO_2$—$NR_{N\text{-}2}R_{N\text{-}3}$ where $R_{N\text{-}2}$ and $R_{N\text{-}3}$ are the same or different and are as defined above,
(I) —NH—CO—($C_1$–$C_6$ alkyl),
(J) —NH—CO—O—$R_{N\text{-}8}$ where $R_{N\text{-}8}$ is as defined above,
(K) —$NR_{N\text{-}2}R_{N\text{-}3}$ where $R_{N\text{-}2}$ and $R_{N\text{-}3}$ are the same or different and are as defined above,
(L) —$R_{N\text{-}4}$ where $R_{N\text{-}4}$ is as defined above,
(M) —O—CO—($C_1$–$C_6$ alkyl),
(N) —O—CO—$NR_{N\text{-}8}R_{N\text{-}8}$ where $R_{N\text{-}8}$ are the same or different and are as defined above,
(O) —O—($C_1$–$C_5$ alkyl)-COOH,
(P) —O—($C_1$–$C_6$ alkyl optionally substitued with one, two, or three of —F, —Cl, —Br, —I),
(Q) —NH—$SO_2$—($C_1$–$C_6$ alkyl), and
(R) —F, or —Cl,
(III) —CO—($C_1$–$C_6$ alkyl)-O—($C_1$–$C_6$ alkyl) where alkyl is optionally substituted with one, two, or three of substitutents selected from the group consisting of:
(A) —OH,
(B) —$C_1$–$C_6$ alkoxy,
(C) —$C_1$–$C_6$ thioalkoxy,
(D) —CO—O—$R_{N\text{-}8}$ where $R_{N\text{-}8}$ is —H, $C_1$–$C_6$ alkyl or -phenyl,
(E) —CO—$NR_{N\text{-}2}R_{N\text{-}3}$ where $R_{N\text{-}2}$ and $R_{N\text{-}3}$ are the same or different and are as defined above,
(F) —CO—$R_{N\text{-}4}$ where $R_{N\text{-}4}$ is as defined above,
(G) —$SO_2$—($C_1$–$C_8$alkyl),
(H) —$SO_2$—$NR_{N\text{-}2}R_{N\text{-}3}$ where $R_{N\text{-}2}$ and $R_{N\text{-}3}$ are the same or different and are as defined above,
(I) —NH—CO—($C_1$–$C_6$ alkyl),
(J) —NH—CO—O—$R_{N\text{-}8}$ where $R_{N\text{-}8}$ is as defined above,
(K) —$NR_{N\text{-}2}R_{N\text{-}3}$ where $R_{N\text{-}2}$ and $R_{N\text{-}3}$ are the same or different and are as defined above, (L) —$R_{N-4}$ where $R_{N-4}$ is as defined above,
(M) —O—CO—($C_1$–$C_6$ alkyl),
(N) —O—CO—$NR_{N-8}R_{N-8}$ where $R_{N-8}$ are the same or different and are as defined above,
(O) —O—($C_1$–$C_5$ alkyl)-COOH,
(P) —O—($C_1$–$C_6$ alkyl optionally substituted with one, two, or three of —F, —Cl, —Br, or —I),
(Q) —NH—$SO_2$—($C_1$–$C_6$ alkyl), and
(R) —F, or —Cl,
(IV) —CO—($C_1$–$C_6$ alkyl)-S—($C_1$–$C_6$ alkyl) where alkyl is optionally substituted with one, two, or three of substitutents selected from the group consisting of:
(A) —OH,
(B) —$C_1$–$C_6$ alkoxy,
(C) —$C_1$–$C_6$ thioalkoxy,
(D) —CO—O—$R_{N-8}$ where $R_{N-8}$ is as defined above,
(E) —CO—$NR_{N-2}R_{N-3}$ where $R_{N-2}$ and $R_{N-3}$ are the same or different and are as defined above,
(F) —CO—$R_{N-4}$ where $R_{N-4}$ is as defined above,
(G) —$SO_2$—($C_1$–$C_8$ alkyl),
(H) —$SO_2$—$NR_{N-2}R_{N-3}$ where $R_{N-2}$ and $R_{N-3}$ are the same or different and are as defined above,
(I) —NH—CO—($C_1$–$C_6$ alkyl),
(J) —NH—CO—O—$R_{N-8}$ where $R_{N-8}$ is as defined above,
(K) —$NR_{N-2}R_{N-3}$ where $R_{N-2}$ and $R_{N-3}$ are the same or different and are as defined above,
(L) —$R_{N-4}$ where $R_{N-4}$ is as defined above,
(M) —O—CO—($C_1$–$C_6$ alkyl),
(N) —O—CO—$NR_{N-8}R_{N-8}$ where $R_{N-8}$ are the same or different and are as defined above,
(O) —O—($C_1$–$C_5$ alkyl)-COOH,
(P) —O—($C_1$–$C_6$ alkyl optionally substituted with one, two, or three of —F, —Cl, —Br, or —I),
(Q) —NH—$SO_2$—($C_1$–$C_6$ alkyl), and
(R) —F, or —Cl,
(V) —CO—CH(—($CH_2$)$_{0-2}$—O—$R_{N-10}$)—($CH_2$)$_{0-2}$—$R_{N-aryl}/R_{N-heteroaryl}$) where $R_{N-aryl}$ and $R_{N-heteroaryl}$ are as defined above, where $R_{N-10}$ is selected from the group consisting of:
(A) —H,
(B) $C_1$–$C_6$ alkyl,
(C) $C_3$–$C_7$ cycloalkyl,
(D) $C_2$–$C_6$ alkenyl with one double bond,
(E) $C_2$–$C_6$ alkynyl with one triple bond,
(F) $R_{1-aryl}$ where $R_{1-aryl}$ is as defined above, and
(G) $R_{N-heteroaryl}$ where $R_{N-heteroaryl}$ is as defined above, or
(VI) —CO—($C_3$–$C_8$ cycloalkyl) where alkyl is optionally substituted with one or two substitutents selected from the group consisting of:
(A) —($CH_2$)$_{0-4}$—OH,
(B) —($CH_2$)$_{0-4}$—$C_1$–$C_6$ alkoxy,
(C) —($CH_2$)$_{0-4}$—$C_1$–$C_6$ thioalkoxy,
(D) —($CH_2$)$_{0-4}$—CO—O—$R_{N-8}$ where $R_{N-8}$ is —H, $C_1$–$C_6$ alkyl or phenyl,
(E) —($CH_2$)$_{0-4}$—CO—$NR_{N-2}R_{N-3}$ where $R_{N-2}$ and $R_{N-3}$ are the same or different and are as defined above,
(F) —($CH_2$)$_{0-4}$—CO—$R_{N-4}$ where $R_{N-4}$ is as defined above,
(G) —($CH_2$)$_{0-4}$—$SO_2$—($C_1$–$C_8$ alkyl),
(H) —($CH_2$)$_{0-4}$—$SO_2$—$NR_{N-2}R_{N-3}$ where $R_{N-2}$ and $R_{N-3}$ are the same or different and are as defined above,
(I) —($CH_2$)$_{0-4}$—NH—CO—($C_1$–$C_6$ alkyl),
(J) —NH—CO—O—$R_{N-8}$ where $R_{N-8}$ is as defined above,
(K) —($CH_2$)$_{0-4}$—$NR_{N-2}R_{N-3}$ where $R_{N-2}$ and $R_{N-3}$ are the same or different and are as defined above,
(L) —($CH_2$)$_{0-4}$—$R_{N-4}$ where $R_{N-4}$ is as defined above,
(M) —O—CO—($C_1$–$C_6$ alkyl),
(N) —O—CO—$NR_{N-8}R_{N-8}$ where $R_{N-8}$ are the same or different and are as defined above,
(O) —O—($C_1$–$C_5$ alkyl)-COOH,
(P) —O—($C_1$–$C_6$ alkyl optionally substitued with one, two, or three of —F, —Cl, —Br, or —I),
(Q) —NH—$SO_2$—($C_1$–$C_6$ alkyl), and
(R) —F, or —Cl;
where $R_A$ is:
(I) —$C_1$–$C_{10}$ alkyl optionally substituted with one, two or three substituents selected from the group consisting of $C_1$–$C_3$ alkyl, —F, —Cl, —Br, —I, —OH, —SH, —C≡N, —$CF_3$, $C_1$–$C_6$ alkoxy, —O-phenyl, —$NR_{1-b}R_{1-b}$ where $R_{1-b}$ and $R_{1-b}$ are as defined above, —OC=O $NR_{1-a}R_{1-b}$ where $R_{1-a}$ and $R_{1-b}$ are as defined above, —S(=O)$_{0-2}$ $R_{1-a}$ where $R_{1-a}$ is as defined above, —$NR_{1-a}$C=O $NR_{1-a}R_{1-b}$ where $R_{1-a}$ and $R_{1-b}$ are as defined above, —C=O $NR_{1-a}R_{1-b}$ where $R_{1-a}$ and $R_{1-b}$ are as defined above, and —S(=O)$_2$ $NR_{1-a}R_{1-b}$ where $R_{1-a}$ and $R_{1-b}$ are as defined above,
(II) —($CH_2$)$_{0-3}$—($C_3$–$C_8$) cycloalkyl where cycloalkyl can be optionally substituted with one, two or three substituents selected from the group consisting of $C_1$–$C_3$ alkCyl, —F, —Cl, —Br, —I, —OH, —SH, —C≡N, —$CF_3$, $C_1$–$C_6$ alkoxy, —O-phenyl, —CO—OH, —CO—O—($C_1$–$C_4$ alkyl), and —$NR_{1-a}$ $R_{1-b}$ where $R_{1-a}$ and $R_{1-b}$ are as defined above,
(III) —($CR_{A-x}R_{A-y}$)$_{0-4}$—$R_{A-aryl}$ where $R_{A-x}$ and $R_{A-y}$ are
(A) —H,
(B) $C_1$–$C_4$ alkyl optionally substituted with one or two —OH,
(C) $C_1$–$C_4$ alkoxy optionally substituted with one, two, or three of —F,
(D) —($CH_2$)$_{0-4}$—$C_3$–$C_7$ cycloalkyl,
(E) $C_2$–$C_6$ alkenyl containing one or two double bonds,
(F) $C_2$–$C_6$ alklynyl contianing one or two triple bonds, or
(G) phenyl,
and where $R_{A-x}$ and $R_{A-y}$ are taken together with the carbon to which they are attached to form a carbocycle of three, four, five, six or seven carbon atoms, optionally where one carbon atom is replaced by a heteroatom selected from the group consisting of —O—, —S—, —$SO_2$—, and —$NR_{N-2}$— and $R_{A-aryl}$ is the same as $R_{N-aryl}$,
(IV) —($CR_{A-x}R_{A-y}$)$_{0-4}$—$R_{A-heteroaryl}$ where $R_{A-heteroaryl}$ is the same as $R_{N-heteroaryl}$ and $R_{A-x}$ and $R_{A-y}$ are as defined above,
(V) —($CR_{A-x}R_{A-y}$)$_{0-4}$—$R_{A-aryl}$—$R_{A-aryl}$ where $R_{A-aryl}$, $R_{A-x}$ and $R_{A-y}$ are as defined above,
(VI) —($CR_{A-x}R_{A-y}$)$_{0-4}$—$R_{A-aryl}$—$R_{A-heteroaryl}$ where $R_{A-aryl}$, $R_{A-heteroaryl}$, $R_{A-x}$ and $R_{A-y}$ are as defined above,
(VII) —($CR_{A-x}R_{A-y}$)$_{0-4}$—$R_{A-heteroaryl}$—$R_{A-aryl}$ where $R_{A-heteroaryl}$, $R_{A-aryl}$, $R_{A-x}$ and $R_{A-y}$ are as defined above,
(VIII) —($CR_{A-x}R_{A-y}$)$_{0-4}$—$R_{A-heteroaryl}$—$R_{A-heteroaryl}$ where $R_{A-heteroaryl}$, $R_{A-x}$ and $R_{A-y}$ are as defined above, (IX) —$(CR_{A-x}R_{A-y})_{0-4}$—$R_{A-aryl}$—$R_{A-heterocycle}$ where $R_{A-heterocycle}$ is defined as $R_{1-heterocycle}$ is defined as $R_{1-heterocycle}$, and where $R_{A-aryl}$, $R_{A-x}$ and $R_{A-y}$ are as defined above, (X) —$(CR_{A-x}R_{A-y})_{0-4}$—$R_{A-heteroaryl}$—$R_{A-heterocycle}$ where $R_{A-heteroaryl}$, $R_{A-heterocycle}$, $R_{A-x}$ and $R_{A-y}$ are as defined above, (XI) —$CR_{A-x}R_{A-y})_{0-4}$—$R_{A-heterocycle}$—$R_{A-aryl}$ where $R_{A-heterocycle}$, $R_{A-aryl}$, $R_{A-x}$ and $R_{A-y}$ are as defined above, (XII) —$(CR_{A-x}R_{A-y})_{0-4}$—$R_{A-heterocycle}$—$R_{A-heteroaryl}$ where $R_{A-heterocycle}$, $R_{A-heteroaryl}$, $R_{A-x}$ and $R_{A-y}$ are as defined above, (XIII) —$(CR_{A-x}R_{A-y})_{0-4}$—$R_{A-heterocycle}$—$R_{A-heterocycle}$ where $R_{A-heterocycle}$, $R_{Ax}$ and $R_{A-y}$ are as defined above, (XIV) —$(CR_{A-x}R_{A-y})_{0-4}$—$R_{A-heterocycle}$ where $R_{A-heterocycle}$, $R_{A-x}$ and $R_{A-y}$ are as defined above, (XV) —$[C(R_{A-1})(R_{A-2})]_{1-3}$—CO—N—$(R_{A-3})_2$ where $R_{A-1}$ and $R_{A-2}$ are the same or different and are selected from the group consisting of:
  (A) —H,
  (B) —$C_1$–$C_6$ alkyl, optionally substituted with one, two or three substituents selected from the group consisting of $C_1$–$C_3$ alkyl, —F, —Cl, —Br, —I, —OH, —SH, —C≡N, —$CF_3$, $C_1$–$C_6$ alkoxy, —O-phenyl, and —$NR_{1-a}R_{1-b}$ where $R_{1-a}$ and $R_{1-b}$ are as defined above,
  (C) $C_2$–$C_6$ alkenyl with one or two double bonds, optionally substituted with one, two or three substituents selected from the group consisting of $C_1$–$C_3$ alkyl, —F, —Cl, —Br, —I, —OH, —SH, —C≡N, —$CF_3$, $C_1$–$C_6$ alkoxy, —O-phenyl, and —$NR_{1-a}R_{1-b}$ where $R_{1-a}$ and $R_{1-b}$ are as defined above,
  (D) $C_2$–$C_6$ alkynyl with one or two triple bonds, optionally substituted with one, two or three substituents selected from the group consisting of $C_1$–$C_3$ alkyl, —F, —Cl, —Br, —I, —OH, —SH, —C≡N, —$CF_3$, $C_1$–$C_6$ alkoxy, —O-phenyl, and —$NR_{1-a}R_{1-b}$ where $R_{1-a}$ and $R_{1-b}$ are as defined above,
  (E) —$(CH_2)_{1-2}$—$S(O)_{0-2}$—($C_1$–$C_6$ alkyl),
  (F) —$(CH_2)_{0-4}$—$C_3$–$C_7$ cycloalkyl, optionally substituted with one, two or three substituents selected from the group consisting of $C_1$–$C_3$ alkyl, —F, —Cl, —Br, —I, —OH, —SH, —C≡N, —$CF_3$, $C_1$–$C_6$ alkoxy, —O-phenyl, and —$NR_{1-a}R_{1-b}$ where $R_{1-a}$ are as defined above,
  (G) —($C_1$–$C_4$ alkyl)-$R_{A'-aryl}$ where $R_{A'-aryl}$ is as defined for $R_{1-aryl}$,
  (H) —($C_1$–$C_4$ alkyl)-$R_{A-heteroaryl}$ where $R_{A-heteroaryl}$ is as defined above,
  (I) —($C_1$–$C_4$ alkyl)-$R_{A-heterocycle}$ where $R_{A-heterocycle}$ is as defined above,
  (J) —$R_{A-heteroaryl}$ where $R_{A-heteroaryl}$ is as defined above,
  (K) —$R_{A-heterocycle}$ where $R_{A-heterocycle}$ is as defined above,
  (M) —$(CH_2)_{1-4}$—$R_{A-4}$—$(CH_2)_{0-4}$—$R_{A'-aryl}$ where $R_{A-4}$ is —O—, —S— or —$NR_{A-5}$— where $R_{A-5}$ is $C_1$–$C_6$ alkyl, and where $R_{A'-aryl}$ is defined above,
  (N) —$(CH_2)_{1-4}$—$R_{A-4}$—$(CH_2)_{0-4}$—$R_{A-heteroaryl}$ where $R_{A-4}$ and $R_{A-heteroaryl}$ are as defined above, and
  (O) —$R_{A'-aryl}$ where $R_{A'-aryl}$ is as defined above,
and where $R_{A-3}$ is the same or different and is:
  (A) —H,
  (B) —$C_1$–$C_6$ alkyl optionally substituted with one, two or three substituents selected from the group consisting of $C_1$–$C_3$ alkyl, —F, —Cl, —Br, —I, —OH, —SH, —C≡N, —$CF_3$, $C_1$–$C_6$ alkoxy, —O-phenyl, —$NR_{1-a}R_{1-b}$ where $R_{1-a}$ and $R_{1-b}$ are as defined above,
  (C) $C_2$–$C_6$ alkenyl with one or two double bonds, optionally substituted with one, two or three substituents selected from the group consisting of $C_1$–$C_3$ alkyl, —F, —Cl, —Br, —I, —OH, —SH, —C≡N, —$CF_3$, $C_1$–$C_6$ alkoxy, —O-phenyl, and —$NR_{1-a}R_{1-b}$ where $R_{1-a}$ and $R_{1-b}$ are as defined above,
  (D) $C_2$–$C_6$ alkynyl with one or two triple bonds, optionally substituted with one, two or three substituents selected from the group consisting of $C_1$–$C_3$ alkyl, —F, —Cl, —Br, —I, —OH, —SH, —C≡N, —$CF_3$, $C_1$–$C_6$ alkoxy, —O-phenyl, and $NR_{1-a}R_{1-b}$ where $R_{1-a}$ and $R_{1-b}$ are as defined above,
  (E) —$(CH_2)_{0-4}$—$C_3$–$C_7$ cycloalkyl, optionally substituted with one, two or three substituents selected from the group consisting of $C_1$–$C_3$ alkyl, —F, —Cl, —Br, —I, —OH, —SH, —C≡N, —$CF_3$, $C_1$–$C_6$ alkoxy, —O-phenyl, and —$NR_{1-a}R_{1-b}$ where $R_{1-a}$ and $R_{1-b}$ are as defined above,
  (F) —$R_{A'-aryl}$ where $R_{A'-aryl}$ is as defined above,
  (G) —$R_{A-heteroaryl}$ where $R_{A-heteroaryl}$ is as defined above,
  (H) —$R_{A-heterocycle}$ where $R_{A-heterocycle}$ is as defined above,
  (I) —($C_1$–$C_4$ alkyl)-$R_{A'-aryl}$ where $R_{A'-aryl}$ is as defined above,
  (J) —($C_1$–$C_4$ alkyl)-$R_{A-heteroaryl}$ where $R_{A-heteroaryl}$ is as defined above,
  (K) —($C_1$–$C_4$ alkyl)-$R_{A-heterocycle}$ where $R_{A-heterocycle}$ is as defined above, or (XVI) —$CH(R_{A-aryl})_2$ where $R_{A-aryl}$ are the same or different and are as defined above, (XVII) —$CH(R_{A-heteroaryl})_2$ where $R_{A-heteroaryl}$ are the same or different and are as defined above, (XVIII) —$CH(R_{A-aryl})(R_{A-heteroaryl})$ where $R_{A-aryl}$ and $R_{A-heteroaryl}$ are as defined above, (XIX) -cyclopentyl, -cyclohexyl, or -cycloheptyl ring fused to $R_{A-aryl}$, $R_{A-heteroaryl}$, $R_{A-heterocycle}$ where $R_{A-aryl}$ or $R_{A-heteroaryl}$ or $R_{A-heterocycle}$ are as defined above where one carbon of cyclopentyl, cyclohexyl, or -cycloheptyl is optionally replaced with NH, $NR_{N-5}$, O, or $S(=O)_{0-2}$, and where cyclopentyl, cyclohexyl, or -cycloheptyl can be optionally substituted with one or two —$C_1$–$C_3$ alkyl, —F, —OH, —SH, —C≡N, —$CF_3$, $C_1$–$C_6$ alkoxy, =O, or —$NR_{1-a}R_{1-b}$ where $R_{1-a}$ and $R_{1-b}$ are as defined above, (XX) $C_2$–$C_{10}$ alkenyl containing one or two double bonds optionally substituted with one, two or three substituents selected from the group consisting of $C_1$–$C_3$ alkyl, —F, —Cl, —Br, —I, —OH, —SH, —C≡N, —$CF_3$, $C_1$–$C_6$ alkoxy, —O-phenyl, and $NR_{1-a}R_{1-b}$ where $R_{1-a}$ and $R_{1-b}$ are as defined above, (XXI) $C_2$–$C_{10}$ alkynyl containing one or two triple bonds optionally substituted with one, two or three substituents selected from the group consisting of $C_1$–$C_3$ alkyl, —F, —Cl, —Br, —I, —OH, —SH, —C≡N, —$CF_3$, $C_1$–$C_6$ alkoxy, —O-phenyl, —$NR_{1-a}R_{1-b}$ where $R_{1-a}$ and $R_{1-b}$ are as defined above, (XXI) —(CH$_2$)$_{0-1}$—CHR$_{A-6}$—(CH$_2$)$_{0-1}$—R$_{A\text{-}aryl}$
where R$_{A\text{-}aryl}$ is as defined above and R$_{A-6}$ is —(CH$_2$)$_{0-6}$—OH, (XXII) —(CH$_2$)$_{0-1}$—CHR$_{A-4}$—(CH$_2$)$_{0-1}$R$_{A\text{-}heteroaryl}$
where R$_{A\text{-}heteroaryl}$ and R$_{A-6}$ is as defined above, (XXIII) —CH(—R$_{A\text{-}aryl}$ or R$_{A\text{-}heteroaryl}$)—CO—O (C$_1$–C$_4$ alkyl) where R$_{A\text{-}aryl}$ and R$_{A\text{-}heteroaryl}$ are as defined above, (XXIV) —CH(—CH$_2$—OH)—CH(—OH)-micro-NO$_2$, (XXV) (C$_1$–C$_6$ alkyl)-O—(C$_1$–C$_6$ alkyl)-OH, (XXVII) —CH$_2$—NH—CH$_2$—CH(—O—CH$_2$—CH$_3$)$_2$, (XXVIII) —H, (XXIX) —(CH$_2$)$_{0-6}$—C(=NR$_{1\text{-}a}$)(NR$_{1\text{-}a}$R$_{1\text{-}b}$) where R$_{1\text{-}a}$ and R$_{1\text{-}b}$ are as defined above; or (XXX)
—C=OC(HR$_6$)NHR$_7$, where R$_6$ and R$_7$ are as defined below,
—C=OR$_7$, where R$_7$ is as defined below,
—C=OOR$_7$, where R$_7$ is as defined below, or
—SOOR$_7$ where R$_7$ is as defined below,
wherein R$_6$ is:
hydrogen,
C$_1$–C$_3$ alkyl,
phenyl,
thioalkoxyalkyl,
alkyl substituted aryl,
cycloalkyl,
cycloalkylalkyl,
hydroxyalkyl,
alkoxyalkyl,
aryloxyalkyl,
haloalkyl,
carboxyalkyl,
alkoxycarbonylalkyl,
aminoalkyl,
(N-protected)aminoalkyl,
alkylaminoalkyl,
((N-protected)(alkyl)amino)alkyl,
dialkylaminoalkyl,
guanidinoalkyl,
lower alkenyl,
heterocyclic,
(heterocyclic)alkyl),
arylthioalkyl,
arylsulfonylalkyl,
(heterocyclic)thioalkyl,
(heterocyclic)sulfonylalkyl,
(heterocyclic)oxyalkyl,
arylalkoxyalkyl,
arylthioalkoxyalkyl,
arylalkylsulfonylalkyl,
(heterocyclic))alkoxyalkyl,
(heterocyclic)thioalkoxyalkyl,
(heterocyclic)alkylsulfonylalkyl,
cycloalkyloxyalkyl,
cycloalkylthioalkyl,
cycloalkylsulfonylalkyl,
cycloalkylalkoxyalkyl,
cycloalkylthioalkoxyalkyl,
cycloalkylalkylsulfonylalkyl,
aminocarbonyl,
alkylaminocarbonyl,
dialkylaminocarbonyl,
aroylalkyl,
(heterocyclic)carbonylalkyl,
polyhydroxyalkyl,
aminocarbonylalkyl,
alkylaminocarbonylalkyl,
dialkylaminocarbonylalkyl,
aryloxyalkyl, or
alkylsulfonylalkyl,
wherein heterocyclic is pyridyl, thiazolyl, isothiazolyl, oxazolyl, isoxazolyl, furanyl, thienyl, tetrahydrofuranyl, tetrahydrothienyl and tetrahydro[2H]pyranyl and wherein the heterocycle is unsubstituted or substituted with one to three substituents independently selected from hydroxy, halo, amino, alkylamino, dialkylamino, alkoxy, polyalkoxy, haloalkyl, cycloalkyl, cycloalkylalkyl, aryl, arylalkyl, COOH, —SO$_3$H, lower alkenyl or lower alkyl;
wherein R$_7$ is:
C$_1$–C$_3$ alkyl,
phenyl,
thioalkoxyalkyl,
(aryl)alkyl,
cycloalkyl,
cycloalkylalkyl,
hydroxyalkyl,
alkoxyalkyl,
aryloxyalkyl,
haloalkyl,
carboxyalkyl,
alkoxycarbonylalkyl,
aminoalkyl,
(N-protected)aminocalkyl,
alkylaminoalkyl,
((N-protected)(alkyl)amino)alkyl,
dialkylaminoalkyl,
guanidinoalkyl,
lower alkenyl,
heterocyclic,
(heterocyclic)alkyl),
arylthioalkyl,
arylsulfonylalkyl,
(heterocyclic)thioalkyl,
(heterocyclic)sulfonylalkyl,
(heterocyclic)oxyalkyl,
arylalkoxyalkyl,
arylthioalkoxyalkyl,
arylalkylsulfonylalkyl,
(heterocyclic))alkoxyalkyl,
(heterocyclic)thioalkoxyalkyl,
(heterocyclic)alkylsulfonylalkyl,
cycloalkyloxyalkyl,
cycloalkylthioalkyl,
cycloalkylsulfonylalkyl,
cycloalkylalkoxyalkyl,
cycloalkylthioalkoxyalkyl,
cycloalkylalkylsulfonylalkyl,
aminocarbonyl,
alkylaminocarbonyl,
dialkylaminocarbonyl,
aroylalkyl,
(heterocyclic)carbonylalkyl,
polyhydroxyalkyl,
aminocarbonylalkyl,
alkylaminocarbonylalkyl,
dialkylaminocarbonylalkyl,
aryloxyalkyl, or
alkylsulfonylalkyl,
wherein heterocyclic is pyridyl, thiazolyl, isothiazolyl, oxazolyl, isoxazolyl, furanyl, thienyl, tetrahydrofuranyl, tetrahydrothienyl and tetrahydro[2H]pyranyl and wherein the heterocycle is unsubstituted or substituted with one to three substituents independently selected from hydroxy, halo, amino, alkylamino, dialkylamino, alkoxy, polyalkoxy, haloalkyl, cycloalkyl, cycloalkylalkyl, aryl, arylalkyl, COOH, —SO$_3$H, lower alkenyl or lower alkyl;

where X is —N or —O, with the proviso that when X is O, R$_B$ is absent; and when X is N, R$_B$, is:

(I) —C$_1$–C$_{10}$ alkyl optionally substituted with one, two or three substituents selected from the group consisting of C$_1$–C$_3$ alkyl, —F, —Cl, —Br, 'I, —OH, —SH, —C≡N, —CF$_3$, C$_1$–C$_6$ alkoxy, —O-phenyl, —NR$_{1-a}$R$_{1-b}$ where R$_{1-a}$ and R$_{1-b}$ are as defined above, —OC=O NR$_{1-a}$R$_{1-b}$ where R$_{1-a}$ and R$_{1-b}$ are as defined above, —S(=O)$_{0-2}$ R$_{1-a}$ where R$_{1-a}$ is as defined above, —NR$_{1-a}$C=O NR$_{1-a}$R$_{1-b}$ where R$_{1-a}$ and R$_{1-b}$ are as defined above, —C=O NR$_{1-a}$R$_{1-b}$ where R$_{1-a}$ and R$_{1-b}$ are as defined above, and —S(=O)$_2$ NR$_{1-a}$R$_{1-b}$ where R$_{1-a}$ and R$_{1-b}$ are as defined above, (II) —(CH$_2$)$_{0-3}$—(C$_3$–C$_8$) cycloalkyl where cycloalkyl can be optionally substituted with one, two or three substituents selected from the group consisting of C$_1$–C$_3$ alkyl, —F, —Cl, —Br, —I, —OH, —SH, —C≡N, —CF$_3$, C$_1$–C$_6$ alkoxy, —O-phenyl, —CO—OH, —CO—O—(C$_1$–C$_4$ alkyl), and —NR$_{1-a}$R$_{1-b}$ where R$_{1-a}$ and R$_{1-b}$ are as defined above, (III) —(CR$_{B-x}$R$_{B-y}$)$_{0-4}$—R$_{B-aryl}$ where R$_{B-x}$ and R$_{B-y}$ are (A) —H, (B) C$_1$–C$_4$ alkyl optionally substituted with one or two —OH, (C) C$_1$–C$_4$ alkoxy optionally substituted with one, two, or three of —F, (D) —(CH$_2$)$_{0-4}$–C$_3$–C$_7$ cycloalkyl, (E) C$_2$–C$_6$ alkenyl containing one or two double bonds, (F) C$_2$–C$_6$ alkynyl contianing one or two triple bonds, or (G) phenyl, and where R$_{B-x}$ and R$_{B-y}$ are taken together with the carbon to which they are attached to form a carbocycle of three, four, five, six or seven carbon atoms, optionally where one carbon atom is replaced by a heteroatom selected from the group consisting of —O—, —S—, —SO$_2$—, and —NR$_{N-2}$ where R$_{N-2}$ is as defined above, and R$_{B-aryl}$ is the same as R$_{N-aryl}$ and is defined above (IV) —(CR$_{B-x}$R$_{B-y}$)$_{0-4}$—R$_{B-heteroaryl}$ where R$_{B-heteroaryl}$ is the same as R$_{N-heteroaryl}$, R$_{B-x}$, and R$_{B-y}$ are as defined above, (V) —(CR$_{B-x}$R$_{B-y}$)$_{0-4}$—R$_{B-aryl}$—R$_{B-aryl}$ where R$_{B-aryl}$, R$_{B-x}$, and R$_{B-y}$ are as defined above, (VI) —(CR$_{B-x}$R$_{B-y}$)$_{0-4}$—R$_{B-aryl}$—R$_{B-heteroaryl}$ where R$_{B-aryl}$, R$_{B-heteroaryl}$, R$_{B-x}$ and R$_{B-y}$ are as defined above, (VII) —(CR$_{B-x}$R$_{B-y}$)$_{0-4}$—R$_{B-heteroaryl}$—R$_{B-aryl}$ where R$_{B-heteroaryl}$, R$_{B-aryl}$, R$_{B-x}$ and R$_{B-y}$ are as defined above, (VIII) —(CR$_{B-x}$R$_{B-y}$)$_{O-4}$—R$_{B-heteroaryl}$—R$_{B-heteroaryl}$ where R$_{B-heteroaryl}$, R$_{B-x}$ and R$_{B-y}$ are as defined above, (IX) —(CR$_{B-x}$R$_{B-y}$)$_{0-4}$—R$_{B-arly}$—R$_{B-heterocycle}$ where R$_{B-heterocycle}$ is defined as R$_{1-heterocycle}$, and where R$_{B-aryl}$, R$_{B-x}$ and R$_{B-y}$ are as defined above, (X) —(CR$_{B-x}$R$_{B-y}$)$_{0-4}$—R$_{B-heteroaryl}$—R$_{B-heterocycle}$ where R$_{B-heteroaryl}$, R$_{B-heterocycle}$, R$_{B-x}$ and R$_{B-y}$ are as defined above, (XI) —(CR$_{B-x}$R$_{B-y}$)$_{0-4}$—R$_{B-heterocycle}$—R$_{B-aryl}$ where R$_{B-heterocycle}$, R$_{B-aryl}$, R$_{B-x}$ and R$_{B-y}$ are as defined above, (XII) —(CR$_{B-x}$R$_{B-y}$)$_{0-4}$—R$_{B-heterocycle}$—R$_{B-heteroaryl}$ where R$_{B-heterocycle}$, R$_{B-heteroaryl}$, R$_{B-x}$ and R$_{B-y}$ are as defined above, (XIII) —(CR$_{B-x}$R$_{B-y}$)$_{0-4}$—R$_{B-heterocycle}$—R$_{B-heterocycle}$ where R$_{B-heterocycle}$, R$_{B-x}$ and R$_{B-y}$ are as defined above, (XIV) —(CR$_{B-x}$R$_{B-y}$)$_{0-4}$—R$_{B-heterocycle}$ where R$_{B-heterocycle}$ R$_{B-x}$ and R$_{B-y}$ are as defined above, (XV) —[C(R$_{B-1}$)(R$_{B-2}$)]$_{1-3}$—CO—N—(R$_{B-3}$)$_2$ where R$_{B-1}$ and R$_{B-2}$ are the same or different and are selected from the group consisting of:

(A) —H, (B) —C$_1$–C$_6$ alkyl, optionally substituted with one, two or three substituents selected from the group consisting of C$_1$–C$_3$ alkyl, —F, —Cl, —Br, —I, —OH, —SH, —C≡N, —CF$_3$, C$_1$–C$_6$ alkoxy, —O-phenyl, and —NR$_{1-a}$R$_{1-b}$ where R$_{1-a}$ and R$_{1-b}$ are as defined above, (C) C$_2$–C$_6$ alkenyl with one or two double bonds, optionally substituted with one, two or three substituents selected from the group consisting of C$_1$–C$_3$ alkyl, —F, —Cl, 'Br, —I, —OH, —SH, —C≡N, —CF$_3$, C$_1$–C$_6$ alkoxy, —O-phenyl, and —NR$_{1-a}$R$_{1-b}$ where R$_{1-a}$ and R$_{1-b}$ are as defined above, (D) C$_2$–C$_6$ alkynyl with one or two triple bonds, optionally substituted with one, two or three substituents selected from the group consisting of C$_1$–C$_3$ alkyl, —F, —Cl, —Br, —I, —OH, —SH, —C≡N, —CF$_3$, C$_1$–C$_6$ alkoxy, —O-phenyl, and —NR$_{1-a}$R$_{1-b}$ where R$_{1-a}$ and R$_{1-b}$ are as defined above, (E) —(CH$_2$)$_{1-2}$—S(O)$_{0-2}$—(C$_1$–C$_6$ alkyl), (F) —(CH$_2$)$_{0-4}$—C$_3$–C$_7$ cycloalkyl, optionally substituted with one, two or three substituents selected from the group consisting of C$_1$–C$_3$ alkyl, —F, —Cl, —Br, —I, —OH, —SH, —C≡N, —CF$_3$, C$_1$–C$_6$ alkoxy, —O-phenyl, and NR$_{1-a}$R$_{1-b}$ where R$_{1-a}$ and R$_{1-b}$ are as defined above, (G) —(C$_1$–C$_4$ alkyl)-R$_{B'aryl}$ where R$_{B'aryl}$ is as defined above for R$_{1-aryl}$, (H) —(C$_1$–C$_4$ alkyl)-R$_{B-heteroaryl}$ where R$_{B-heteroaryl}$ is as defined above, (I) —(C$_1$–C$_4$ alkyl)-R$_{B-heterocycle}$ where R$_{B-heterocycle}$ is as defined above, (J) —R$_{B-heteroaryl}$ where R$_{B-heteroaryl}$ is as defined above, (K) —R$_{B-heterocycle}$ where R$_{B-heterocycle}$ is as defined above, (M) —(CH$_2$)$_{1-4}$—R$_{B-4}$(CH$_2$)$_{0-4}$—R$_{B'aryl}$ where R$_{B-4}$ is —O—, —S— or —NR$_{B-5}$— where R$_{B-5}$ is C$_1$–C$_6$ alkyl, and where R$_{B-aryl}$ is defined above, (N) —(CH$_2$)$_{1-4}$—R$_{B-4}$—(CH$_2$)$_{0-4}$—R$_{B-heteroaryl}$ where R$_{B-4}$ and R$_{B-heteroaryl}$ are as defined above, and (O) —R$_{B'aryl}$ where R$_{B-aryl}$ is as defined above, and where $R_{B-3}$ is the same or different and is:
(A) —H,
(B) —$C_1$–$C_6$ alkyl optionally substituted with one, two or three substituents selected from the group consisting of $C_1$–$C_3$ alkyl, —F, —Cl, —Br, —I, —OH, —SH, —C≡N, —$CF_3$, $C_1$–$C_6$ alkoxy, —O-phenyl, and —$NR_{1-a}R_{1-b}$ where $R_{1-a}$ and $R_{1-b}$ are as defined above,
(C) $C_2$–$C_6$ alkenyl with one or two double bonds, optionally substituted with one, two or three substituents selected from the group consisting of $C_1$–$C_3$ alkyl, —F, —Cl, —Br, —I, —OH, —SH, —C≡N, —$CF_3$, $C_1$–$C_6$ alkoxy, —O-phenyl, and —$NR_{1-a}R_{1-b}$ where $R_{1-a}$ and $R_{1-b}$ are as defined above,
(D) $C_2$–$C_6$ alkynyl with one or two triple bonds, optionally substituted with one, two or three substituents selected from the group consisting of $C_1$–$C_3$ alkyl, —F, —Cl, —Br, —I, —OH, —SH, —C≡N, —$CF_3$, $C_1$–$C_6$ alkoxy, —O-phenyl, and —$NR_{1-a}R_{1-b}$ where $R_{1-a}$ and $R_{1-b}$ are as defined above,
(E) —$(CH_2)_{0-4}$—$C_3$–$C_7$ cycloalkyl, optionally substituted with one, two or three substituents selected from the group consisting of $C_1$–$C_3$ alkyl, —F, —Cl, —Br, —I, —OH, —SH, —C≡N, —$CF_3$, $C_1$–$C_6$ alkoxy, —O-phenyl, and —$NR_{1-a}R_{1-b}$ where $R_{1-a}$ and $R_{1-b}$ are as defined above,
(F) —$R_{B'-aryl}$ where $R_{B'-aryl}$ is as defined above,
(G) —$R_{B-heteroaryl}$ where $R_{B-heteroaryl}$ is as defined above,
(H) —$R_{B-heterocycle}$ where $R_{B-heterocycle}$ is as defined above,
(I) —($C_1$–$C_4$ alkyl)-$R_{B'-aryl}$ where $R_{B'-aryl}$ is as defined above,
(J) —($C_1$–$C_4$ alkyl)-$R_{B-heteroaryl}$ where $R_{B-heteroaryl}$ is as defined above,
(K) —($C_1$–$C_4$ alkyl)-$R_{B-heterocycle}$ where $R_{B-heterocycle}$ is as defined above, or
(XVI) —$CH(R_{B-aryl})_2$ where $R_{B-aryl}$ are the same or different and are as defined above,
(XVII) —$CH(R_{B-heteroaryl})_2$ where $R_{B-heteroaryl}$ are the same or different and are as defined above,
(XVIII) —$CH(R_{B-aryl})(R_{B-heteroaryl})$ where $R_{B-aryl}$ and $R_{B-heteroaryl}$ are as defined above,
(XIX) -cyclopentyl, -cyclohexyl, or -cycloheptyl ring fused to $R_{B-aryl}$ or $R_{B-heteroaryl}$ or $R_{B-heterocycle}$ where $R_{B-aryl}$ or $R_{B-heteroaryl}$ or $R_{B-heterocycle}$ are as defined above where one carbon of cyclopentyl, cyclohexyl, or -cycloheptyl is optionally replaced with NH, $NR_{N-5}$, O, or $S(=O)_{0-2}$, and where cyclopentyl, cyclohexyl, or -cycloheptyl can be optionally substituted with one or two —$C_1$–$C_3$ alkyl, —F, —OH, —SH, —C≡N, —$CF_3$, $C_1$–$C_6$ alkoxy, =O, or —$NR_{1-a}R_{1-b}$ where $R_{1-a}$ and $R_{1-b}$ are as defined above,
(XX) $C_2$–$C_{10}$ alkenyl containing one or two double bonds optionally substituted with one, two or three substituents selected from the group consisting of $C_1$–$C_3$ alkyl, —F, —Cl, —Br, —I, —OH, —SH, —C≡N, —$CF_3$, $C_1$–$C_6$ alkoxy, 'O-phenyl, and —$NR_{1-a}R_{1-b}$ where $R_{1-a}$ and $R_{1-b}$ are as defined above,
(XXI) $C_2$–$C_{10}$ alkynyl containing one or two triple bonds optionally substituted with one, two or three substituents selected from the group consisting of $C_1$–$C_3$ alkyl, —F, —Cl, —Br, —I, —OH, —SH, —C≡N, —$CF_3$, $C_1$–$C_6$ alkoxy, —O-phenyl, and —$NR_{1-a}R_{1-b}$ where $R_{1-a}$ and $R_{1-b}$ are as defined above,
(XXI) —$(CH_2)_{0-1}$—$CH_{C-6}$—$(CH_2)_{0-1}$—$RB_{B-aryl}$ where $R_{B-aryl}$ is as defined above and $R_{C-6}$ is —$(CH_2)_{0-6}$—OH,
(XXII) —$CH_2)_{0-1}$—$CHR_{B-6}$—$(CH_2)_{0-1}$—$R_{B-heteroaryl}$ where $R_{B-heteroaryl}$ and $R_{C-6}$ is as defined above,
(XXIII) —CH(—$R_{B-aryl}$ or $R_{B-heteroaryl}$)—CO—O($C_1$–$C_4$ alkyl) where $R_{B-aryl}$ and $R_{B-heteroaryl}$ are as defined above,
(XXIV) —CH(—$CH_2$—OH)—CH(—OH)-micro-$NO_2$,
(XXV) ($C_1$–$C_6$ alkyl)-O—($C_1$–$C_6$ alkyl)-OH,
(XXVII) —$CH_2$—NH—$CH_2$—CH(—O—$CH_2$—$CH_3$)_2,
(XXVIII) —H, or
(XXIX) —$(CH_2)_{0-6}$—C(=$NR_{1-a}$)($NR_{1-a}R_{1-b}$) where $R_{1-a}$ and $R_{1-b}$ are as defined above,
and pharmaceutically acceptable salts thereof.

Disclosed is the use of a compound of formula (XV)

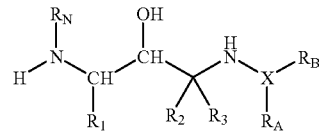

(XV)

where $R_1$, $R_2$, $R_3$, $R_N$, $R_A$, $R_B$, and X are as defined above for the compound of formula (XV), and pharmaceutically acceptable salts thereof for the manufacture of a medicament for use in treating a patient who has, or in preventing a patient from getting, a disease or condition selected from the group consisting of Alzheimer's disease, for helping prevent or delay the onset of Alzheimer's disease, for treating patients with mild cognitive impairment (MCI) and preventing or delaying the onset of Alzheimer's disease in those who would progress from MCI to AD, for treating Down's syndrome, for treating humans who have Hereditary Cerebral Hemorrhage with Amyloidosis of the Dutch-Type, for treating cerebral amyloid angiopathy and preventing its potential consequences, i.e. single and recurrent lobar hemorrhages, for treating other degenerative dementias, including dementias of mixed vascular and degenerative origin, dementia associated with Parkinson's disease, dementia associated with progressive supranuclear palsy, dementia associated with cortical basal degeneration, diffuse Lewy body type of Alzheimer's disease and who is in need of such treatment.

The present invention provides compounds, compositions, kits, and methods for inhibiting beta-secretase-mediated cleavage of amyloid precursor protein (APP). More particularly, the compounds, compositions, and methods of the invention are effective to inhibit the production of A beta peptide and to treat or prevent any human or veterinary disease or condition associated with a pathological form of A beta peptide.

The compounds, compositions, and methods of the invention are useful for treating humans who have Alzheimer's Disease (AD), for helping prevent or delay the onset of AD, for treating patients with mild cognitive impairment (MCI), and preventing or delaying the onset of AD in those patients who would otherwise be expected to progress from MCI to AD, for treating Down's syndrome, for treating Hereditary Cerebral Hemorrhage with Amyloidosis of the Dutch Type, for treating cerebral beta-amyloid angiopathy and preventing its potential consequences such as single and recurrent lobar hemorrhages, for treating other degenerative dementias, including dementias of mixed vascular and degenerative origin, for treating dementia associated with Parkinson's disease, dementia associated with progressive supranuclear palsy, dementia associated with cortical basal degeneration, and diffuse Lewy body type AD.

The compounds employed in the methods of the invention possess beta-secretase inhibitory activity. The inhibitory activities of the compounds employed in the methods of the invention are readily demonstrated, for example, using one or more of the assays described herein or known in the art.

DETAILED DESCRIPTION OF THE INVENTION

The invention includes compounds of formula (XV) that are useful in treating and preventing Alzheimer's disease. The anti-Alzheimer's compounds of formula (XV) are made by methods well known to those skilled in the art from starting compounds known to those skilled in the art. The process chemistry is well known to those skilled in the art. Examples of preparing various compounds of formula (XV) are included in charts A–C. One skilled in the art will appreciate that these are all well known reactions in organic chemistry. A chemist skilled in the art, knowing the chemical structure of the biologically active compounds of formula (XV) of the invention would be able to prepare them by known methods from known starting materials without any additional information. The explanation below therefore is not necessary but is deemed helpful to those skilled in the art who desire to make compounds of the invention.

CHART A illustrates a general method of synthesizing compounds of the invention. The anti-Alzheimer's coumpounds of formula (XV) are prepared by starting with the corresponding epoxide (I). The epoxides (I) are well known to those skilled in the art or can be readily prepared from known compounds by methods well known to those skilled in the art. The compounds of formula (XV) of the present invention have at least two enantiomeric centers which give four enantiomers. The first of these enantiomeric centers derives from the epoxide starting material (I). If a desired enantiomer is preferred, it is preferred to commercially obtain or produce the desired enantiomer (S or R) rather than produce an enantiomerically impure mixture and then have to separate out the desired enantiomer. For the epoxide (I), $R_1$ is:

- (I) $C_1$–$C_6$ alkyl, optionally substituted with one, two or three substituents selected from the group consisting of $C_1$–$C_3$ alkyl, $C_1$–$C_7$ alkyl (optionally substituted with $C_1$–$C_3$ alkyl and $C_1$–$C_3$ alkoxy), —F, —Cl, —Br, —I, —OH, —SH, —C≡N, —CF$_3$, $C_1$–$C_3$ alkoxy, —NR$_{1-a}$R$_{1-b}$ where R$_{1-a}$ and R$_{1-b}$ are —H or $C_1$–$C_6$ alkyl, and —OC=O NR$_{1-a}$R$_{1-b}$ where R$_{1-a}$ and R$_{1-b}$ are as defined above,
- (II) —CH$_2$—S(O)$_{0-2}$—($C_1$–$C_6$ alkyl),
- (III) —CH$_2$—CH$_2$—S(O)$_{0-2}$—($C_1$–$C_6$ alkyl),
- (IV) $C_2$–$C_6$ alkenyl with one or two double bonds, optionally substituted with one, two or three substituents selected from the group consisting of —F, —Cl, —OH, —SH, —C≡N, —CF$_3$, $C_1$–$C_3$ alkoxy, and —NR$_{1-a}$R$_{1-b}$ where R$_{1-a}$ and R$_{1-b}$ are —H or $C_1$–$C_6$ alkyl,
- (V) $C_2$–$C_6$ alkynyl with one or two triple bonds, optionally substituted with one, two or three substituents selected from the group consisting of —F, —Cl, —OH, —SH, —C≡N, —CF$_3$, $C_1$–$C_3$ alkoxy, and —NR$_{1-a}$R$_{1-b}$ where R$_{1-a}$ and R$_{1-b}$ are —H or $C_1$–$C_6$ alkyl,
- (VI) —(CH$_2$)$_{n1}$—(R$_{1-aryl}$) where n$_1$ is zero or one and where R$_{1-aryl}$ is phenyl, 1-naphthyl, 2-naphthyl and indanyl, indenyl, dihydronaphthalyl, or tetralinyl optionally substituted with one, two, three or four of the following substituents on the aryl ring:
  - (A) $C_1$–$C_6$ alkyl optionally substituted with one, two or three substituents selected from the group consisting of $C_1$–$C_3$ alkyl, —F, —Cl, —Br, —I, —OH, —SH, —C≡N, —CF$_3$, and $C_1$–$C_3$ alkoxy, and —NR$_{1-a}$R$_{1-b}$ where R$_{1-a}$ and R$_{1-b}$ are as defined above,
  - (B) $C_2$–$C_6$ alkenyl with one or two double bonds, optionally substituted with one, two or three substituents selected from the group consisting of —F, —Cl, —OH, —SH, —C≡N, —CF$_3$, $C_1$–$C_3$ alkoxy, and —NR$_{1-a}$R$_{1-b}$ where R$_{1-a}$ and R$_{1-b}$ are —H or $C_1$–$C_6$ alkyl,
  - (C) $C_2$–$C_6$ alkynyl with one or two triple bonds, optionally substituted with one, two or three substituents selected from the group consisting of —F, —Cl, —OH, —SH, —C≡N, —CF$_3$, $C_1$–$C_3$ alkoxy, and —NR$_{1-a}$R$_{1-b}$ where R$_{1-a}$ and R$_{1-b}$ are —H or $C_1$–$C_6$ alkyl,
  - (D) —F, Cl, —Br or —I,
  - (F) —$C_1$–$C_6$ alkoxy optionally substituted with one, two or three of —F,
  - (G) —NR$_{N-2}$R$_{N-3}$ where R$_{N-2}$ and R$_{N-3}$ are as defined below,
  - (H) —OH,
  - (I) —C≡N,
  - (J) $C_3$–$C_7$ cycloalkyl, optionally substituted with one, two or three substituents selected from the group consisting of —F, —Cl, —OH, —SH, —C≡N, —CF$_3$, $C_1$–$C_3$ alkoxy, and —NR$_{1-a}$R$_{1-b}$ where R$_{1-a}$ and R$_{1-b}$ are —H or $C_1$–$C_6$ alkyl,
  - (K) —O'($C_1$–$C_4$ alkyl),
  - (L) —SO$_2$—NR$_{1-a}$R$_{1-b}$ where R$_{1-a}$ and R$_{1-b}$ are as defined above,
  - (M) —CO—NR$_{1-a}$R$_{1-b}$ where R$_{1-a}$ and R$_{1-b}$ are as defined above, or
  - (N) —SO$_2$—($C_1$–$C_4$ alkyl),
- (VII) —(CH$_2$)$_{n1}$—(R$_{1-heteroaryl}$) where n$_1$ is as defined above and where R$_{1-heteroaryl}$ is selected from the group consisting of:
  pyridinyl,
  pyrimidinyl,
  quinolinyl,
  benzothienyl,
  indolyl,
  indolinyl,
  pryidazinyl,
  pyrazinyl,
  isoquinolyl,
  quinazolinyl,
  quinoxalinyl,
  phthalazinyl,
  irnidazolyl,
  isoxazolyl,
  pyrazolyl,
  oxazolyl,
  thiazolyl,
  indolizinyl,
  indazolyl,
  benzothiazolyl,
  benzimidazolyl,
  benzofuranyl, furanyl,
thienyl,
pyrrolyl,
oxadiazolyl,
thiadiazolyl,
triazolyl,
tetrazolyl,
oxazolopyridinyl,
imidazopyridinyl,
isothiazolyl,
naphthyridinyl,
cinnolinyl,
carbazolyl,
beta-carbolinyl,
isochromanyl,
chromanyl,
tetrahydroisoquinolinyl,
isoindolinyl,
isobenzotetrahydrofiuranyl,
isobenzotetrahydrothienyl,
isobenzothienyl,
benzoxazolyl,
pyridopyridinyl,
benzotetrahydrofuranyl,
benzotetrahydrothienyl,
purinyl,
benzodioxolyl,
triazinyl,
phenoxazinyl,
phenothiazinyl,
pteridinyl,
benzothiazolyl,
imidazopyridinyl,
imidazothiazolyl,
dihydrobenzisoxazinyl,
benzisoxazinyl,
benzoxazinyl,
dihydrobenzisothiazinyl,
benzopyranyl,
benzothiopyranyl,
coumarinyl,
isocoumarinyl,
chromonyl,
chromanonyl,
pyridinyl-N-oxide,
  tetrahydroquinolinyl
  dihydroquinolinyl
  dihydroquinolinonyl
  dihydroisoquinolinonyl
  dihydrocoumarinyl
  dihydroisocoumarinyl
  isoindolinonyl
  benzodioxanyl
  benzoxazolinonyl
  pyrrolyl N-oxide,
  pyrimidinyl N-oxide,
  pyridazinyl N-oxide,
  pyrazinyl N-oxide,
  quinolinyl N-oxide,
  indolyl N-oxide,
  indolnyl N-oxide,
  isoquinolyl N-oxide,
  quinazolinyl N-oxide,
  quinoxalinyl N-oxide,
  phthalazinyl N-oxide,
  imidazolyl N-oxide,
  isoxazolyl N-oxide,
  oxazolyl N-oxide,
  thiazolyl N-oxide,
  indolizinyl N-oxide,
  indazolyl N-oxide,
  benzothiazolyl N-oxide,
  benzimidazolyl N-oxide,
  pyrrolyl N-oxide,
  oxadiazolyl N-oxide,
  thiadiazolyl N-oxide,
  triazolyl N-oxide,
  tetrazolyl N-oxide,
  benzothiopyranyl S-oxide, and
  benzothiopyranyl S,S-dioxide, where the $R_{1\text{-}heteroary}$ group is bonded to —$(CH_2)_{n1}$— by any ring atom of the parent $R_{1\text{-}heteroaryl}$ group substituted by hydrogen such that the new bond to the $R_{1\text{-}heteroaryl}$ group replaces the hydrogen atom and its bond, where heteroaryl is optionally substituted with one, two, three or four of:

(1) $C_1$–$C_6$ alkyl optionally substituted with one, two or three substituents selected from the group consisting of $C_1$–$C_3$ alkyl, —F, —Cl, —Br, —I, —OH, —SH, —C≡N, —CF$_3$, $C_1$–$C_3$ alkoxy, and —NR$_{1\text{-}a}$R$_{1\text{-}b}$ where R$_{1\text{-}a}$ and R$_{1\text{-}b}$ are as defined above, (2) $C_2$–$C_6$ alkenyl with one or two double bonds, optionally substituted with one, two or three substituents selected from the group consisting of —F, —Cl, —OH, —SH, —C≡N, —CF$_3$, $C_1$–$C_3$ alkoxy, and —NR$_{1\text{-}a}$R$_{1\text{-}b}$ where R$_{1\text{-}a}$ and R$_{1\text{-}b}$ are —H or $C_1$–$C_6$ alkyl, (3) $C_2$–$C_6$ alkynyl with one or two triple bonds, optionally substituted with one, two or three substituents selected from the group consisting of —F, —Cl, —OH, —SH, —C≡N, —CF$_3$, $C_1$–$C_3$ alkoxy, and —NR$_{1\text{-}a}$R$_{1\text{-}b}$ where R$_{1\text{-}a}$ and R$_{1\text{-}b}$ are —H or $C_1$–$C_6$ alkyl, (4) —F, Cl, —Br or —I, (6) —$C_1$–$C_6$ alkoxy optionally substituted with one, two, or three of —F, (7) —NR$_{N\text{-}2}$R$_{N\text{-}3}$ where R$_{N\text{-}2}$ and R$_{N\text{-}3}$ are as defined below, (8) —OH, (9) —C≡N,

(10) $C_3$–$C_7$ cycloalkyl, optionally substituted with one, two or three substituents selected from the group consisting of —F, —Cl, —OH, —SH, —C≡N, —CF$_3$, $C_1$–$C_3$ alkoxy, and —NR$_{1\text{-}a}$R$_{1\text{-}b}$ where R$_{1\text{-}a}$ and R$_{1\text{-}b}$ are —H or $C_1$–$C_6$ alkyl,

(11) —CO—($C_1$–$C_4$ alkyl),

(12) —SO$_2$—NR$_{1\text{-}a}$R$_{1\text{-}b}$ where R$_{1\text{-}a}$ and R$_{1\text{-}b}$ are as defined above,

(13) —CO—NR$_{1\text{-}a}$R$_{1\text{-}b}$ where R$_{1\text{-}a}$ and R$_{1\text{-}b}$ are as defined above, or

(14) —SO$_2$—($C_1$–$C_4$ alkyl), with the proviso that when $n_1$ is zero $R_{1\text{-}heteroaryl}$ is not bonded to the carbon chain by nitrogen; or (VIII) —$(CH_2)_{n1}$—$(R_{1\text{-}heterocycle})$ where $n_1$ is as defined above and $R_{1\text{-}heterocycle}$ is selected from the group consisting of:

morpholinyl,
thiomorpholinyl,
thiomorpholinyl S-oxide,
thiomorpholinyl S,S-dioxide,
piperazin,
homopiperazinyl,
pyrrolidinyl, pyrrolinyl,
tetrahydropyranyl,
piperidinyl,
tetrahydrofyranyl,
tetrahydrothienyl,
homopiperidinyl,
homomorpholinyl,
homothiomorpholinyl,
homothiomorpholinyl S,S-dioxide,
oxazolidinonyl,
dihydropyrazolyl,
dihydropyrrolyl,
dihydropyrazinyl,
dihydropyridinyl,
dihydropyrimidinyl,
dihydrofuryl,
dihydropyranyl,
tetrahydrothienyl S-oxide,
tetrahydrothienyl S,S-dioxide, and
homothiomorpholinyl S-oxide, where the $R_{1\text{-}heterocycle}$ group is bonded by any atom of the parent $R_{1\text{-}heterocycle}$ group substituted by hydrogen such that the new bond to the $R_{1\text{-}heterocycle}$ group replaces the hydrogen atom and its bond, where heterocycle is optionally substituted with one, two, three or four:

(1) $C_1$–$C_6$ alkyl optionally substituted with one, two or three substituents selected from the group consisting of $C_1$–$C_3$ alkyl, —F, —Cl, —Br, —I, —OH, —SH, —C≡N, —CF$_3$, $C_1$–$C_3$ alkoxy, and —NR$_{1\text{-}a}$R$_{1\text{-}b}$ where $R_{1\text{-}a}$ and $R_{1\text{-}b}$ are as defined above, (2) $C_2$–$C_6$ alkenyl with one or two double bonds, optionally substituted with one, two or three substituents selected from the group consisting of —F, —Cl, —OH, —SH, —C≡N, —CF$_3$, $C_1$–$C_3$ alkoxy, and NR$_{1\text{-}a}$R$_{1\text{-}b}$ where $R_{1\text{-}a}$ and $R_{1\text{-}b}$ are —H or $C_1$–$C_6$ alkyl, (3) $C_2$–$C_6$ alkynyl with one or two triple bonds, optionally substituted with one, two or three substituents selected from the group consisting of —F, —Cl, —OH, —SH, —C≡N, —CF$_3$, $C_1$–$C_3$ alkoxy, and —NR$_{1\text{-}a}$R$_{1\text{-}b}$ where $R_{1\text{-}a}$ and $R_{1\text{-}b}$ are —H or $C_1$–$C_6$ alkyl, (4) —F, Cl, —Br or —I, (5) $C_1$–$C_6$ alkoxy, (6) $C_1$–$C_6$ alkoxy optionally substituted with one, two, or three —F, (7) —NR$_{N\text{-}2}$R$_{N\text{-}3}$ where $R_{N\text{-}2}$ and $R_{N\text{-}3}$ are as defined below, (8) —OH, (9) —C≡N,

(10) $C_3$–$C_7$ cycloalkyl, optionally substituted with one, two or three substituents selected from the group consisting of —F, —Cl, —OH, —SH, —C≡N, —CF$_3$, $C_1$–$C_3$ alkoxy, and —NR$_{1\text{-}a}$R$_{1\text{-}b}$ where $R_{1\text{-}a}$ and $R_{1\text{-}b}$ are —H or $C_1$–$C_6$ alkyl,

(11) —CO—($C_1$–$C_4$ alkyl),

(12) —SO$_2$NR$_{1\text{-}a}$R$_{1\text{-}b}$ where $R_{1\text{-}a}$ and $R_{1\text{-}b}$ are as defined above,

(13) —CO—NR$_{1\text{-}a}$R$_{1\text{-}b}$ where $R_{1\text{-}a}$ and $R_{1\text{-}b}$ are as defined above,

(14) —SO$_2$—($C_1$–$C_4$ alkyl), or

(15) =O, with the proviso that when $n_1$ is zero $R_{1\text{-}heterocycle}$ is not bonded to the carbon chain by nitrogen.

When $R_1$ is $R_{1\text{-}heteroaryl}$ or $R_{1\text{-}heterocycle}$ the bond from the $R_{1\text{-}heteroaryl}$ or $R_{1\text{-}heterocycle}$ group to the —(CH$_2$)$_{n1}$— group can be from any ring atom which has an available valence provided that such bond does not result in formation of a charged species or unstable valence. This means that the $R_{1\text{-}heteroaryl}$ or $R_{1\text{-}heterocycle}$ group is bonded to —CH$_2$)$_{n1}$— by any ring atom of the parent $R_{1\text{-}heteroaryl}$ or $R_{1\text{-}heterocycle}$ group which was substituted by hydrogen such that the new bond to the $R_{1\text{-}heteroary}$ or $R_{1\text{-}heterocycle}$ group replaces the hydrogen atom and its bond.

The epoxide (I) also contains the $R_2$ and $R_3$ groups. In the epoxide (I), $R_2$ and $R_3$ are each independently:

(I) —H, (II) $C_1$–$C_6$ alkyl, optionally substituted with one, two or three substituents selected from the group consisting of $C_1$–$C_3$ alkyl, —F, —Cl, —Br, —I, —OH, —SH, —C≡N, —CF$_3$, $C_1$–$C_3$ alkoxy, and —NR$_{1\text{-}a}$R$_{1\text{-}b}$ where $R_{1\text{-}a}$ and $R_{1\text{-}b}$ are as defined above, (III) —(CH$_2$)$_{0\text{-}4}$—R$_{2\text{-}1}$ where $R_{2\text{-}1}$ is $R_{1\text{-}aryl}$ or $R_{1\text{-}heteroaryl}$ where $R_{1\text{-}aryl}$ and $R_{1\text{-}heteroaryl}$ are as defined above (IV) $C_2$–$C_6$ alkenyl with one or two double bonds, (V) $C_2$–$C_6$ alkynyl with one or two triple bonds; or (VI) —(CH$_2$)$_{0\text{-}4}$—$C_3$–$C_7$ cycloalkyl, optionally substituted with one, two or three substituents selected from the group consisting of —F, —Cl, —OH, —SH, —C≡N, —CF$_3$, $C_1$–$C_3$ alkoxy, and —NR$_{1\text{-}a}$R$_{1\text{-}b}$ where $R_{1\text{-}a}$ and $R_{1\text{-}b}$ are —H or $C_1$–$C_6$ alkyl, and where $R_2$ and $R_3$ are taken together with the carbon to which they are attached to form a carbocycle of three, four, five, six, or seven carbon atoms, optionally where one carbon atom is replaced by a heteroatom selected from the group consisting of —O, —S—, —SO$_2$—, and —NR$_{N\text{-}2}$—, where $R_{N\text{-}2}$ is as defined below.

It is preferred that $R_2$ and $R_3$ both be —H. If $R_2$ and $R_3$ are not the same, an additional enantiomeric center is added to the molecule.

Before the synthesis is begun, the free amino group of the epoxide (I) must be protected with an amino protecting group. There are a number of methods well known to those skilled in the art for accomplishing this step. Amino protecting groups are well known to those skilled in the art. See for example, "Protecting Groups in Organic Synthesis", John Wiley and sons, New York, N.Y., 1981, Chapter 7; "Protecting Groups in Organic Chemistry", Plenum Press, New York, N.Y., 1973, Chapter 2. The function of the amino protecting group is to protect the free amino functionality (—NH$_2$) during subsequent reactions on the epoxide (I) which would not proceed well, either because the amino group would react and be functionalized in a way that is inconsistent with its need to be free for subsequent reactions, or the free amino group would interfere in the reaction. When the amino protecting group is no longer needed, it is removed by methods well known to those skilled in the art. By definition the amino protecting group must be readily removable as is known to those skilled in the art by methods well known to those skilled in the art.

Suitable amino PROTECTING GROUP is selected from the group consisting of t-butoxycarbonyl, benzyloxycarbonyl, formyl, trityl, acetyl, trichloroacetyl, dichloroacetyl, chloroacetyl, trifluoroacetyl, difluoroacetyl, fluoroacetyl, 4-phenylbenzyloxycarbonyl, 2-methylbenzyloxycarbonyl, 4-ethoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxycarbonyl, 2-(4-xenyl)isopropoxycarbonyl, 1,1-diphenyleth-1- yloxycarbonyl, 1,1-diphenylprop-1-yloxycarbonyl, 2-phenylprop-2-yloxycarbonyl, 2-(p-toluyl)prop-2-yloxycarbonyl, cyclopentanyloxycarbonyl, 1-methylcyclopentanyloxycarbonyl, cyclohexanyloxycarbonyl, 1-methylcyclohexanyloxycabonyl, 2-methylcyclohexanyloxycarbonyl, 2-(4-toluylsulfonyl)ethoxycarbonyl, 2-(methylsulfonyl)ethoxycarbonyl, 2-(triphenylphosphino)ethoxycarbonyl, fluorenylmethoxycarbonyl, 2-(trimethylsilyl)ethoxycarbonyl, allyloxycarbonyl, 1-(trimethylsilylmethyl)prop-1-enyloxycarbonyl, 5-benzisoxalylmethoxycarbonyl, 4-acetoxybenzyloxycarbonyl, 2,2,2-trichloroethoxycarbonyl, 2-ethynyl-2-propoxycarbonyl, cyclopropylmethoxycarbonyl, 4-(decyloxy)benzyloxycarbonyl, isobornyloxycarbonyl and 1-piperidyloxycarbonyl, 9-fluorenylmethyl carbonate, —CH═CH═CH$_2$ and phenyl-C(═N—)—H. It is preferred that the protecting group be t-butoxycarbonyl (BOC) and benzyloxycarbonyl (CBZ), it is more preferred that the protecting group be t-butoxycarbonyl. One skilled in the art will understand the preferred methods of introducing a t-butoxycarbonyl or benzyloxycarbonyl protecting group and may additionally consult T. W. Green and P. G. M. Wuts in "Protective Groups in Organic Chemistry," John Wiley and Sons, 1991 for guidance.

Once the epoxide (I) is protected, the synthesis begins with reaction of a protected epoxide (I) with a hydrazine. The hydrazine provides $R_A$ and $R_B$ that are present in the final compound (XV). For the hydrazine, $R_A$ is:

(I) —$C_1$–$C_{10}$ alkyl optionally substituted with one, two or three substituents selected from the group consisting of $C_1$–$C_3$ alkyl, —F, —Cl, —Br, —I, —OH, —SH, —C≡N, —CF$_3$, $C_1$–$C_6$ alkoxy, —O-phenyl, —NR$_{1-a}$R$_{1-b}$ where $R_{1-a}$ and $R_{1-b}$ are as defined above, —OC═O NR$_{1-a}$R$_{1-b}$ where $R_{1-a}$ and $R_{1-b}$ are as defined above, —S(═O)$_{0-2}$ R$_{1-a}$ where $R_{1-a}$ is as defined above, —NR$_{1-a}$C═O NR$_{1-a}$R$_{1-b}$ where $R_{1-a}$ and $R_{1-b}$ are as defined above, —C═O NR$_{1-a}$R$_{1-b}$ where $R_{1-a}$ and $R_{1-b}$ are as defined above, and —S(═O)$_2$ NR$_{1-a}$R$_{1-b}$ where $R_{1-a}$ and $R_{1-b}$ are as defined above, (II) —(CH$_2$)$_{0-3}$—(C$_3$–C$_8$) cycloalkyl where cycloalkyl can be optionally substituted with one, two or three substituents selected from the group consisting of $C_1$–$C_3$ alkCyl, —F, —Cl, —Br, —I, —OH, —SH, —C≡N, —CF$_3$, $C_1$–$C_6$ alkoxy, —O-phenyl, —CO—OH, —CO—O—(C$_1$–C$_4$ alkyl), and —NR$_{1-a}$R$_{1-b}$ where $R_{1-a}$ and $R_{1-b}$ are as defined above, (III) —(CR$_{A-x}$R$_{A-y}$)$_{0-4}$—R$_{A-aryl}$ where R$_{A-x}$ and R$_{A-y}$ are
  (A) —H,
  (B) $C_1$–$C_4$ alkyl optionally substituted with one or two —OH,
  (C) $C_1$–$C_4$ alkoxy optionally substituted with one, two, or three of —F,
  (D) —(CH$_2$)$_{0-4}$—$C_3$–$C_7$ cycloalkyl,
  (E) $C_2$–$C_6$ alkenyl containing one or two double bonds,
  (F) $C_2$–$C_6$ alkynyl contianing one or two triple bonds, or
  (G) phenyl,
and where R$_{A-x}$ and R$_{A-y}$ are taken together with the carbon to which they are attached to form a carbocycle of three, four, five, six or seven carbon atoms, optionally where one carbon atom is replaced by a heteroatom selected from the group consisting of —O—, —S—, —SO$_2$—, and —NR$_{N-2}$— and R$_{A-aryl}$ is the same as R$_{N-aryl}$, (IV) —(CR$_{A-x}$R$_{A-y}$)$_{0-4}$—R$_{A-heteroaryl}$ where R$_{A-heteroary}$ is the same as R$_{N-heteroayl}$ and R$_{A-x}$ and R$_{A-y}$ are as defined above, (V) —(CR$_{A-x}$R$_{A-y}$)$_{0-4}$—R$_{A-aryl}$—R$_{A-aryl}$ where R$_{A-aryl}$, R$_{A-x}$ and R$_{A-y}$ are as defined above, (VI) —(CR$_{A-x}$R$_{A-y}$)$_{0-4}$—R$_{A-aryl}$—R$_{A-heteroaryl}$ where R$_{A-aryl}$, R$_{A-heteroaryl}$, R$_{A-x}$ and R$_{A-y}$ are as defined above, (VII) —(CR$_{A-x}$R$_{A-y}$)$_{0-4}$—R$_{A-heteroaryl}$—R$_{A-aryl}$ where R$_{A-heteroaryl}$, R$_{A-aryl}$, R$_{A-x}$ and R$_{A-y}$ are as defined above, (VIII) —(CR$_{A-x}$R$_{A-y}$)$_{0-4}$—R$_{A-heteroaryl}$—R$_{A-heteroaryl}$ where R$_{A-heteroaryl}$ R$_{A-x}$ and R$_{A-y}$ are as defined above, (IX) —(CR$_{A-x}$R$_{A-y}$)$_{0-4}$—R$_{A-aryl}$—R$_{A-heterocycle}$ where R$_{A-heterocycle}$ is defined as R$_{1-heterocycle}$, and where R$_{A-aryl}$, R$_{A-x}$ and R$_{A-y}$ are as defined above, (X) —(CR$_{A-x}$R$_{A-y}$)$_{0-4}$—R$_{A-heteroaryl}$—R$_{A-heterocycle}$ where R$_{A-heteroaryl}$, R$_{A-heterocycle}$, R$_{A-x}$ and R$_{A-y}$ are as defined above, (XI) —(CR$_{A-x}$R$_{A-y}$)$_{0-4}$—R$_{A-heterocycle}$—R$_{A-aryl}$ where R$_{A-heterocycle}$, R$_{A-aryl}$, R$_{A-x}$ and R$_{A-y}$ are as defined above, (XII) —(CR$_{A-x}$R$_{A-y}$)$_{0-4}$—R$_{A-heterocycle}$—R$_{A-heteroaryl}$ where R$_{A-heterocycle}$, R$_{A-heteroaryl}$, R$_{A-x}$ and R$_{A-y}$ are as defined above, (XIII) —(CR$_{A-x}$R$_{A-y}$)$_{0-4}$—R$_{A-heterocycle}$—R$_{A-heterocycle}$ where R$_{A-heterocycle}$, R$_{A-x}$ and R$_{A-y}$ are as defined above, (XIV) —(CR$_{A-x}$R$_{A-y}$)$_{0-4}$—R$_{A-heterocycle}$ where R$_{A-heterocycle}$, R$_{A-x}$ and R$_{A-y}$ are as defined above, (XV) —[C(R$_{A-1}$)(R$_{A-2}$)]$_{1-3}$—CO—N—(R$_{A-3}$)$_2$ where R$_{A-1}$ and R$_{A-2}$ are the same or different and are selected from the group consisting of:
  (A) —H,
  (B) —$C_1$–$C_6$ alkyl, optionally substituted with one, two or three substituents selected from the group consisting of $C_1$–$C_3$ alkyl, —F, —Cl, —Br, —I, —OH, —SH, —C≡N, —CF$_3$, $C_1$–$C_6$ alkoxy, —O-phenyl, and NR$_{1-a}$R$_{1-b}$ where R$_{1-a}$ and R$_{1-b}$ are as defined above,
  (C) $C_2$–$C_6$ alkenyl with one or two double bonds, optionally substituted with one, two or three substituents selected from the group consisting of $C_1$–$C_3$ alkyl, —F, —Cl, —Br, —I, —OH, —SH, —C≡N, —CF$_3$, $C_1$–$C_6$ alkoxy, —O-phenyl, and —NR$_{1-a}$R$_{1-b}$ where R$_{1-a}$ and R$_{1-b}$ are as defined above,
  (D) $C_2$–$C_6$ alkynyl with one or two triple bonds, optionally substituted with one, two or three substituents selected from the group consisting of $C_1$–$C_3$ alkyl, —F, —Cl, —Br, —I, —OH, —SH, —C≡N, —CF$_3$, $C_1$–$C_6$ alkoxy, —O-phenyl, and —NR$_{1-a}$R$_{1-b}$ where R$_{1-a}$ and R$_{1-b}$ are as defined above,
  (E) —(CH$_2$)$_{1-2}$—S(O)$_{0-2}$—(C$_1$–C$_6$ alkyl),
  (F) —(CH$_2$)$_{0-4}$—C$_3$–C$_7$ cycloalkyl, optionally substituted with one, two or three substituents selected from the group consisting of $C_1$–$C_3$ alkyl, —F, —Cl, —Br, —I, —OH, —SH, —C≡N, —CF$_3$, $C_1$–$C_6$ alkoxy, —O-phenyl, and —NR$_{1-a}$R$_{1-b}$ where R$_{1-a}$ and R$_{1-b}$ are as defined above,
  (G) —(C$_1$–C$_4$ alkyl)-R$_{A'aryl}$ where R$_{A'aryl}$ is as defined for R$_{1-aryl}$,
  (H) —(C$_1$–C$_4$ alkyl)-R$_{A-heteroaryl}$ where R$_{A-heteroaryl}$ is as defined above,
  (I) —(C$_1$–C$_4$ alkyl)-R$_{A-heterocycle}$ where R$_{A-heterocycle}$ is as defined above,
  (J) —R$_{A-heteroaryl}$ where R$_{A-heteroaryl}$ is as defined above,
  (K) —R$_{A-heterocycle}$ where R$_{A-heterocycle}$ is as defined above, (M) —$(CH_2)_{1-4}$—$R_{A-4}$—$(CH_2)_{0-4}$—$R_{A-aryl}$ where $R_{A-4}$ is —O—, —S— or —$NR_{A-5}$— where $R_{A-5}$ is $C_1$–$C_6$ alkyl, and where $R_{A'aryl}$ is defined above, (N) —$(CH_2)_{1-4}$—$R_{A-4}$—$(CH_2)_{0-4}$—$R_{A-heteroaryl}$ where $R_{A-4}$ and $R_{A-heteroaryl}$ are as defined above, and (O) —$R_{A-aryl}$ where $R_{A-aryl}$ is as defined above, and where $R_{A-3}$ is the same or different and is:

(A) —H, (B) —$C_1$–$C_6$ alkyl optionally substituted with one, two or three substituents selected from the group consisting of $C_1$–$C_3$ alkyl, —F, —Cl, —Br, —I, —OH, —SH, —C≡N, —$CF_3$, $C_1$–$C_6$ alkoxy, —O-phenyl, $NR_{1-a}R_{1-b}$ where $R_{1-a}$ and $R_{1-b}$ are as defined above, (C) $C_2$–$C_6$ alkenyl with one or two double bonds, optionally substituted with one, two or three substituents selected from the group consisting of $C_1$–$C_3$ alkyl, —F, —Cl, —Br, —I, —OH, —SH, —C≡N, —$CF_3$, $C_1$–$C_6$ alkoxy, —O-phenyl, and $NR_{1-a}R_{1-b}$ where $R_{1-a}$ and $R_{1-b}$ are as defined above, (D) $C_2$–$C_6$ alkynyl with one or two triple bonds, optionally substituted with one, two or three substituents selected from the group consisting of $C_1$–$C_3$ alkyl, —F, —Cl, —Br, —I, —OH, —SH, —C≡N, —$CF_3$, $C_1$–$C_6$ alkoxy, —O-phenyl, and —$NR_{1-a}R_{1-b}$ where $R_{1-a}$ and $R_{1-b}$ are as defined above, (E) —$(CH_2)_{0-4}$—$C_3$–$C_7$ cycloalkyl, optionally substituted with one, two or three substituents selected from the group consisting of $C_1$–$C_3$ alkyl, —F, —Cl, —Br, —I, —OH, —SH, —C≡N, —$CF_3$, $C_1$–$C_6$ alkoxy, —O-phenyl, and —$NR_{1-a}R_{1-b}$ where $R_{1-a}$ and $R_{1-b}$ are as defined above, (F) —$R_{A'-aryl}$ where $R_{A'-aryl}$ is as defined above, (G) —$R_{A-heteroaryl}$ where $R_{A-heteroaryl}$ is as defined above, (H) —$R_{A-heterocycle}$ where $R_{A-heterocycle}$ is as defined above, (I) —($C_1$–$C_4$ alkyl)-$R_{A'aryl}$ where $R_{A'-aryl}$ is as defined above, (J) —($C_1$–$C_4$ alkyl)-$R_{A-heteroaryl}$ where $R_{A-heteroaryl}$ is as defined above, (K) —($C_1$–$C_4$ alkyl)-$R_{A-heterocycle}$ where $R_{A-heterocycle}$ is as defined above, or (XVI) —$CH(R_{A-aryl})_2$ where $R_{A-aryl}$ are the same or different and are as defined above, (XVII) —$CH(R_{A-heteroaryl})_2$ where $R_{A-heteroaryl}$ are the same or different and are as defined above, (XVIII) —$CH(R_{A-aryl})(R_{A-heteroaryl})$ where $R_{A-aryl}$ and $R_{A-heteroaryl}$ are as defined above, (XIX) -cyclopentyl, -cyclohexyl, or -cycloheptyl ring fused to $R_{A-aryl}$, $R_{A-heteroaryl}$, $R_{A-heterocycle}$ where $R_{A-aryl}$ or $R_{A-heteroaryl}$ or $R_{A-heterocycle}$ are as defined above where one carbon of cyclopentyl, cyclohexyl, or -cycloheptyl is optionally replaced with NH, $NR_{N-5}$, O, or $S(=O)_{0-2}$, and where cyclopentyl, cyclohexyl, or -cycloheptyl can be optionally substituted with one or two —$C_1$–$C_3$ alkyl, —F, —OH, —SH, —C≡N, —$CF_3$, $C_1$–$C_6$ alkoxy, =O, or —$NR_{1-a}R_{1-b}$ where $R_{1-a}$ and $R_{1-b}$ are as defined above, (XX) $C_2$–$C_{10}$ alkenyl containing one or two double bonds optionally substituted with one, two or three substituents selected from the group consisting of $C_1$–$C_3$ alkyl, —F, —Cl, —Br, —I, —OH, —SH, —C≡N, —$CF_3$, $C_1$–$C_6$ alkoxy, —O-phenyl, and —$NR_{1-a}R_{1-b}$ where $R_{1-a}$ and $R_{1-b}$ are as defined above, (XXI) $C_2$–$C_{10}$ alkynyl containing one or two triple bonds optionally substituted with one, two or three substituents selected from the group consisting of $C_1$–$C_3$ alkyl, —F, —Cl, —Br, —I, —OH, —SH, —C≡N, —$CF_3$, $C_1$–$C_6$ alkoxy, —O-phenyl, —$NR_{1-a}R_{1-b}$ where $R_{1-a}$ and $R_{1-b}$ are as defined above, (XXI) —$(CH_2)_{0-1}$—$CHR_{A-6}$—$(CH_2)_{0-1}$—$R_{A-aryl}$ where $R_{A-aryl}$ is as defined above and $R_{A-6}$ is —$(CH_2)_{0-6}$—OH, (XXII) —$CH_2)_{0-1}$—$CHR_{A-6}$—$(CH_2)_{0-1}$—$R_{A-heteroaryl}$ where $R_{A-heteroaryl}$ and $R_{A-6}$ is as defined above, (XXIII) —CH(—$R_{A-aryl}$ or $R_{A-heteroaryl}$)—CO—O($C_1$–$C_4$ alkyl) where $R_{A-aryl}$ and $R_{A-heteroaryl}$ are as defined above, (XXIV) —CH(—$CH_2$—OH)—CH(—OH)-micro-$NO_2$, (XXV) ($C_1$–$C_6$ alkyl)-O—($C_1$–$C_6$ alkyl)-OH, (XXVII) —$CH_2$—NH—$CH_2$—CH(—O—$CH_2$—$CH_3$)$_2$, (XXVIII) —H, (XXIX) —$(CH_2)_{0-6}$—C(=$NR_{1-a}$)($NR_{1-a}R_{1-b}$) where $R_{1-a}$ and $R_{1-b}$ are as defined above; or (XXX)
—C=OC($HR_6$)$NHR_7$, where $R_6$ and $R_7$ are as defined below,
—C=$OR_7$, where $R_7$ is as defined below,
—C=$OOR_7$, where $R_7$ is as defined below, or
—$SOOR_7$ where $R_7$ is as defined below,
wherein $R_6$ is:
hydrogen,
$C_1$–$C_3$ alkyl,
phenyl,
thioalkoxyalkyl,
alkyl substituted aryl,
cycloalkyl,
cycloalkylalkyl,
hydroxyalkyl,
alkoxyalkyl,
aryloxyalkyl,
haloalkyl,
carboxyalkyl,
alkoxycarbonylalkyl,
aminoalkyl,
(N-protected)aminoalkyl,
alkylaminoalkyl,
((N-protected)(alkyl)amino)alkyl,
dialkylaminoalkyl,
guanidinoalkyl,
lower alkenyl,
heterocyclic,
(heterocyclic)alkyl),
arylthioalkyl,
arylsulfonylalkyl,
(heterocyclic)thioalkyl,
(heterocyclic)sulfonylalkyl,
(heterocyclic)oxyalkyl,
arylalkoxyalkyl,
arylthioalkoxyalkyl,
arylalkylsulfonylalkyl,
(heterocyclic))alkoxyalkyl,
(heterocyclic)thioalkoxyalkyl,
(heterocyclic)alkylsulfonylalkyl,
cycloalkyloxyalkyl,
cycloalkylthioalkyl,
cycloalkylsulfonylalkyl,
cycloalkylalkoxykyl,
cycloalkylthioalkoxyalkyl,
cycloalkylalkylsulfonylalkyl,
aminocarbonyl,
alkylaminocarbonyl, dialkylaminocarbonyl,
aroylalkyl,
(heterocyclic)carbonylalkyl,
polyhydroxyalkyl,
aminocarbonylalkyl,
alkylaminocarbonylalkyl,
dialkylaminocarbonylalkyl,
aryloxyalkyl, or
alkylsulfonylalkyl,
wherein heterocyclic is pyridyl, thiazolyl, isothiazolyl, oxazolyl, isoxazolyl, furanyl, thienyl, tetrahydrofuranyl, tetrahydrothienyl and tetrahydro[2H]pyranyl and wherein the heterocycle is unsubstituted or substituted with one to three substituents independently selected from hydroxy, halo, amino, alkylamino, dialkylamino, alkoxy, polyalkoxy, haloalkyl, cycloalkyl, cycloalkylalkyl, aryl, arylalkyl, COOH, —SO$_3$H, lower alkenyl or lower alkyl;

wherein R$_7$ is:
C$_1$–C$_3$ alkyl,
phenyl,
thioalkoxyalkyl,
(aryl)alkyl,
cycloalkyl,
cycloalkylalkyl,
hydroxyalkyl,
alkoxyalkyl,
aryloxyalkyl,
haloalkyl,
carboxyalkyl,
alkoxycarbonylalkyl,
aminoalkyl,
(N-protected)aminocalkyl,
alkylaminoalkyl,
((N-protected)(alkyl)amino)alkyl,
dialkylaminoalkyl,
guanidinoalkyl,
lower alkenyl,
heterocyclic,
(heterocyclic)alkyl),
arylthioalkyl,
arylsulfonyalkyl,
(heterocyclic)thioalkyl,
(heterocyclic)sulfonylalkyl,
(heterocyclic)oxyalkyl,
arylalkoxyalkyl,
arylthioalkoxyalkyl,
arylalkylsulfonylalkyl,
(heterocyclic))alkoxyalkyl,
(heterocyclic)thioalkoxyalkyl,
(heterocyclic)alkylsulfonylalkyl,
cycloalkyloxyalkyl,
cycloalkylthioalkyl,
cycloalkylsulfonylalkyl,
cycloalkylalkoxyalkyl,
cycloalkylthioalkoxyalkyl,
cycloalkylalkylsulfonylalkyl,
aminocarbonyl,
alkylaminocarbonyl,
dialkylaminocarbonyl,
aroylalkyl,
(heterocyclic)carbonylalkyl,
polyhydroxyalkyl,
aminocarbonylalkyl,
alkylaminocarbonylalkyl,
dialkylaminocarbonylalkyl,
aryloxyalkyl, or
alkylsulfonylalkyl,
wherein heterocyclic is pyridyl, thiazolyl, isothiazolyl, oxazolyl, isoxazolyl, furanyl, thienyl, tetrahydrofuiranyl, tetrahydrothienyl and tetrahydro[2H]pyranyl and wherein the heterocycle is unsubstituted or substituted with one to three substituents independently selected from hydroxy, halo, amino, alkylamino, dialkylamino, alkoxy, polyalkoxy, haloalkyl, cycloalkyl, cycloalkylalkyl, aryl, arylalkyl, COOH, —SO$_3$H, lower alkenyl or lower alkyl.

The hydrazine also provides R$_B$ in the final compound (XV). For the hydrazine, R$_B$ is:

(I) —C$_1$–C$_{10}$ alkyl optionally substituted with one, two or three substituents selected from the group consisting of C$_1$–C$_3$ alkyl, —F, —Cl, —Br, —I, —OH, —SH, —C≡N, —CF$_3$, C$_1$–C$_6$ alkoxy, —O-phenyl, —NR$_{1-a}$R$_{1-b}$ where R$_{1-a}$ and R$_{1-b}$ are as defined above, —OC═O NR$_{1-a}$R$_{1-b}$ where R$_{1-a}$ and R$_{1-b}$ are as defined above, —S(═O)$_{0-2}$ R$_{1-a}$ where R$_{1-a}$ is as defined above, —NR$_{1-a}$C═O NR$_{1-a}$R$_{1-b}$ where R$_{1-a}$ and R$_{1-b}$ are as defined above, —C═O NR$_{1-a}$R$_{1-b}$ where R$_{1-a}$ and R$_{1-b}$ are as defined above, and —S(═O)$_2$ NR$_{1-a}$R$_{1-b}$ where R$_{1-a}$ and R$_{1-b}$ are defined above, (II) —(CH$_2$)$_{0-3}$—(C$_3$–C$_8$) cycloalkyl where cycloalkyl can be optionally substituted with one, two or three substituents selected from the group consisting of C$_1$–C$_3$ alkyl, —F, —Cl, —Br, —I, —OH, —SH, —C≡N, —CF$_3$, C$_1$–C$_6$ alkoxy, —O-phenyl, —CO—OH, —(C$_1$–C$_4$ alkyl), and —NR$_{1-a}$R$_{1-b}$ where R$_{1-a}$ and R$_{1-b}$ are as defined above, (III) —(CR$_{B-x}$R$_{B-y}$)$_{0-4}$—R$_{B-aryl}$ where R$_{B-x}$ and R$_{B-y}$ are
(A) —H,
(B) C$_1$–C$_4$ alkyl optionally substituted with one or two OH,
(C) C$_1$–C$_4$ alkoxy optionally substituted with one, two, or three of —F,
(D) —(CH$_2$)$_{0-4}$—C$_3$–C$_7$ cycloalkyl,
(E) C$_2$–C$_6$ alkenyl containing one or two double bonds,
(F) C$_2$–C$_6$ alkynyl contianing one or two triple bonds, or
(G) phenyl,
and where R$_{B-x}$ and R$_{B-y}$ are taken together with the carbon to which they are attached to form a carbocycle of three, four, five, six or seven carbon atoms, optionally where one carbon atom is replaced by a heteroatom selected from the group consisting of —O—, —S—, —SO$_2$—, and —NR$_{N-2}$ where R$_{N-2}$ is as defined above, and R$_{B-aryl}$ is the same as R$_{N-aryl}$ and is defined above (IV) —(CR$_{B-x}$R$_{B-y}$)$_{0-4}$—R$_{B-heteroaryl}$ where R$_{B-heteroaryl}$ is the same as R$_{N-heteroatyl}$, R$_{B-x}$, and R$_{B-y}$ are as defined above, (V) —(CR$_{B-x}$R$_{B-y}$)$_{0-4}$—R$_{B-aryl}$—R$_{B-aryl}$ where R$_{B-aryl}$, R$_{B-x}$, and R$_{B-y}$ are as defined above, (VI) —(CR$_{B-x}$R$_{B-y}$)$_{0-4}$—R$_{B-aryl}$—R$_{B-heteroaryl}$ where R$_{B-aryl}$, R$_{B-heteroaryl}$, R$_{B-x}$ and R$_{B-y}$ are as defined above, (VII) —(CR$_{B-x}$R$_{B-y}$)$_{0-4}$—R$_{B-heteroaryl}$—R$_{B-aryl}$ where R$_{B-heteroaryl}$, R$_{B-aryl}$, R$_{B-x}$ and R$_{B-y}$ are as defined above, (VIII) —(CR$_{B-x}$R$_{B-y}$)$_{0-4}$—R$_{B-heteroaryl}$—R$_{B-heteroaryl}$ where R$_{B-heteroaryl}$, R$_{B-x}$ and R$_{B-y}$ are as defined above, (IX) —(CR$_{B-x}$R$_{B-y}$)$_{0-4}$—R$_{B-heterocycle}$ where R$_{B-heterocycle}$ is defined as R$_{1-heterocycle}$, and where R$_{B-aryl}$, R$_{B-x}$ and R$_{B-y}$ are as defined above, (X) —$(CR_{B-x}R_{B-y})_{0-4}$—$R_{B-heteroaryl}$-$R_{B-heterocycle}$ where $R_{B-heteroaryl}$, $R_{B-heterocycle}$, $R_{B-x}$ and $R_{B-y}$ are as defined above, (XI) —$(CR_{B-x}R_{B-y})_{0-4}$—$R_{B-heterocycle}$—$R_{B-aryl}$ where $R_{B-heterocycle}$, $R_{B-aryl}$, $R_{B-x}$ and $R_{B-y}$ are as defined above, (XII) —$(CR_{B-x}R_{B-y})_{0-4}$—$R_{B-heterocycle}$—$R_{B-heteroaryl}$ where $R_{B-heterocycle}$, $R_{B-heteroaryl}$, $R_{B-x}$ and $R_{B-y}$ are as defined above, (XIII) —$(CR_{B-x}R_{B-y})_{0-4}$—$R_{B-heterocycle}$—$R_{B-heterocycle}$ where $R_{B-heterocycle}$, $R_{B-x}$ and $R_{B-y}$ are as defined above, (XIV) —$(CR_{B-x}R_{B-y})_{0-4}$—$R_{B-heterocycle}$ where $R_{B-heterocycle}$, $R_{B-x}$ and $R_{B-y}$ are as defined above, (XV) —$[C(R_{B-1})(R_{B-2})]_{1-3}$—CO—N—$(R_{B-3})_2$ where $R_{B-1}$ and $R_{B-2}$ are the same or different and are selected from the group consisting of:
- (A) —H,
- (B) —$C_1$–$C_6$ alkyl, optionally substituted with one, two or three substituents selected from the group consisting of $C_1$–$C_3$ alkyl, —F, —Cl, —Br, —I, —OH, —SH, —C≡N, —$CF_3$, $C_1$–$C_6$ alkoxy, —O-phenyl, and —$NR_{1-a}R_{1-b}$ where $R_{1-a}$ and $R_{1-b}$ are as defined above,
- (C) $C_2$–$C_6$ alkenyl with one or two double bonds, optionally substituted with one, two or three substituents selected from the group consisting of $C_1$–$C_3$ alkyl, —F, —Cl, —Br, —I, —OH, —SH, —C≡N, —$CF_3$, $C_1$–$C_6$ alkoxy, —O-phenyl, and $NR_{1-a}R_{1-b}$ where $R_{1-a}$ and $R_{1-b}$ are as defined above,
- (D) $C_2$–$C_6$ alkynyl with one or two triple bonds, optionally substituted with one, two or three substituents selected from the group consisting of $C_1$–$C_3$ alkyl, —F, —Cl, —Br, —I, —OH, —SH, —C≡N, —$CF_3$, $C_1$–$C_6$ alkoxy, —O-phenyl, and —$NR_{1-a}R_{1-b}$ where $R_{1-a}$ and $R_{1-b}$ are as defined above,
- (E) —$(CH_2)_{1-2}$—$S(O)_{0-2}$—($C_1$–$C_6$ alkyl),
- (F) —$(CH_2)_{0-4}$—$C_3$–$C_7$ cycloalkyl, optionally substituted with one, two or three substituents selected from the group consisting of $C_1$–$C_3$ alkyl, —F, —Cl, —Br, —I, —OH, —SH, —C≡N, —$CF_3$, $C_1$–$C_6$ alkoxy, —O-phenyl, and —$NR_{1-a}R_{1-b}$ where $R_{1-a}$ and $R_{1-b}$ are as defined above,
- (G) —($C_1$–$C_4$ alkyl)-$R_{B'aryl}$ where $R_{B'aryl}$ is as defined above for $R_{1-aryl}$,
- (H) —($C_1$–$C_4$alkyl)-$R_{B-heterocycle}$ where $R_{B-heteroaryl}$ is as defined above,
- (I) —($C_1$–$C_4$ alkyl)-$R_{B-heterocycle}$ where $R_{B-heterocycle}$ is as defined above,
- (J) —$R_{B-heteroaryl}$ where $R_{B-heteroaryl}$ is as defined above,
- (K) —$R_{B-heterocycle}$ where $R_{B-heterocycle}$ is as defined above,
- (M) —$(CH_2)_{1-4}$—$R_{B-4}$—$(CH_2)_{0-4}$—$R_{B'-aryl}$ where $R_{B-4}$ is —O—, —S— or —$NR_{B-5}$— where $R_{B-5}$ is $C_1$–$C_6$ alkyl, and where $R_{B'-aryl}$ is defined above,
- (N) —$(CH_2)_{1-4}$—$R_{B-4}$—$(CH_2)_{0-4}$—$R_{B-heteroaryl}$ where $R_{B-4}$ and $R_{B-heteroaryl}$ are as defined above, and
- (O) —$R_{B'-aryl}$ where $R_{B'-aryl}$ is as defined above;

and where $R_{B-3}$ is the same or different and is:
- (A) —H,
- (B) —$C_1$–$C_6$ alkyl optionally substituted with one, two or three substituents selected from the group consisting of $C_1$–$C_3$ alkyl, —F, —Cl, —Br, —I, —OH, —SH, —C≡N, —$CF_3$, $C_1$–$C_6$ alkoxy, —O-phenyl, and —$NR_{1-a}R_{1-b}$ where $R_{1-a}$ and $R_{1-b}$ are as defined above,
- (C) $C_2$–$C_6$ alkenyl with one or two double bonds, optionally substituted with one, two or three substituents selected from the group consisting of $C_1$–$C_3$ alkyl, —F, —Cl, —Br, —I, —OH, —SH, —C≡N, —$CF_3$, $C_1$–$C_6$ alkoxy, —O-phenyl, and $NR_{1-a}R_{1-b}$ where $R_{1-a}$ and $R_{1-b}$ are as defined above,
- (D) $C_2$–$C_6$ alkynyl with one or two triple bonds, optionally substituted with one, two or three substituents selected from the group consisting of $C_1$–$C_3$ alkyl, —F, —Cl, —Br, —I, —OH, —SH, —C≡N, —$CF_3$, $C_1$–$C_6$ alkoxy, —O-phenyl, and —$NR_{1-a}R_{1-b}$ where $R_{1-a}$ and $R_{1-b}$ are as defined above,
- (E) —$(CH_2)_{0-4}$—$C_3$–$C_7$ cycloalkyl, optionally substituted with one, two or three substituents selected from the group consisting of $C_1$–$C_3$ alkyl, —F, —Cl, —Br, —I, —OH, —SH, —C≡N, —$CF_3$, $C_1$–$C_6$ alkoxy, —O-phenyl, and —$NR_{1-a}R_{1-b}$ where $R_{1-a}$ and $R_{1-b}$ are as defined above,
- (F) —$R_{B'aryl}$ where $R_{B'-aryl}$ is as defined above,
- (G) —$R_{b-heteroaryl}$ where $R_{B-heteroaryl}$ is as defined above,
- (H) —$R_{B-heterocycle}$ where $R_{B-heterocycle}$ is as defined above,
- (I) —($C_1$–$C_4$alkyl)-$R_{B'-aryl}$ where $R_{B'-aryl}$ is as defined above,
- (J) —($C_1$–$C_4$alkyl)-$R_{B-heteroaryl}$ where $R_{B-heteroaryl}$ is as defined above,
- (K) —($C_1$–$C_4$alkyl)-$R_{B-heterocycle}$ where $R_{B-heterocycle}$ is as defined above, or (XVI) —$CH(R_{B-aryl})_2$ where $R_{B-aryl}$ are the same or different and are as defined above, (XVII) —$CH(R_{B-heteroaryl})_2$ where $R_{B-heteroaryl}$ are the same or different and are as defined above, (XVIII) —$CH(R_{B-aryl})(R_{B-heteroaryl})$ where $R_{B-aryl}$ and $R_{B-3}$heteroaryl are as defined above, (XIX) -cyclopentyl, -cyclohexyl, or -cycloheptyl ring fused to $R_{B-aryl}$ or $R_{B-heteroaryl}$ or $R_{B-heterocycle}$ where $R_{B-aryl}$ or $R_{B-heteroaryl}$ or $R_{B-heterocycle}$ are as defined above where one carbon of cyclopentyl, cyclohexyl, or -cycloheptyl is optionally replaced with NH, $NR_{N-5}$, O, or $S(=O)_{0-2}$, and where cyclopentyl, cyclohexyl, or -cycloheptyl can be optionally substituted with one or two —$C_1$–$C_3$ alkyl, —F, —OH, —SH, —C≡N, —$CF_3$, $C_1$–$C_6$ alkoxy, =O, or —$NR_{1-a}R_{1-b}$ where $R_{1-a}$ and $R_{1-b}$ are as defined above, (XX) $C_2$–$C_{10}$ alkenyl containing one or two double bonds optionally substituted with one, two or three substituents selected from the group consisting of $C_1$–$C_3$ alkyl, —F, —Cl, —Br, —I, —OH, —SH, —C≡N, —$CF_3$, $C_1$–$C_6$ alkoxy, —O-phenyl, and —$NR_{1-a}R_{1-b}$ where $R_{1-a}$ and $R_{1-b}$ are as defined above, (XXI) $C_2$–$C_{10}$ alkynyl containing one or two triple bonds optionally substituted with one, two or three substituents selected from the group consisting of $C_1$–$C_3$ alkyl, —F, —Cl, —Br, —I, —OH, —SH, —C≡N; —$CF_3$, $C_1$–$C_6$ alkoxy, —O-phenyl, and —$NR_{1-a}R_{1-b}$ where $R_{1-a}$ and $R_{1-b}$ are as defined above, (XXI) —$(CH_2)_{0-1}$—$CHR_{C-6}$—$(CH_2)_{0-1}$—$R_{B-aryl}$ where $R_{B-aryl}$ is as defined above and $R_{C-6}$ is —$(CH_2)_{0-6}$—OH, (XXII) —$(CH_2)_{0-1}$—$CHR_{B-6}$—$(CH_2)_{01}$-$R_{B-heteroaryl}$ where $R_{B-heteroaryl}$ and $R_{C-6}$ is as defined above, (XXIII) —CH(—$R_{B-aryl}$ or $R_{B-heteroaryl}$)—CO—O($C_1$–$C_4$ alkyl) where $R_{B-aryl}$ and $R_{B-heteroaryl}$, are as defined above, (XXIV) —CH(—$CH_2$—OH)—CH(—OH)-micro-$NO_2$, (XXV) ($C_1$–$C_6$ alkyl)-O—($C_1$–$C_6$ alkyl)-OH,
(XXVII) —$CH_2$—NH—$CH_2$—CH(—O—$CH_2$—$CH_3$)$_2$,
(XXVIII) —H, or
(XXIX) —($CH_2$)$_{0-6}$—C(=$NR_{1-a}$)($NR_{1-a}R_{1-b}$) where $R_{1-a}$ and $R_{1-b}$ are as defined above.

It is preferred that $R_A$ and $R_B$ are, independently, $C_1$–$C_8$ alkyl, ($CH_2$)$_{0-3}$—($C_3$–$C_7$) cycloalkyl, ($CR_{A-x}R_{A-y}$)$_{0-4}$—$R_{A-aryl}$, ($CR_{A-x}R_{A-y}$)$_{0-4}$—$R_{A-heteroaryl}$, ($CR_{A-x}R_{A-y}$)$_{0-4}$—$R_{A-heterocycle}$, cyclopentyl or cyclohexyl ring fused to $R_{A-aryl}$ or $R_{A-heteroaryl}$ or $R_{A-heterocycle}$. It is more preferred that —($CH_2$)$_{0-3}$—($C_3$–$C_7$) cycloalkyl, ($CR_{A-x}$ $R_{A-y}$)$_{0-4}$—$R_{A-aryl}$, ($CR_{A-x}R_{A-y}$)$_{0-4}$—$R_{A-heteroaryl}$, ($CR_{A-x}R_{A-y}$)$_{0-4}$—$R_{A-heterocycle}$, or cyclopentyl or -cyclohexyl ring fused to a $R_{A-aryl}$ or $R_{A-heteroaryl}$ or $R_{A-heterocycle}$. It is most preferred that $R_B$ is ($CR_{C-x}R_{C-y}$)$_{0-4}$—$R_{C-aryl}$, ($CR_{C-x}R_{C-y}$)$_{0-4}$—$R_{C-heteroaryl}$, cyclopentyl or -cyclohexyl ring fused to a $R_{C-aryl}$ or $R_{C-heteroaryl}$ or $R_{C-heterocycle}$.

The epoxide (I) is combined with the hydrazine in hot isopropanol resulting in the selective formation of the hydrazine (II) arising from alkylation of the unsubstituted nitrogen (M. Nakakata, *Tetrahedron Letters* 1993, 6095–6098). Monoacylation of the hydrazine —NH—NH— with benzyloxycarbonyl chloride or other acylating agent gives (III) and reduces the reactivity of this group to further acylation irrespective of which hydrazine nitrogen the first acyl group becomes attached to (B. Gisin, *Helv. Chim. Acta* 1970, vol 53, 1030–1043. S. Shinagawa, *Chem. Pharm. Bull.* 1981, vol 29, 3630–3638). Removal of the tert-butoxycarbonyl protecting group of (III) will provide the free amine (IV), which is coupled to the compound that provides $R_N$. $R_N$ is:

(I) $R_{N-1}$—$X_N$— where $X_N$ is selected from the group consisting of:
  (A) CO—,
  (B) —$SO_2$—,
  (C) —(CR'R") where R' and R" are the same or different and are —H and $C_1$–$C_4$ alkyl,
  (D) —CO—(CR'R")$_{1-6}$—$X_{N-1}$ where $X_{N-1}$ is selected from the group consisting of —O—, —S— and —NR'— and where R' and R" are as defined above, and
  (E) a single bond;

where $R_{N-1}$ is selected from the group consisting of:
  (A) $R_{N-aryl}$ where $R_{N-aryl}$ is phenyl, 1-naphthyl, 2-naphthyl, tetralinyl, indanyl, 6,7,8,9-tetrahydro-5H-benzo[a]cycloheptenyl, or dihydronaphthyl optionally substituted with one, two or three of the following substituents which can be the same or different and are:
    (1) $C_1$–$C_6$ alkyl, optionally substituted with one, two or three substituents selected from the group consisting of $C_1$–$C_3$ alkyl, —F, —Cl, —Br, —I, —OH, —SH, —C≡N, —$CF_3$, $C_1$–$C_3$ alkoxy, and —$NR_{1-a}R_{1-b}$ where $R_{1-a}$ and $R_{1-b}$ are as defined above,
    (2) —OH,
    (3) —$NO_2$,
    (4) —F, —Cl, —Br, —I,
    (5) —CO—OH,
    (6) —C≡N,
    (7) —$CH_2$)$_{0-4}$—CO—$NR_{N-2}R_{N-3}$ where $R_{N-2}$ and $R_{N-3}$ are the same or different and are selected from the group consisting of:
      (a) —H,
      (b) —$C_1$–$C_6$ alkyl optionally substituted with one substitutent selected from the group consisting of:
        (i) —OH, and
        (ii) —$NH_2$,
      (c) —$C_1$–$C_6$ alkyl optionally substituted with one, two, or three —F, —Cl, —Br, or —I,
      (d) —$C_3$–$C_7$ cycloalkyl,
      (e) —($C_1$–$C_2$ alkyl)-($C_3$–$C_7$ cycloalkyl),
      (f) —($C_1$–$C_6$ alkyl)-O—($C_1$–$C_3$ alkyl),
      (g) —$C_2$–$C_6$ alkenyl with one or two double bonds,
      (h) —$C_2$–$C_6$ alkynyl with one or two triple bonds,
      (i) —$C_1$–$C_6$ alkyl chain with one double bond and one triple bond,
      (j) —$R_{1-aryl}$ where $R_{1-aryl}$ is as defined above, and
      (k) —$R_{1-heteroaryl}$ where $R_{1-heteroaryl}$ is as defined above,
    (8) —($CH_2$)$_{0-4}$—CO—($C_1$–$C_{12}$ alkyl),
    (9) —($CH_2$)$_{0-4}$—CO—($C_2$–$C_{12}$ alkenyl with one, two or three double bonds),
    (10) —($CH_2$)$_{0-4}$—CO—($C_2$–$C_{12}$ alkynyl with one, two or three triple bonds),
    (11) —($CH_2$)$_{0-4}$—CO—($C_3$–$C_7$ cycloalkyl),
    (12) —($CH_2$)$_{0-4}$—CO—$R_{1-heteroaryl}$ where $R_{1-aryl}$ is as defined above,
    (13) —($CH_2$)$_{0-4}$—CO—$R_{1-heteroaryl}$ where $R_{1-heteroaryl}$ is as defined above,
    (14) $CH_2$)$_{0-4}$—CO—$R_{1-heterocycle}$ where $R_{1-heterocycle}$ is as defined above,
    (15) —($CH_2$)$_{0-4}$—CO—$R_{N-4}$ where $R_{N-4}$ is selected from the group consisting of morpholinyl, thiomorpholinyl, piperazinyl, piperidinyl, homomorpholinyl, homothiomorpholinyl, homothiomorpholinyl S-oxide, homothiomorpholinyl S,S-dioxide, pyrrolinyl and pyrrolidinyl where each group is optionally substituted with one, two, three, or four of $C_1$–$C_6$ alkyl,
    (16) —($CH_2$)$_{0-4}$—CO—O—$R_{N-5}$ where $R_{N-5}$ is selected from the group consisting of:
      (a) $C_1$–$C_6$ alkyl,
      (b) —($CH_2$)$_{0-2}$—($R_{1-aryl}$) where $R_{1-aryl}$ is as defined above,
      (c) $C_2$–$C_6$ alkenyl containing one or two double bonds,
      (d) $C_2$–$C_6$ alkynyl containing one or two triple bonds,
      (e) $C_3$–$C_7$ cycloalkyl, and
      (f) —($CH_2$)$_{0-2}$—($R_{1-heteroaryl}$) where $R_{1-heteroaryl}$ is as defined above,
    (17) —($CH_2$)$_{0-4}$—$SO_2$—$NR_{N-2}R_{N-3}$ where $R_{N-2}$ and $R_{N-3}$ are as defined above,
    (18) —($CH_2$)$_{0-4}$—SO—($C_1$–$C_8$ alkyl),
    (19) —($CH_2$)$_{0-4}$—$SO_2$—($C_1$–$C_{12}$ alkyl),
    (20) —($CH_2$)$_{0-4}$—$SO_2$—($C_3$–$C_7$ cycloalkyl),
    (21) —($CH_2$)$_{0-4}$—N(H or $R_{N-5}$)—CO—O—$R_{N-5}$ where $R_{N-5}$ can be the same or different and is as defined above,
    (22) —($CH_2$)$_{0-4}$—N(H or $R_{N-5}$)—CO—N($R_{N-5}$)$_2$, where $R_{N-5}$ can be the same or different and is as defined above,
    (23) —($CH_2$)0-4—N—CS—N($R_{N-5}$)$_2$, where $R_{N-5}$ can be the same or different and is as defined above,
    (24) —($CH_2$)$_{0-4}$—N(—H or $R_{N-5}$)—CO—$R_{N-2}$ where $R_{N-5}$ and $R_{N-2}$ can be the same or different and are as defined above,
    (25) —($CH_2$)$_{0-4}$—$NR_{N-2}R_{N-3}$ where $R_{N-2}$ and $R_{N-3}$ can be the same or different and are as defined above,

(26) —(CH$_2$)$_{0-4}$—R$_{N-4}$ where R$_{N-4}$ is as defined above,
(27) —(CH$_2$)$_{0-4}$—CO—(C$_1$–C$_6$ alkyl),
(28) —(CH$_2$)$_{0-4}$—O—P(O)—(OR$_{N-aryl-1}$)$_2$ where R$_{N-aryl-1}$ is —H or C$_1$–C$_4$ alkyl,
(29) —(CH$_2$)$_{0-4}$—O—CO—N(R$_{N-5}$)$_2$ where R$_{N-5}$ is as defined above,
(30) —(CH$_2$)$_{0-4}$—O—CS—N(R$_{N-5}$)$_2$ where R$_{N-5}$ is as defined above,
(31) —(CH$_2$)$_{0-4}$—O—(R$_{N-5}$)$_2$ where R$_{N-5}$ is as defined above,
(32) —(CH$_2$)$_{0-4}$—O—(R$_{N-5}$)$_2$—COOH where R$_{N-5}$ is as defined above,
(33) —(CH$_2$)$_{0-4}$—S—(R$_{N-5}$)$_2$ where R$_{N-5}$ is as defined above,
(34) —(CH$_2$)$_{0-4}$—(C$_1$–C$_6$ alkyl optionally substituted with one, two, three, four, or five of —F),
(35) C$_3$–C$_7$ cycloalkyl,
(36) C$_2$–C$_6$ alkenyl with one or two double bonds optionally substituted with C$_1$–C$_3$ alkyl, —F, —Cl, —Br, —I, —OH, —SH, —C≡N, —CF$_3$, C$_1$–C$_3$ alkoxy, or —NR$_{1-a}$R$_{1-b}$ where R$_{1-a}$ and R$_{1-b}$ are as defined above,
(37) C$_2$–C$_6$ alkynyl with one or two triple bonds optionally substituted with C$_1$–C$_3$ alkyl, —F, —Cl, —Br, —I, —OH, —SH, —C≡N, —CF$_3$, C$_1$–C$_3$ alkoxy, or —NR$_{1-a}$R$_{1-b}$ where R$_{1-a}$ and R$_{1-b}$ are as defined above,
(38) —(CH$_2$)$_{0-4}$—N(—H or R$_{N-5}$)—SO$_2$-R$_{N-2}$ where R$_{N-5}$ and R$_{N-2}$ can be the same of different and are as described above, or
(39) —(CH$_2$)$_{0-4}$—C$_3$–C$_7$ cycloalkyl,
(B) —R$_{N-heteroaryl}$ where R$_{N-heteroaryl}$ is selected from the group consisting of:
pyridinyl,
pyrimidinyl,
quinolinyl,
benzothienyl,
indolyl,
indolinyl,
pryidazinyl,
pyrazinyl,
isoindolyl,
isoquinolyl,
quinazolinyl,
quinoxalinyl,
phthalazinyl,
imidazolyl,
isoxazolyl,
pyrazolyl,
oxazolyl,
pthiazolyl,
indolizinyl,
indazolyl,
benzothiazolyl,
benzimidazolyl,
benzoftiranyl,
furanyl,
thienyl,
pyrrolyl,
oxadiazolyl,
thiadiazolyl,
triazolyl,
tetrazolyl,
oxazolopyridinyl,
imidazopyridinyl,
isothiazolyl,
naphthyridinyl,
cinnolinyl,
carbazolyl,
beta-carbolinyl,
isochromanyl,
chromanyl,
tetrahydroisoquinolinyl,
isoindolinyl,
isobenzotetrahydrofuranyl,
isobenzotetrahydrothienyl,
isobenzothienyl,
benzoxazolyl,
pyridopyridinyl,
benzotetrahydrofuranyl,
benzotetrahydrothienyl,
purinyl,
benzodioxolyl,
triazinyl,
phenoxazinyl,
phenothiazinyl,
pteridinyl,
benzothiazolyl,
imidazopyridinyl,
imidazothiazolyl,
dihydrobenzisoxazinyl,
benzisoxazinyl,
benzoxazinyl,
dihydrobenzisothiazinyl,
benzopyranyl,
benzothiopyranyl,
coumarinyl,
isocoumarinyl,
chromonyl,
chromanonyl,
pyridinyl-N-oxide,
tetrahydroquinolinyl,
dihydroquinolinyl,
dihydroquinolinonyl,
dihydroisoquinolinonyl,
dihydrocoumarinyl,
dihydroisocoumarinyl,
isoindolinonyl,
benzodioxanyl,
benzoxazolinonyl,
pyrrolyl N-oxide,
pyrimidinyl N-oxide,
pyridazinyl N-oxide,
pyrazinyl N-oxide,
quinolinyl N-oxide,
indolyl N-oxide,
indolinyl N-oxide,
isoquinolyl N-oxide,
quinazolinyl N-oxide,
quinoxalinyl N-oxide,
phthalazinyl N-oxide,
imidazolyl N-oxide,
isoxazolyl N-oxide,
oxazolyl N-oxide,
thiazolyl N-oxide,
indolizinyl N-oxide,
indazolyl N-oxide,
benzothiazolyl N-oxide,
benzimidazolyl N-oxide,
pyrrolyl N-oxide,
oxadiazolyl N-oxide,
thiadiazolyl N-oxide,
triazolyl N-oxide, tetrazolyl N-oxide,
benzothiopyranyl S-oxide, and
benzothiopyranyl S,S-dioxide
where the $R_{N\text{-}heteroaryl}$ group is bonded by any atom of the parent $R_{N\text{-}heteroaryl}$ group substituted by hydrogen such that the new bond to the $R_{N\text{-}heteroaryl}$ group replaces the hydrogen atom and its bond, where heteroaryl is optionally substituted with one, two, three, or four of:

(1) $C_1$–$C_6$ alkyl, optionally substituted with one, two or three substituents selected from the group consisting of $C_1$–$C_3$ alkyl, —F, —Cl, —Br, —I, —OH, —SH, —C≡N, —CF$_3$, $C_1$–$C_3$ alkoxy, and —NR$_{1\text{-}a}$R$_{1\text{-}b}$ where R$_{1\text{-}a}$ and R$_{1\text{-}b}$ are as defined above,
(2) —OH,
(3) —NO$_2$,
(4) —F, —Cl, —Br, or —I,
(5) —CO—OH,
(6) —C≡N,
(7) —(CH$_2$)$_{0\text{-}4}$—CO—NR$_{N\text{-}2}$R$_{N\text{-}3}$ where R$_{N\text{-}2}$ and R$_{N\text{-}3}$ are the same or different and are selected from the group consisting of:
  (a) —H,
  (b) —C$_1$–C$_6$ alkyl optionally substituted with one substitutent selected from the group consisting of:
    (i) —OH, and
    (ii) —NH$_2$,
  (c) —C$_1$–C$_6$ alkyl optionally substituted with one, two, or three —F, —Cl, —Br, —I,
  (d) —C$_3$–C$_7$ cycloalkyl,
  (e) —(C$_1$–C$_2$ alkyl)-(C$_3$–C$_7$ cycloalkyl),
  (f) —(C$_1$–C$_6$ alkyl)-O—(C$_1$–C$_3$ alkyl),
  (g) —C$_2$–C$_6$ alkenyl with one or two double bonds,
  (h) —(C$_2$–C$_6$ alkenyl with one or two triple bonds,
  (i) —C$_1$–C$_6$ alkyl chain with one double bond and one triple bond,
  (j) —R$_{1\text{-}aryl}$ where R$_{1\text{-}aryl}$ is as defined above,
  (k) —R$_{1\text{-}heteroaryl}$ where R$_{1\text{-}heteroaryl}$ is as defined above,
(8) —(CH$_2$)$_{0\text{-}4}$—CO—(C$_1$–C$_{12}$ alkyl),
(9) —(CH$_2$)$_{0\text{-}4}$—CO—(C$_2$–C$_{12}$ alkenyl with one, two or three double bonds),
(10) —(CH$_2$)$_{0\text{-}4}$—CO—(C$_2$–C$_{12}$ alkynyl with one, two or three triple bonds),
(11) —(CH$_2$)$_{0\text{-}4}$—CO—(C$_3$–C$_7$ cycloalkyl),
(12) —(CH$_2$)$_{0\text{-}4}$—CO—R$_{1\text{-}aryl}$ where R$_{1\text{-}aryl}$ is as defined above,
(13) —(CH$_2$)$_{0\text{-}4}$—CO—R$_{1\text{-}heteroaryl}$ where R$_{1\text{-}heteroaryl}$ is as defined above,
(14) —(CH$_2$)$_{0\text{-}4}$—CO—R$_{1\text{-}heterocycle}$ where R$_{1\text{-}heterocycle}$ is as defined above,
(15) —(CH$_2$)$_{0\text{-}4}$—CO—R$_{N\text{-}4}$ where R$_{N\text{-}4}$ is selected from the group consisting of morpholinyl, thiomorpholinyl, piperazinyl, piperidinyl, homomorpholinyl, homothiomorpholinyl, homothiomorpholinyl S-oxide, homothiomorpholinyl S,S-dioxide, pyrrolinyl and pyrrolidinyl where each group is optionally substituted with one, two, three, or four of C$_1$–C$_6$ alkyl,
(16) —(CH$_2$)$_{0\text{-}4}$—CO—O—R$_{N\text{-}5}$ where R$_{N\text{-}5}$ is selected from the group consisting of:
  (a) C$_1$–C$_6$ alkyl,
  (b) —(CH$_2$)$_{0\text{-}2}$—(R$_{1\text{-}aryl}$) where R$_{1\text{-}aryl}$ is as defined above,
  (c) C$_2$–C$_6$ alkenyl containing one or two double bonds,
  (d) C$_2$–C$_6$ alkynyl containing one or two triple bonds,
  (e) C$_3$–C$_7$ cycloalkyl, and
  (f) —(CH$_2$)$_{0\text{-}2}$—(R$_{1\text{-}heteroaryl}$) where R$_{1\text{-}heteroaryl}$ is as defined above,
(17) —(CH$_2$)$_{0\text{-}4}$—SO$_2$—NR$_{N\text{-}2}$R$_{N\text{-}3}$ where R$_{N\text{-}2}$ and R$_{N\text{-}3}$ are as defined above,
(18) (CH$_2$)$_{0\text{-}4}$—SO—(C$_1$–C$_8$ alkyl),
(19) —(CH$_2$)$_{0\text{-}4}$—SO$_2$—(C$_1$–C$_{12}$ alkyl),
(20) —(CH$_2$)$_{0\text{-}4}$—SO$_2$—(C$_3$–C$_7$ cycloalkyl),
(21) —(CH$_2$)$_{0\text{-}4}$—N(H or R$_{N\text{-}5}$)—CO—O—R$_{N\text{-}5}$ where R$_{N\text{-}5}$ can be the same or different and is as defined above,
(22) —(CH$_2$)$_{0\text{-}4}$—N(H or R$_{N\text{-}5}$)—CO—N(R$_{N\text{-}5}$)$_2$, where R$_{N\text{-}5}$ can be the same or different and is as defined above,
(23) —(CH$_2$)$_{0\text{-}4}$—N—CS—N(R$_{N\text{-}5}$)$_2$, where R$_{N\text{-}5}$ can be the same or different and is as defined above,
(24) —(CH$_2$)$_{0\text{-}4}$—N(—H or R$_{N\text{-}5}$)—CO—R$_{N\text{-}2}$ where R$_{N\text{-}5}$ and R$_{N\text{-}2}$ can be the same or different and are as defined above,
(25) —(CH$_2$)$_{0\text{-}4}$—NR$_{N\text{-}2}$R$_{N\text{-}3}$ where R$_{N\text{-}2}$ and R$_{N\text{-}3}$ can be the same or different and are as defined above,
(26) —(CH$_2$)$_{0\text{-}4}$—R$_{N\text{-}4}$ where R$_{N\text{-}4}$ is as defined above,
(27) —(CH$_2$)$_{0\text{-}4}$—O—CO—(C$_1$–C$_6$ alkyl),
(28) —(CH$_2$)$_{0\text{-}4}$—O—P(O)—(OR$_{N\text{-}aryl\text{-}1}$)$_2$ where R$_{N\text{-}aryl\text{-}1}$ is —H or C$_1$–C$_4$ alkyl,
(29) —(CH$_2$)$_{0\text{-}4}$—O—CO—N(R$_{N\text{-}5}$)$_2$ where R$_{N\text{-}5}$ is as defined above,
(30) —(CH$_2$)$_{0\text{-}4}$—O—CS—N(R$_{N\text{-}5}$)$_2$ where R$_{N\text{-}5}$ is as defined above,
(31) —(CH$_2$)$_{0\text{-}4}$—O—(R$_{N\text{-}5}$)$_2$ where R$_{N\text{-}5}$ is as defined above,
(32) —(CH$_2$)$_{0\text{-}4}$—O—(R$_{N\text{-}5}$)$_2$—COOH where R$_{N\text{-}5}$ is as defined above,
(33) —(CH$_2$)$_{0\text{-}4}$—S—(R$_{N\text{-}5}$)$_2$ where R$_{N\text{-}5}$ is as defined above,
(34) —(CH$_2$)$_{0\text{-}4}$—O—(C$_1$–C$_6$ alkyl optionally substituted with one, two, three, four, or five of —F),
(35) C$_3$–C$_7$ cycloalkyl,
(36) C$_2$–C$_6$ alkenyl with one or two double bonds optionally substituted with C$_1$–C$_3$ alkyl, —F, —Cl, —Br, —I, —OH, —SH, —C≡N, —CF$_3$, C$_1$–C$_3$ alkoxy, or —NR$_{1\text{-}a}$R$_{1\text{-}b}$ where R$_{1\text{-}a}$ and R$_{1\text{-}b}$ are as defined above,
(37) C$_2$–C$_6$ alkynyl with one or two triple bonds optionally substituted with C$_1$–C$_3$ alkyl, —F, —Cl, —Br, —I, —OH, —SH, —C≡N, —CF$_3$, C$_1$–C$_3$ alkoxy, or —NR$_{1\text{-}a}$R$_{1\text{-}b}$ where R$_{1\text{-}a}$ and R$_{1\text{-}b}$ are as defined above,
(38) —(CH$_2$)$_{0\text{-}4}$—N(—H or R$_{N\text{-}5}$)—SO$_2$—R$_{N\text{-}2}$ where R$_{N\text{-}5}$ and R$_{N\text{-}2}$ can be the same of different and are as defined above, or
(39) —(CH$_2$)$_{0\text{-}4}$—C$_3$–C$_7$ cycloalkyl,
(C) R$_{N\text{-}aryl}$—W—R$_{N\text{-}aryl}$, where R$_{N\text{-}aryl}$, and R$_{N\text{-}aryl}$ are as defined above,
(D) R$_{N\text{-}aryl}$—W—R$_{N\text{-}heteroaryl}$, where R$_{N\text{-}aryl}$, and R$_{N\text{-}heteroaryl}$, are as defined above,
(E) R$_{N\text{-}aryl}$—W—R$_{N\text{-}1\text{-}heterocycle}$, wherein R$_{N\text{-}1\text{-}heterocycle}$ is the same as R$_{1\text{-}heterocycle}$, and R$_{1\text{-}heterocycle}$ is as defined above
(F) R$_{N\text{-}heteroayl}$—W—R$_{N\text{-}aryl}$, where R$_{N\text{-}aryl}$, and R$_{N\text{-}heteroaryl}$, are as defined above, (G) $R_{N\text{-}heteroaryl}$—W—$R_{N\text{-}heteroaryl}$ where $R_{N\text{-}heteroaryl}$ is as defined above,
(H) $R_{N\text{-}heteroaryl}$—W—$R_{N\text{-}1\text{-}heterocycle}$, where $R_{N\text{-}heteroaryl}$, and $R_{N\text{-}1\text{-}heterocycyle}$, are as defined above,
(I) $R_{N\text{-}heterocycle}$—W—$R_{N\text{-}aryl}$ wherein $R_{N\text{-}heterocycle}$ is the same as $R_{1\text{-}heterocycle}$, and $R_{1\text{-}heterocycle}$ is as defined above, and $R_{N\text{-}aryl}$ is as defined above,
(J) $R_{N\text{-}heterocycle}$—W—$R_{N\text{-}heteroaryl}$, where $R_{N\text{-}heteroayl}$, and $R_{N\text{-}heterocycyle}$, are as defined above, and
(K) $R_{N\text{-}heterocycle}$—W—$R_{N\text{-}1\text{-}heterocycle}$, where $R_{N\text{-}heterocycyle}$, and $R_{N\text{-}1\text{-}heterocycyle}$, are as defined above,
where W is
 (5) —$(CH_2)_{0-4}$—,
 (6) —O—,
 (7) —$S(O)_{0-2}$—,
 (8) —$N(R_{N\text{-}5})$— where $R_{N\text{-}5}$ is as defined above, or
 (5) —CO—;
(II) —CO—$(C_1$–$C_{10}$ alkyl) where alkyl is optionally substituted with one three substitutents selected from the group consisting of:
(A) —OH,
(B) —$C_1$–$C_6$ alkoxy,
(C) —$C_1$–$C_6$ thioalkoxy,
(D) —CO—O—$R_{N\text{-}8}$ where $R_{N\text{-}8}$ is —H, $C_1$–$C_6$ alkyl or -phenyl,
(E) —CO—$NR_{N\text{-}2}R_{N\text{-}3}$ where $R_{N\text{-}2}$ and $R_{N\text{-}3}$ are the same or different and are as defined above,
(F) —CO—$R_{N\text{-}4}$ where $R_{N\text{-}4}$ is as defined above,
(G) —$SO_2$—$(C_1$–$C_8$ alkyl),
(H) —$SO_2$—$NR_{N\text{-}2}R_{N\text{-}3}$ where $R_{N\text{-}2}$ and $R_{N\text{-}3}$ are the same or different and are as defined above,
(I) —NH—CO—$(C_1$–$C_6$ alkyl),
(J) —NH—CO—O—$R_{N\text{-}8}$ where $R_{N\text{-}8}$ is as defined above,
(K) —$NR_{N\text{-}2}R_{N\text{-}3}$ where $R_{N\text{-}2}$ and $R_{N\text{-}3}$ are the same or different and are as defined above,
(L) —$R_{N\text{-}4}$ where $R_{N\text{-}4}$ is as defined above,
(M) —O—CO—$(C_1$–$C_6$ alkyl),
(N) —O—CO—$NR_{N\text{-}8}R_{N\text{-}8}$ where $R_{N\text{-}8}$ are the same or different and are as defined above,
(O) —O—$(C_1$–$C_5$ alkyl)-COOH,
(P) —O—$(C_1$–$C_6$ alkyl optionally substituted with one, two, or three of —F, —Cl, —Br, —I),
(Q) —NH—$SO_2$—$(C_1$–$C_6$ alkyl), and
(R) —F, or —Cl,
(III) —CO—$(C_1$–$C_6$ alkyl)-O—$(C_1$–$C_6$ alkyl) where alkyl is optionally substituted with one, two, or three of substitutents selected from the group consisting of:
(A) —OH,
(B) —$C_1$–$C_6$ alkoxy,
(C) —$C_1$–$C_6$ thioalkoxy,
(D) CO—O—$R_{N\text{-}8}$ where $R_{N\text{-}8}$ is —H, $C_1$–$C_6$ alkyl or -phenyl,
(E) —CO—$NR_{N\text{-}2}R_{N\text{-}3}$ where $R_{N\text{-}2}$ and $R_{N\text{-}3}$ are the same or different and are as defined above,
(F) —CO—$R_{N\text{-}4}$ where $R_{N\text{-}4}$ is as defined above,
(G) —$SO_2$—$(C_1$–$C_8$ alkyl),
(H) —$SO_2$—$NR_{N\text{-}2}R_{N\text{-}3}$ where $R_{N\text{-}2}$ and $R_{N\text{-}3}$ are the same or different and are as defined above,
(I) —NH—CO—$(C_1$–$C_6$ alkyl),
(J) —NH—CO—O—$R_{N\text{-}8}$ where $R_{N\text{-}8}$ is as defined above,
(K) —$NR_{N\text{-}2}R_{N\text{-}3}$ where $R_{N\text{-}2}$ and $R_{N\text{-}3}$ are the same or different and are as defined above,
(L) —$R_{N\text{-}4}$ where $R_{N\text{-}4}$ is as defined above,
(M) —O—CO—$(C_1$–$C_6$ alkyl),
(N) —O—CO—$NR_{N\text{-}8}R_{N\text{-}8}$ where $R_{N\text{-}8}$ are the same or different and are as defined above,
(O) —O—$(C_1$–$C_5$ alkyl)-COOH,
(P) —O—$(C_1$–$C_6$ alkyl optionally substituted with one, two, or three of —F, —Cl, —Br, or —I),
(Q) —NH—$SO_2$—$(C_1$–$C_6$ alkyl), and
(R) —F, or —Cl,
(IV) —CO—$(C_1$–$C_6$ alkyl)-S—$(C_1$–$C_6$ alkyl) where alkyl is optionally substituted with one, two, or three of substitutents selected from the group consisting of:
(A) —OH,
(B) —$C_1$–$C_6$ alkoxy,
(C) —$C_1$–$C_6$ thioalkoxy,
(D) —CO—O—$R_{N\text{-}8}$ where $R_{N\text{-}8}$ is as defined above,
(E) —CO—$NR_{N\text{-}2}R_{N\text{-}3}$ where $R_{N\text{-}2}$ and $R_{N\text{-}3}$ are the same or different and are as defined above,
(F) —CO—$R_{N\text{-}4}$ where $R_{N\text{-}4}$ is as defined above,
(G) —$SO_2$—$(C_1$–$C_8$ alkyl),
(H) —$SO_2$—$NR_{N\text{-}2}R_{N\text{-}3}$ where $R_{N\text{-}2}$ and $R_{N\text{-}3}$ are the same or different and are as defined above,
(I) —NH—CO—$(C_1$–$C_6$ alkyl),
(J) —NH—CO—O—$R_{N\text{-}8}$ where $R_{N\text{-}8}$ is as defined above,
(K) —$NR_{N\text{-}2}R_{N\text{-}3}$ where $R_{N\text{-}2}$ and $R_{N\text{-}3}$ are the same or different and are as defined above,
(L) —$R_{N\text{-}4}$ where $R_{N\text{-}4}$ is as defined above,
(M) —O—CO—$(C_1$–$C_6$ alkyl),
(N) —O—CO—$NR_{N\text{-}8}R_{N\text{-}8}$ where $R_{N\text{-}8}$ are the same or different and are as defined above,
(O) —O—$(C_1$–$C_5$ alkyl)-COOH,
(P) —O—$(C_1$–$C_6$ alkyl optionally substitued with one, two, or three of —F, —Cl, —Br, or —I),
(Q) —NH—$SO_2$—$(C_1$–$C_6$ alkyl), and
(R) —F, or —Cl,
(V) —CO—CH(—$(CH_2)_{0-2}$—O—$R_{N\text{-}10}$)—$(CH_2)_{0-2}$—$R_{N\text{-}aryl}/R_{N\text{-}heteroaryl}$) where $R_{N\text{-}aryl}$ and $R_{N\text{-}hetetoaryl}$ are as defined above, where $R_{N\text{-}10}$ is selected from the group consisting of:
(A) —H,
(B) $C_1$–$C_6$ alkyl,
(C) $C_3$–$C_7$ cycloalkyl,
(D) $C_2$–$C_6$ alkenyl with one double bond,
(E) $C_2$–$C_6$ alkynyl with one triple bond,
(F) $R_{1\text{-}aryl}$ where $R_{1\text{-}aryl}$ is as defined above, and
(G) $R_{N\text{-}heteroaryl}$ where $R_{N\text{-}heteroaryl}$ is as defined above, or
(VI) —CO—$(C_3$–$C_8$ cycloalkyl) where alkyl is optionally substituted with one or two substituents selected from the group consisting of:
(A) —$(CH_2)_{0-4}$—OH,
(B) —$(CH_2)_{0-4}$—$C_1$–$C_6$ alkoxy,
(C) —$(CH_2)_{0-4}$—$C_1$–$C_6$ thioalkoxy,
(D) —$(CH_2)_{0-4}$—CO—O—$R_{N\text{-}8}$ where $R_{N\text{-}8}$ is —H, $C_1$–$C_6$ alkyl or phenyl,
(E) —$(CH_2)_{0-4}$—CO—$NR_{N\text{-}2}R_{N\text{-}3}$ where $R_{N\text{-}2}$ and $R_{N\text{-}3}$ are the same or different and are as defined above,
(F) —$(CH_2)_{0-4}$—CO—$R_{N\text{-}4}$ where $R_{N\text{-}4}$ is as defined above,
(G) —$(CH_2)_{0-4}$—$SO_2$—$(C_1$–$C_8$ alkyl),
(H) —$(CH_2)_{0-4}$—$SO_2$—$NR_{N\text{-}2}R_{N\text{-}3}$ where $R_{N\text{-}2}$ and $R_{N\text{-}3}$ are the same or different and are as defined above,
(I) —$(CH_2)_{0-4}$—NH—CO—$(C_1$–$C_6$ alkyl),
(J) —NH—CO—O—$R_{N\text{-}8}$ where $R_{N\text{-}8}$ is as defined above, (K) —$(CH_2)_{0-4}$—$NR_{N-2}R_{N-3}$ where $R_{N-2}$ and $R_{N-3}$ are the same or different and are as defined above, (L) —$(CH_2)_{0-4}$—$R_{N-4}$ where $R_{N-4}$ is as defined above, (M) —O—CO—($C_1$-$C_6$ alkyl), (N) —O—CO—$NR_{N-8}R_{N-8}$ where $R_{N-8}$ are the same or different and are as defined above, (O) —O—($C_1$-$C_5$ alkyl)-COOH, (P) —O—($C_1$-$C_6$ alkyl optionally substitued with one, two, or three of —F, —Cl, —Br, or —I), (Q) —NH—$SO_2$—($C_1$-$C_6$ alkyl), and (R) —F, or —Cl.

The compound that is the source of $R_N$ can be coupled with any well known coupling agents, an example of which is carbodiimide. Cleavage of the acylhydrazine linkage gives the compounds (XV).

CHART A' gives a more specific example of one method of synthesizing compounds of the invention (XV). The anti-Alzheimer's coumpounds of formula (XV) are prepared by starting with the corresponding epoxide (I). The epoxides (I) are well known to those skilled in the art or can be readily prepared from known compounds by methods well known to those skilled in the art. The compounds of formula (XV) of the present invention have at least two enantiomeric centers which give four enantiomers. The first of these enantiomeric centers derives from the epoxide starting material (I). If a desired enantiomer is preferred, it is preferred to commercially obtain or produce the desired enantiomer (S or R) rather than produce an enantiomerically impure mixture and then have to separate out the desired enantiomer.

The exemplary synthesis begins by reacting the epoxide (I) with an armoatic hydraxine in hot isopropanol results in the selective formation of the hydrazines (II) arising from alkylation of the unsubstituted nitrogen (M. Nakakata, *Tetrahedron Letters* 1993, 6095–6098). Monoacylation of the hydrazine —NH—NH— with benzyloxycarbonyl chloride or other acylating agent gives (III) and reduces the reactivity of this group to further acylation irrespective of which hydrazine nitrogen the first acyl group becomes attached to (B. Gisin, *Helv. Chim. Acta* 1970, vol 53, 1030–1043. S. Shinagawa, *Chem. Pharm. Bull.* 1981, vol 29, 3630–3638). Removal of the tert-butoxycarbonyl protecting group of (III) will provide the free amine (IV), which is coupled to the isophthalic acid (XIV) using carbodiimide or other well known coupling agents. Cleavage of the acylhydrazine linkage gives a compound of the invention (XV).

CHART B offers another example of a method that can be utilized to make compounds of the invention. Selective acylation of methylhydrazine on the substituted nitrogen (D. Butler, *J. Medicinal Chemistry* 1971, vol. 14, 1052–1054) will provide acylhydrazine VI. Treating this hydrazide with epoxide I in hot isopropanol will provide adduct VII (S. Wang, *J. Medicinal Chemistry* 1997, vol 40, 937–941. G. Bold, *J. Medicinal Chemistry* 1998, vol 41, 3387–3401). Cleavage of the tert-butoxycarbonyl protecting group and coupling to isophthalic acid (XIV) will provide a compound of the invention (XV).

CHART C offers a general method of making compounds (XV) of the invention, wherein X is O. A general method of synthesizing compounds (XV) of the invention wherein X is O, begins with a protected epoxide (I). The epoxide (I) again serves to provide $R_1$, $R_2$, and $R_3$ of the final product (XV), the discussion of these compounds offered above applies equally here. The epoxide is opened with a hydroxylamine having the formula $R_4$—O—$NH_2$. The hydroxylamine serves both to open the epoxide ring and provide $R_4$ to the final product (XV). Once the hydroxylamine has been reacted with the epoxide (I), the adduct (XI) is formed. Adduct (XI) has $R_1$, $R_2$, $R_3$, and $R_4$ of the compounds (XV) of the invention. The possible identities of $R_1$, $R_2$, $R_3$, and $R_4$, as well as the protecting group discussed above, apply to adduct (XI) as well. The next step in the synthesis of compounds (XV) of the invention, wherein X is O is cleavage of the protecting group. The protecting groups and methods of cleaving them discussed above apply similarily to these compounds. After the protecting group has been cleaved from adduct XI, the next step involves acylation with the source of $R_N$.

CHART C' offers another more specific illustrative example of one method of making compounds (XV) of the invention, wherein X is O. Epoxide (I) opening with O-benzylhydroxylamine gives the adduct XI (S. Rosenberg, *J. Medicinal Chemistry* 1990, vol 33, 1582–1590). Cleavage of the tert-butoxycarbonyl protecting group and acylation with isophthallic acid (as prepared, for example, by the method below) provides the target compound XIII.

The preparation of isophthallic acid for use in the above synthesis can be accomplished for example, by the below synthesis, referring to CHART D below. Methyl isophthalate (1 equiv, 11.1 mmol) was dissolved in 50:50 THF:DMF (20 mL) before the addition of 1,1'carbonyldiimidazole (CDI) (1.2 equiv, 13.3 mmol) at ambient temperature. Upon addition of CDI, a color change from colorless to yellow, as well as evolution of gas ($CO_2$), was observed. After gas evolution subsided (approximately one minute or less), the amine (1.2 equiv, 13.3 mmol) dissolved in DMF and diisopropylethyl amine (1.2 equiv, 13.3 mmol) was added. After 12 hours of stirring at ambient temperature, the reaction was partitioned between saturated aqueous $NH_4Cl$ and ethyl acetate, and the aqueous layer was extracted twice more with ethyl acetate. The organic extracts were then washed with saturated aqueous solutions of $NaHCO_3$ and NaCl, and dried over anhydrous $MgSO_4$ or $NaSO_4$. Filtration of the drying agent and removal of solvents in vacuo gave the crude white solid or clear oil. Purification of these compounds ifneeded was achieved via chromatography on silica gel with 30–40% ethyl acetate in hexanes (80–90% yield).

The methyl isophthalate mono-alkyl or di-alkyl amide (1 equiv, 11.1 mmol) was then treated with $LiOH.H_2O$ (3 equiv, 33.3 mmol) in a minimum amount of 1:2:1 THF:MeOH:$H_2O$ and allowed to stir overnight at ambient temperature. After 12 hours, the solvents were removed in vacuo and subsequently partitioned between $H_2O$ and ethyl acetate. If emulsions prohibit separation of the two layers, a small amount of brine was added to aid in separation. The aqueous layer was extracted once more with ethyl acetate (to remove any unreacted starting material). The aqueous layer was then acidified with concentrated HCl until pH ≦3. The cloudy-white acidic aqueous solution thus obtained was then extracted three times with ethyl acetate. These combined organic extracts were dried over anhydrous $MgSO_4$ or $Na_2SO_4$. Filtration of the drying agent and removal of solvents in vacuo gave the crude white solid. The mono- or di-alkyl amide isophthalate was used crude in the next reaction (90–100% yield).

Compounds of the invention may contain geometric or optical isomers as well as tautomers. Thus, the invention includes all tautomers and pure geometric isomers, such as the E and Z geometric isomers, as well as mixtures thereof. Furthermore, the invention includes pure enantiomers and diasteriomers as well as mixtures thereof, including racemic mixtures. The individual geometric isomers, enantiomers, or diastereomers may be prepared or isolated by methods known in the art.

Compounds of the invention with the stereochemistry designated in formula XV may be included in mixtures, including racemic mixtures, with other enantiomers, diastereomers, geometric isomers or tautomers. Compounds of the invention with the stereochemistry designated in formula XV are typically present in these mixtures in excess of 50 percent. Preferably, compounds of the invention with the stereochemistry designated in formula XV are present in these mixtures in excess of 80 percent. Most preferably, compounds of the invention with the stereochemistry designated in formula XV are present in these mixtures in excess of 90 percent.

The (S,R)-substituted amines (XV) are amines and as such form salts when reacted with acids. Pharmaceutically acceptable salts are preferred over the corresponding (S,R)-substituted amines (XV) since they produce compounds which are more water soluble, stable and/or more crystalline.

Pharmaceutically acceptable salts are any salt which retains the activity of the parent compound and does not impart any deleterious or undesirable effect on the subject to whom it is administered and in the context in which it is administered. Pharmaceutically acceptable salts include salts of both inorganic and organic acids. The preferred pharmaceutically acceptable salts include salts of the following acids acetic, aspartic, benzenesulfonic, benzoic, bicarbonic, bisulfuric, bitartaric, butyric, calcium edetate, camsylic, carbonic, chlorobenzoic, citric, edetic, edisylic, estolic, esyl, esylic, formic, fumaric, gluceptic, gluconic, glutamic, glycollylarsanilic, hexamic, hexylresorcinoic, hydrabamic, hydrobromic, hydrochloric, hydroiodic, hydroxynaphthoic, isethionic, lactic, lactobionic, maleic, malic, malonic, mandelic, methanesulfonic, methylnitric, methylsulfuric, mucic, muconic, napsylic, nitric, oxalic, p-nitromethanesulfonic, pamoic, pantothenic, phosphoric, monohydrogen phosphoric, dihydrogen phosphoric, phthalic, polygalactouronic, propionic, salicylic, stearic, succinic, succinic, sulfamic, sulfanilic, sulfonic, sulfuric, tannic, tartaric, teoclic and toluenesulfonic. For other acceptable salts, see *Int. J. Pharm.*, 33, 201–217 (1986) and *J.Pharm. Sci.*, 66(1), 1, (1977).

The present invention provides compounds, compositions, kits, and methods for inhibiting beta-secretase enzyme activity and A beta peptide production. Inhibition of beta-secretase enzyme activity halts or reduces the production of A beta from APP and reduces or eliminates the formation of beta-amyloid deposits in the brain.

Methods of the Invention

The compounds employed in the methods of the invention, and pharmaceutically acceptable salts thereof, are useful for treating humans or animals suffering from a condition characterized by a pathological form of beta-amyloid peptide, such as beta-amyloid plaques, and for helping to prevent or delay the onset of such a condition. For example, the compounds are useful for treating Alzheimer's disease, for helping prevent or delay the onset of Alzheimer's disease, for treating patients with MCI (mild cognitive impairment) and preventing or delaying the onset of Alzheimer's disease in those who would progress from MCI to AD, for treating Down's syndrome, for treating humans who have Hereditary Cerebral Hemorrhage with Amyloidosis of the Dutch-Type, for treating cerebral amyloid angiopathy and preventing its potential consequences, i.e. single and recurrent lobal hemorrhages, for treating other degenerative dementias, including dementias of mixed vascular and degenerative origin, dementia associated with Parkinson's disease, dementia associated with progressive supranuclear palsy, dementia associated with cortical basal degeneration, and diffuse Lewy body type Alzheimer's disease. The compounds and compositions of the invention are particularly useful for treating or preventing Alzheimer's disease. When treating or preventing these diseases, the compounds employed in the methods of the invention can either be used individually or in combination, as is best for the patient.

As used herein, the term "treating" means that the compounds employed in the methods of the invention can be used in humans with at least a tentative diagnosis of disease. The compounds employed in the methods of the invention will delay or slow the progression of the disease thereby giving the individual a more useful life span.

The term "preventing" means that the compounds employed in the method of the invention are useful when administered to a patient who has not been diagnosed as possibly having the disease at the time of administration, but who would normally be expected to develop the disease or be at increased risk for the disease. The compounds employed in the methods of the invention will slow the development of disease symptoms, delay the onset of the disease, or prevent the individual from developing the disease at all. Preventing also includes administration of the compounds employed in the methods of the invention to those individuals thought to be predisposed to the disease due to age, familial history, genetic or chromosomal abnormalities, and/or due to the presence of one or more biological markers for the disease, such as a known genetic mutation of APP or APP cleavage products in brain tissues or fluids.

In treating or preventing the above diseases, the compounds employed in the methods of the invention are administered in a therapeutically effective amount. The therapeutically effective amount will vary depending on the particular compound used and the route of administration, as is known to those skilled in the art.

In treating a patient displaying any of the diagnosed above conditions a physician may administer a compound employed in the method of the invention immediately and continue administration indefinitely, as needed. In treating patients who are not diagnosed as having Alzheimer's disease, but who are believed to be at substantial risk for Alzheimer's disease, the physician should preferably start treatment when the patient first experiences early pre-Alzheimer's symptoms such as, memory or cognitive problems associated with aging. In addition, there are some patients who may be determined to be at risk for developing Alzheimer's through the detection of a genetic marker such as APOE4 or other biological indicators that are predictive for Alzheimer's disease. In these situations, even though the patient does not have symptoms of the disease, administration of the compounds employed in the methods of the invention may be started before symptoms appear, and treatment may be continued indefinitely to prevent or delay the onset of the disease.

Dosage Forms and Amounts

The compounds employed in the methods of the invention can be administered orally, parenterally, (IV, IM, depo-IM, SQ, and depo SQ), sublingually, intranasally (inhalation), intrathecally, topically, or rectally. Dosage forms known to those of skill in the art are suitable for delivery of the compounds employed in the methods of the invention.

Compositions are provided that contain therapeutically effective amounts of the compounds employed in the methods of the invention. The compounds are preferably formulated into suitable pharmaceutical preparations such as tablets, capsules, or elixirs for oral administration or in sterile solutions or suspensions for parenteral administration. Typically the compounds described above are formulated into pharmaceutical compositions using techniques and procedures well known in the art.

About 1 to 500 mg of a compound or mixture of compounds employed in the methods of the invention or a physiologically acceptable salt or ester is compounded with a physiologically acceptable vehicle, carrier, excipient, binder, preservative, stabilizer, flavor, etc., in a unit dosage form as called for by accepted pharmaceutical practice. The amount of active substance in those compositions or preparations is such that a suitable dosage in the range indicated is obtained. The compositions are preferably formulated in a unit dosage form, each dosage containing from about 2 to about 100 mg, more preferably about 10 to about 30 mg of the active ingredient. The term "unit dosage from" refers to physically discrete units suitable as unitary dosages for human subjects and other mammals, each unit containing a predetermined quantity of active material calculated to produce the desired therapeutic effect, in association with a suitable pharmaceutical excipient.

To prepare compositions, one or more compounds employed in the methods of the invention are mixed with a suitable pharmaceutically acceptable carrier. Upon mixing or addition of the compound(s), the resulting mixture may be a solution, suspension, emulsion, or the like. Liposomal suspensions may also be suitable as pharmaceutically acceptable carriers. These may be prepared according to methods known to those skilled in the art. The form of the resulting mixture depends upon a number of factors, including the intended mode of administration and the solubility of the compound in the selected carrier or vehicle. The effective concentration is sufficient for lessening or ameliorating at least one symptom of the disease, disorder, or condition treated and may be empirically determined.

Pharmaceutical carriers or vehicles suitable for administration of the compounds provided herein include any such carriers known to those skilled in the art to be suitable for the particular mode of administration. In addition, the active materials can also be mixed with other active materials that do not impair the desired action, or with materials that supplement the desired action, or have another action. The compounds may be formulated as the sole pharmaceutically active ingredient in the composition or may be combined with other active ingredients.

Where the compounds exhibit insufficient solubility, methods for solubilizing may be used. Such methods are known and include, but are not limited to, using cosolvents such as dimethylsulfoxide (DMSO), using surfactants such as Tween®, and dissolution in aqueous sodium bicarbonate. Derivatives of the compounds, such as salts or prodrugs may also be used in formulating effective pharmaceutical compositions.

The concentration of the compound is effective for delivery of an amount upon administration that lessens or ameliorates at least one symptom of the disorder for which the compound is administered. Typically, the compositions are formulated for single dosage administration.

The compounds employed in the methods of the invention may be prepared with carriers that protect them against rapid elimination from the body, such as time-release formulations or coatings. Such carriers include controlled release formulations, such as, but not limited to, microencapsulated delivery systems. The active compound is included in the pharmaceutically acceptable carrier in an amount sufficient to exert a therapeutically useful effect in the absence of undesirable side effects on the patient treated. The therapeutically effective concentration may be determined empirically by testing the compounds in known in vitro and in vivo model systems for the treated disorder.

The compounds and compositions of the invention can be enclosed in multiple or single dose containers. The enclosed compounds and compositions can be provided in kits, for example, including component parts that can be assembled for use. For example, a compound inhibitor in lyophilized form and a suitable diluent may be provided as separated components for combination prior to use. A kit may include a compound inhibitor and a second therapeutic agent for co-administration. The inhibitor and second therapeutic agent may be provided as separate component parts. A kit may include a plurality of containers, each container holding one or more unit dose of the compound employed in the method of the invention. The containers are preferably adapted for the desired mode of administration, including, but not limited to tablets, gel capsules, sustained-release capsules, and the like for oral administration; depot products, pre-filled syringes, ampoules, vials, and the like for parenteral administration; and patches, medipads, creams, and the like for topical administration.

The concentration of active compound in the drug composition will depend on absorption, inactivation, and excretion rates of the active compound, the dosage schedule, and amount administered as well as other factors known to those of skill in the art.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

If oral administration is desired, the compound should be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

Oral compositions will generally include an inert diluent or an edible carrier and may be compressed into tablets or enclosed in gelatin capsules. For the purpose of oral therapeutic administration, the active compound or compounds can be incorporated with excipients and used in the form of tablets, capsules, or troches. Pharmaceutically compatible binding agents and adjuvant materials can be included as part of the composition.

The tablets, pills, capsules, troches, and the like can contain any of the following ingredients or compounds of a similar nature: a binder such as, but not limited to, gum tragacanth, acacia, corn starch, or gelatin; an excipient such as microcrystalline cellulose, starch, or lactose; a disintegrating agent such as, but not limited to, alginic acid and corn starch; a lubricant such as, but not limited to, magnesium stearate; a gildant, such as, but not limited to, colloidal silicon dioxide; a sweetening agent such as sucrose or saccharin; and a flavoring agent such as peppermint, methyl salicylate, or fruit flavoring.

When the dosage unit form is a capsule, it can contain, in addition to material of the above type, a liquid carrier such as a fatty oil. In addition, dosage unit forms can contain various other materials, which modify the physical fonn of the dosage unit, for example, coatings of sugar and other enteric agents. The compounds can also be administered as a component of an elixir, suspension, syrup, wafer, chewing gum or the like. A syrup may contain, in addition to the active compounds, sucrose as a sweetening agent and certain preservatives, dyes and colorings, and flavors.

The active materials can also be mixed with other active materials that do not impair the desired action, or with materials that supplement the desired action.

Solutions or suspensions used for parenteral, intradermal, subcutaneous, or topical application can include any of the following components: a sterile diluent such as water for injection, saline solution, fixed oil, a naturally occurring vegetable oil such as sesame oil, coconut oil, peanut oil, cottonseed oil, and the like, or a synthetic fatty vehicle such as ethyl oleate, and the like, polyethylene glycol, glycerine, propylene glycol, or other synthetic solvent; antimicrobial agents such as benzyl alcohol and methyl parabens; antioxidants such as ascorbic acid and sodium bisulfite; chelating agents such as ethylenediaminetetraacetic acid (EDTA); buffers such as acetates, citrates, and phosphates; and agents for the adjustment of tonicity such as sodium chloride and dextrose. Parenteral preparations can be enclosed in ampoules, disposable syringes, or multiple dose vials made of glass, plastic, or other suitable material. Buffers, preservatives, antioxidants, and the like can be incorporated as required.

Where administered intravenously, suitable carriers include physiological saline, phosphate buffered saline (PBS), and solutions containing thickening and solubilizing agents such as glucose, polyethylene glycol, polypropyleneglycol, and mixtures thereof. Liposomal suspensions including tissue-targeted liposomes may also be suitable as pharmaceutically acceptable carriers. These may be prepared according to methods known for example, as described in U.S. Pat. No. 4,522,811.

The active compounds may be prepared with carriers that protect the compound against rapid elimination from the body, such as time-release formulations or coatings. Such carriers include controlled release formulations, such as, but not limited to, implants and microencapsulated delivery systems, and biodegradable, biocompatible polymers such as collagen, ethylene vinyl acetate, polyanhydrides, polyglycolic acid, polyorthoesters, polylactic acid, and the like. Methods for preparation of such formulations are known to those skilled in the art.

The compounds employed in the methods of the invention can be administered orally, parenterally (IV, IM, depo-IM, SQ, and depo-SQ), sublingually, intranasally (inhalation), intrathecally, topically, or rectally. Dosage forms known to those skilled in the art are suitable for delivery of the compounds employed in the methods of the invention.

Compounds employed in the methods of the invention may be administered enterally or parenterally. When administered orally, compounds employed in the methods of the invention can be administered in usual dosage forms for oral administration as is well known to those skilled in the art. These dosage forms include the usual solid unit dosage forms of tablets and capsules as well as liquid dosage forms such as solutions, suspensions, and elixirs. When the solid dosage forms are used, it is preferred that they be of the sustained release type so that the compounds employed in the methods of the invention need to be administered only once or twice daily.

The oral dosage forms are administered to the patient 1, 2, 3, or 4 times daily. It is preferred that the compounds employed in the methods of the invention be administered either three or fewer times, more preferably once or twice daily. Hence, it is preferred that the compounds employed in the methods of the invention be administered in oral dosage form. It is preferred that whatever oral dosage form is used, that it be designed so as to protect the compounds employed in the methods of the invention from the acidic environment of the stomach. Enteric coated tablets are well known to those skilled in the art. In addition, capsules filled with small spheres each coated to protect from the acidic stomach, are also well known to those skilled in the art.

When administered orally, an administered amount therapeutically effective to inhibit beta-secretase activity, to inhibit A beta production, to inhibit A beta deposition, or to treat or prevent AD is from about 0.1 mg/day to about 1,000 mg/day. It is preferred that the oral dosage is from about 1 mg/day to about 100 mg/day. It is more preferred that the oral dosage is from about 5 mg/day to about 50 mg/day. It is understood that while a patient may be started at one dose, that dose may be varied over time as the patient's condition changes.

Compounds employed in the methods of the invention may also be advantageously delivered in a nano crystal dispersion formulation. Preparation of such formulations is described, for example, in U.S. Pat. No. 5,145,684. Nano crystalline dispersions of HIV protease inhibitors and their method of use are described in U.S. Pat. No. 6,045,829. The nano crystalline formulations typically afford greater bioavailability of drug compounds.

The compounds employed in the methods of the invention can be administered parenterally, for example, by IV, IM, depo-IM, SC, or depo-SC. When administered parenterally, a therapeutically effective amount of about 0.5 to about 100 mg/day, preferably from about 5 to about 50 mg daily should be delivered. When a depot formulation is used for injection once a month or once every two weeks, the dose should be about 0.5 mg/day to about 50 mg/day, or a monthly dose of from about 15 mg to about 1,500 mg. In part because of the forgetfulness of the patients with Alzheimer's disease, it is preferred that the parenteral dosage form be a depo formulation.

The compounds employed in the methods of the invention can be administered sublingually. When given sublingually, the compounds employed in the methods of the invention should be given one to four times daily in the amounts described above for IM administration.

The compounds employed in the methods of the invention can be administered intranasally. When given by this route, the appropriate dosage forms are a nasal spray or dry powder, as is known to those skilled in the art. The dosage of the compounds employed in the methods of the invention for intranasal administration is the amount described above for IM administration.

The compounds employed in the methods of the invention can be administered intrathecally. When given by this route the appropriate dosage form can be a parenteral dosage form as is known to those skilled in the art. The dosage of the compounds employed in the methods of the invention for intrathecal administration is the amount described above for IM administration.

The compounds employed in the methods of the invention can be administered topically. When given by this route, the appropriate dosage form is a cream, ointment, or patch. Because of the amount of the compounds employed in the methods of the invention to be administered, the patch is preferred. When administered topically, the dosage is from about 0.5 mg/day to about 200 mg/day. Because the amount that can be delivered by a patch is limited, two or more patches may be used. The number and size of the patch is not important, what is important is that a therapeutically effective amount of the compounds employed in the methods of the invention be delivered as is known to those skilled in the art. The compounds employed in the methods of the invention can be administered rectally by suppository as is known to those skilled in the art. When administered by suppository, the therapeutically effective amount is from about 0.5 mg to about 500 mg.

The compounds employed in the methods of the invention can be administered by implants as is known to those skilled in the art. When administering a compound employed in the method of the invention by implant, the therapeutically effective amount is the amount described above for depot administration.

The invention here is the new compounds employed in the methods of the invention and new methods of using the compounds employed in the methods of the invention. Given a particular compound employed in the method of the invention and a desired dosage form, one skilled in the art would know how to prepare and administer the appropriate dosage form.

The compounds employed in the methods of the invention are used in the same manner, by the same routes of administration, using the same pharmaceutical dosage forms, and at the same dosing schedule as described above, for preventing disease or treating patients with MCI (mild cognitive impairment) and preventing or delaying the onset of Alzheimer's disease in those who would progress from MCI to AD, for treating or preventing Down's syndrome, for treating humans who have Hereditary Cerebral Hemorrhage with Amyloidosis of the Dutch-Type, for treating cerebral amyloid angiopathy and preventing its potential consequences, i.e. single and recurrent lobar hemorrhages, for treating other degenerative dementias, including dementias of mixed vascular and degenerative origin, dementia associated with Parkinson's disease, dementia associated with progressive supranuclear palsy, dementia associated with cortical basal degeneration, and diffluse Lewy body type of Alzheimer's disease.

The compounds employed in the methods of the invention can be used in combination, with each other or with other therapeutic agents or approaches used to treat or prevent the conditions listed above. Such agents or approaches include: acetylcholine esterase inhibitors such as tacrine (tetrahydroaminoacridine, marketed as COGNEX®), donepezil hydrochloride, (marketed as Aricept® and rivastigmine (marketed as Exelon®); gamma-secretase inhibitors; anti-inflammatory agents such as cyclooxygenase II inhibitors; anti-oxidants such as Vitamin E and ginkolides; immunological approaches, such as, for example, immunization with A beta peptide or administration of anti-A beta peptide antibodies; statins; and direct or indirect neurotropic agents such as Cerebrolysin®, AIT-082 (Emilieu, 2000, *Arch. Neurol.* 57:454), and other neurotropic agents of the future.

It should be apparent to one skilled in the art that the exact dosage and frequency of administration will depend on the particular compounds employed in the methods of the invention administered, the particular condition being treated, the severity of the condition being treated, the age, weight, general physical condition of the particular patient, and other medication the individual may be taking as is well known to administering physicians who are skilled in this art.

Inhibition of APP Cleavage

The compounds employed in the methods of the invention inhibit cleavage of APP between Met595 and Asp596 numbered for the APP695 isoform, or a mutant thereof, or at a corresponding site of a different isoform, such as APP751 or APP770, or a mutant thereof (sometimes referred to as the "beta secretase site"). While not wishing to be bound by a particular theory, inhibition of beta-secretase activity is thought to inhibit production of beta amyloid peptide (A beta). Inhibitory activity is demonstrated in one of a variety of inhibition assays, whereby cleavage of an APP substrate in the presence of a beta-secretase enzyme is analyzed in the presence of the inhibitory compound, under conditions normally sufficient to result in cleavage at the beta-secretase cleavage site. Reduction of APP cleavage at the beta-secretase cleavage site compared with an untreated or inactive control is correlated with inhibitory activity. Assay systems that can be used to demonstrate efficacy of the compound inhibitors of the invention are known. Representative assay systems are described, for example, in U.S. Pat. Nos. 5,942,400, 5,744,346, as well as in the Examples below.

The enzymatic activity of beta-secretase and the production of A beta can be analyzed in vitro or in vivo, using natural, mutated, and/or synthetic APP substrates, natural, mutated, and/or synthetic enzyme, and the test compound. The analysis may involve primary or secondary cells expressing native, mutant, and/or synthetic APP and enzyme, animal models expressing native APP and enzyme, or may utilize transgenic animal models expressing the substrate and enzyme. Detection of enzymatic activity can be by analysis of one or more of the cleavage products, for example, by immunoassay, fluorometric or chromogenic assay, HPLC, or other means of detection. Inhibitory compounds are determined as those having the ability to decrease the amount of beta-secretase cleavage product produced in comparison to a control, where beta-secretase mediated cleavage in the reaction system is observed and measured in the absence of inhibitory compounds.

Beta-Secretase

Various forms of beta-secretase enzyme are known, and are available and useful for assay of enzyme activity and inhibition of enzyme activity. These include native, recombinant, and synthetic forms of the enzyme. Human beta-secretase is known as Beta Site APP Cleaving Enzyme (BACE), Asp2, and memapsin 2, and has been characterized, for example, in U.S. Pat. No. 5,744,346 and published PCT patent applications WO98/22597, WO00/03819, WO01/23533, and WO00/17369, as well as in literature publications (Hussain et al., 1999, *Mol. Cell. Neurosci.* 14:419–427; Vassar et al., 1999, *Science* 286:735–741; Yan et al., 1999, *Nature* 402:533–537; Sinha et al., 1999, *Nature* 40:537–540; and Lin et al., 2000, *PNAS USA* 97:1456–1460). Synthetic forms of the enzyme have also been described (WO98/22597 and WO00/17369). Beta-secretase can be extracted and purified from human brain tissue and can be produced in cells, for example mammalian cells expressing recombinant enzyme.

Useful inhibitory compounds are effective to inhibit 50% of beta-secretase enzymatic activity at a concentration of less than 50 micromolar, preferably at a concentration of 10 micromolar or less, more preferably 1 micromolar or less, and most preferably 10 nanomolar or less.

APP Substrate

Assays that demonstrate inhibition of beta-secretase-mediated cleavage of APP can utilize any of the known forms of APP, including the 695 amino acid "normal"

isotype described by Kang et al., 1987, *Nature* 325:733–6, the 770 amino acid isotype described by Kitaguchi et. al., 1981, *Nature* 331:530–532, and variants such as the Swedish Mutation (KM670-1NL) (APP-SW), the London Mutation (V7176F), and others. See, for example, U.S. Pat. No. 5,766,846 and also Hardy, 1992, *Nature Genet.* 1:233–234, for a review of known variant mutations. Additional useful substrates include the dibasic amino acid modification, APP-KK disclosed, for example, in WO 00/17369, fragments of APP, and synthetic peptides containing the beta-secretase cleavage site, wild type (WT) or mutated form, e.g., SW, as described, for example, in U.S. Pat. No. 5,942,400 and WO00/03819.

The APP substrate contains the beta-secretase cleavage site of APP (KM-DA or NL-DA) for example, a complete APP peptide or variant, an APP fragment, a recombinant or synthetic APP, or a fusion peptide. Preferably, the fusion peptide includes the beta-secretase cleavage site fused to a peptide having a moiety useful for enzymatic assay, for example, having isolation and/or detection properties. A useful moiety may be an antigenic epitope for antibody binding, a label or other detection moiety, a binding substrate, and the like.

Antibodies

Products characteristic of APP cleavage can be measured by immunoassay using various antibodies, as described, for example, in Pirttila et al., 1999, *Neuro. Lett.* 249:21–4, and in U.S. Pat. No. 5,612,486. Useful antibodies to detect A beta include, for example, the monoclonal antibody 6E10 (Senetek, St. Louis, Mo.) that specifically recognizes an epitope on amino acids 1–16 of the A beta peptide; antibodies 162 and 164 (New York State Institute for Basic Research, Staten Island, N.Y.) that are specific for human A beta 1–40 and 1–42, respectively; and antibodies that recognize the junction region of beta-amyloid peptide, the site between residues 16 and 17, as described in U.S. Pat. No. 5,593,846. Antibodies raised against a synthetic peptide of residues 591 to 596 of APP and SW192 antibody raised against 590–596 of the Swedish mutation are also useful in immunoassay of APP and its cleavage products, as described in U.S. Pat. Nos. 5,604,102 and 5,721,130.

Assay Systems

Assays for determining APP cleavage at the beta-secretase cleavage site are well known in the art. Exemplary assays, are described, for example, in U.S. Pat. Nos. 5,744, 346 and 5,942,400, and described in the Examples below.

Cell Free Assays

Exemplary assays that can be used to demonstrate the inhibitory activity of the compounds employed in the methods of the invention are described, for example, in WO00/ 17369, WO 00/03819, and U.S. Pat Nos. 5,942,400 and 5,744,346. Such assays can be performed in cell-free incubations or in cellular incubations using cells expressing a beta-secretase and an APP substrate having a beta-secretase cleavage site.

An APP substrate containing the beta-secretase cleavage site of APP, for example, a complete APP or variant, an APP fragment, or a recombinant or synthetic APP substrate containing the amino acid sequence: KM-DA or NL-DA, is incubated in the presence of beta-secretase enzyme, a fragment thereof, or a synthetic or recombinant polypeptide variant having beta-secretase activity and effective to cleave the beta-secretase cleavage site of APP, under incubation conditions suitable for the cleavage activity of the enzyme. Suitable substrates optionally include derivatives that may be fusion proteins or peptides that contain the substrate peptide and a modification useful to facilitate the purification or detection of the peptide or its beta-secretase cleavage products. Useful modifications include the insertion of a known antigenic epitope for antibody binding; the linking of a label or detectable moiety, the linking of a binding substrate, and the like.

Suitable incubation conditions for a cell-free in vitro assay include, for example: approximately 200 nanomolar to 10 micromolar substrate, approximately 10 to 200 picomolar enzyme, and approximately 0.1 nanomolar to 10 micromolar inhibitor compound, in aqueous solution, at an approximate pH of 4–7, at approximately 37 degrees C., for a time period of approximately 10 minutes to 3 hours. These incubation conditions are exemplary only, and can be varied as required for the particular assay components and/or desired measurement system. Optimization of the incubation conditions for the particular assay components should account for the specific beta-secretase enzyme used and its pH optimum, any additional enzymes and/or markers that might be used in the assay, and the like. Such optimization is routine and will not require undue experimentation.

One useful assay utilizes a fusion peptide having maltose binding protein (MBP) fused to the C-terminal 125 amino acids of APP-SW. The MBP portion is captured on an assay substrate by anti-MBP capture antibody. Incubation of the captured fusion protein in the presence of beta-secretase results in cleavage of the substrate at the beta-secretase cleavage site. Analysis of the cleavage activity can be, for example, by immunoassay of cleavage products. One such immunoassay detects a unique epitope exposed at the carboxy terminus of the cleaved fusion protein, for example, using the antibody SW192. This assay is described, for example, in U.S. Pat. No. 5,942,400.

Cellular Assay

Numerous cell-based assays can be used to analyze beta-secretase activity and/or processing of APP to release A beta. Contact of an APP substrate with a beta-secretase enzyme within the cell and in the presence or absence of a compound inhibitor of the invention can be used to demonstrate beta-secretase inhibitory activity of the compound. Preferably, assay in the presence of a useful inhibitory compound provides at least about 30%, most preferably at least about 50% inhibition of the enzymatic activity, as compared with a non-inhibited control.

In one embodiment, cells that naturally express beta-secretase are used. Alternatively, cells are modified to express a recombinant beta-secretase or synthetic variant enzyme as discussed above. The APP substrate may be added to the culture medium and is preferably expressed in the cells. Cells that naturally express APP, variant or mutant forms of APP, or cells transformed to express an isoform of APP, mutant or variant APP, recombinant or synthetic APP, APP fragment, or synthetic APP peptide or fusion protein containing the beta-secretase APP cleavage site can be used, provided that the expressed APP is permitted to contact the enzyme and enzymatic cleavage activity can be analyzed.

Human cell lines that normally process A beta from APP provide a useful means to assay inhibitory activities of the compounds employed in the methods of the invention. Production and release of A beta and/or other cleavage products into the culture medium can be measured, for example by immunoassay, such as Western blot or enzyme-linked immunoassay (EIA) such as by ELISA.

Cells expressing an APP substrate and an active beta-secretase can be incubated in the presence of a compound inhibitor to demonstrate inhibition of enzymatic activity as compared with a control. Activity of beta-secretase can be measured by analysis of one or more cleavage products of the APP substrate. For example, inhibition of beta-secretase activity against the substrate APP would be expected to decrease release of specific beta-secretase induced APP cleavage products such as A beta.

Although both neural and non-neural cells process and release A beta, levels of endogenous beta-secretase activity are low and often difficult to detect by EIA. The use of cell types known to have enhanced beta-secretase activity, enhanced processing of APP to A beta, and/or enhanced production of A beta are therefore preferred. For example, transfection of cells with the Swedish Mutant form of APP (APP-SW); with APP-KK; or with APP-SW-KK provides cells having enhanced beta-secretase activity and producing amounts of A beta that can be readily measured.

In such assays, for example, the cells expressing APP and beta-secretase are incubated in a culture medium under conditions suitable for beta-secretase enzymatic activity at its cleavage site on the APP substrate. On exposure of the cells to the compound inhibitor, the amount of A beta released into the medium and/or the amount of CTF99 fragments of APP in the cell lysates is reduced as compared with the control. The cleavage products of APP can be analyzed, for example, by immune reactions with specific antibodies, as discussed above.

Preferred cells for analysis of beta-secretase activity include primary human neuronal cells, primary transgenic animal neuronal cells where the transgene is APP, and other cells such as those of a stable 293 cell line expressing APP, for example, APP-SW.

In vivo Assays: Animal Models

Various animal models can be used to analyze beta-secretase activity and /or processing of APP to release A beta, as described above. For example, transgenic animals expressing APP substrate and beta-secretase enzyme can be used to demonstrate inhibitory activity of the compounds employed in the methods of the invention. Certain transgenic animal models have been described, for example, in U.S. Pat. Nos.: 5,877,399; 5,612,486; 5,387,742; 5,720,936; 5,850,003; 5,877,015; and 5,811,633, and in Ganes et al., 1995, *Nature* 373:523. Preferred are animals that exhibit characteristics associated with the pathophysiology of AD. Administration of the compound inhibitors of the invention to the transgenic mice described herein provides an alternative method for demonstrating the inhibitory activity of the compounds. Administration of the compounds in a pharmaceutically effective carrier and via an administrative route that reaches the target tissue in an appropriate therapeutic amount is also preferred.

Inhibition of beta-secretase mediated cleavage of APP at the beta-secretase cleavage site and of A beta release can be analyzed in these animals by measure of cleavage fragments in the animal's body fluids such as cerebral fluid or tissues. Analysis of brain tissues for A beta deposits or plaques is preferred.

On contacting an APP substrate with a beta-secretase enzyme in the presence of an inhibitory compound employed in the method of the invention and under conditions sufficient to permit enzymatic mediated cleavage of APP and/or release of A beta from the substrate, the compounds employed in the methods of the invention are effective to reduce beta-secretase-mediated cleavage of APP at the beta-secretase cleavage site and/or effective to reduce released amounts of A beta. Where such contacting is the administration of the inhibitory compounds employed in the methods of the invention to an animal model, for example, as described above, the compounds are effective to reduce A beta deposition in brain tissues of the animal, and to reduce the number and/or size of beta amyloid plaques. Where such administration is to a human subject, the compounds are effective to inhibit or slow the progression of disease characterized by enhanced amounts of A beta, to slow the progression of AD in the, and/or to prevent onset or development of AD in a patient at risk for the disease.

Unless defined otherwise, all scientific and technical terms used herein have the same meaning as commonly understood by one of skill in the art to which this invention belongs. All patents and publications referred to herein are hereby incorporated by reference for all purposes.

DEFINITIONS AND CONVENTIONS

The definitions and explanations below are for the terms as used throughout this entire document including both the specification and the claims.

I. CONVENTIONS FOR FORMULAS AND DEFINITIONS OF VARIABLES

The chemical formulas representing various compounds or molecular fragments in the specification and claims may contain variable substituents in addition to expressly defined structural features. These variable substituents are identified by a letter or a letter followed by a numerical subscript, for example, "$Z_1$" or "$R_i$" where "i" is an integer. These variable substituents are either monovalent or bivalent, that is, they represent a group attached to the formula by one or two chemical bonds. For example, a group $Z_1$ would represent a bivalent variable if attached to the formula $CH_3$—$C(=Z_1)$H. Groups $R_i$ and $R_j$ would represent monovalent variable substituents if attached to the formula $CH_3$—$CH_2$—$C(R_i)$($R_j$)$H_2$. When chemical formulas are drawn in a linear fashion, such as those above, variable substituents contained in parentheses are bonded to the atom immediately to the left of the variable substituent enclosed in parenthesis. When two or more consecutive variable substituents are enclosed in parentheses, each of the consecutive variable substituents is bonded to the immediately preceding atom to the left which is not enclosed in parentheses. Thus, in the formula above, both $R_i$ and $R_j$ are bonded to the preceding carbon atom. Also, for any molecule with an established system of carbon atom numbering, such as steroids, these carbon atoms are designated as $C_i$, where "i" is the integer corresponding to the carbon atom number. For example, $C_6$ represents the 6 position or carbon atom number in the steroid nucleus as traditionally designated by those skilled in the art of steroid chemistry. Likewise the term "$R_6$" represents a variable substituent (either monovalent or bivalent) at the $C_6$ position.

Chemical formulas or portions thereof drawn in a linear fashion represent atoms in a linear chain. The symbol "—" in general represents a bond between two atoms in the chain. Thus $CH_3$—O—$CH_2$—$CH(R_i)$—$CH_3$ represents a 2-substituted-1-methoxypropane compound. In a similar fashion, the symbol "=" represents a double bond, e.g., $CH_2$=$C(R_i)$—O—$CH_3$, and the symbol "≡" represents a triple bond, e.g., HC≡C—$CH(R_i)$—$CH_2$—$CH_3$. Carbonyl groups are represented in either one of two ways: —CO— or —C(=O)—, with the former being preferred for simplicity.

Chemical formulas of cyclic (ring) compounds or molecular fragments can be represented in a linear fashion. Thus, the compound 4-chloro-2-methylpyridine can be represented in linear fashion by N*=C($CH_3$)—CH=CCl—CH=C*H with the convention that the atoms marked with an asterisk (*) are bonded to each other resulting in the formation of a ring. Likewise, the cyclic molecular fragment, 4-(ethyl)- 1-piperazinyl can be represented by —N*—(CH$_2$)$_2$—N(C$_2$H$_5$)—CH$_2$—C*H$_2$.

A rigid cyclic (ring) structure for any compounds herein defines an orientation with respect to the plane of the ring for substituents attached to each carbon atom of the rigid cyclic compound. For saturated compounds which have two substituents attached to a carbon atom which is part of a cyclic system, —C(X$_1$)(X$_2$)— the two substituents may be in either an axial or equatorial position relative to the ring and may change between axial/equatorial. However, the position of the two substituents relative to the ring and each other remains fixed. While either substituent at times may lie in the plane of the ring (equatorial) rather than above or below the plane (axial), one substituent is always above the other. In chemical structural formulas depicting such compounds, a substituent (X$_1$) which is "below" another substituent (X$_2$) will be identified as being in the alpha configuration and is identified by a broken, dashed or dotted line attachment to the carbon atom, i.e., by the symbol " - - - " or " . . . ". The corresponding substituent attached "above" (X$_2$) the other (X$_1$) is identified as being in the beta configuration and is indicated by an unbroken line attachment to the carbon atom.

When a variable substituent is bivalent, the valences may be taken together or separately or both in the definition of the variable. For example, a variable $R_i$ attached to a carbon atom as —C(=R$_i$)— might be bivalent and be defined as oxo or keto (thus forming a carbonyl group (—CO—) or as two separately attached monovalent variable substituents alpha-$R_{i-j}$ and beta-$R_{i-k}$. When a bivalent variable, $R_i$, is defined to consist of two monovalent variable substituents, the convention used to define the bivalent variable is of the form "alpha-$R_{i-j}$:beta-$R_{i-k}$" or some variant thereof. In such a case both alpha-$R_{i-j}$ and beta-$R_{i-k}$ are attached to the carbon atom to give —C(alpha-$R_{i-j}$)(beta-$R_{i-k}$)—. For example, when the bivalent variable $R_6$, —C(=R$_6$)— is defined to consist of two monovalent variable substituents, the two monovalent variable substituents are alpha-$R_{6-1}$:beta-$R_{6-2}$, . . . alpha-$R_{6-9}$:beta-$R_{6-10}$, etc, giving —C(alpha-$R_{6-1}$)(beta-$R_{6-2}$)—, . . . —C(alpha-$R_{6-9}$)(beta-$R_{6-10}$)—, etc. Likewise, for the bivalent variable $R_{11}$, —C(=R$_{11}$)—, two monovalent variable substituents are alpha-$R_{11-1}$:beta-$R_{11-2}$. For a ring substituent for which separate alpha and beta orientations do not exist (e.g. due to the presence of a carbon carbon double bond in the ring), and for a substituent bonded to a carbon atom which is not part of a ring the above convention is still used, but the alpha and beta designations are omitted.

Just as a bivalent variable may be defined as two separate monovalent variable substituents, two separate monovalent variable substituents may be defined to be taken together to form a bivalent variable. For example, in the formula —C$_1$(R$_i$)H—C$_2$(R$_j$)H— (C$_1$ and C$_2$ define arbitrarily a first and second carbon atom, respectively) $R_i$ and $R_j$ may be defined to be taken together to form (1) a second bond between C$_1$ and C$_2$ or (2) a bivalent group such as oxa (—O—) and the formula thereby describes an epoxide. When $R_i$ and $R_j$ are taken together to form a more complex entity, such as the group —X—Y—, then the orientation of the entity is such that C$_1$ in the above formula is bonded to X and C$_2$ is bonded to Y. Thus, by convention the designation " . . . R$_i$ and R$_j$ are taken together to form —CH$_2$—CH$_2$—O—CO— . . . " means a lactone in which the carbonyl is bonded to C$_2$. However, when designated " . . . R$_j$ and R$_i$ are taken together to form —CO—O—CH$_2$—CH$_2$— the convention means a lactone in which the carbonyl is bonded to C$_1$.

The carbon atom content of variable substituents is indicated in one of two ways. The first method uses a prefix to the entire name of the variable such as "C$_1$–C$_4$", where both "1" and "4" are integers representing the minimum and maximum number of carbon atoms in the variable. The prefix is separated from the variable by a space. For example, "C$_1$–C$_4$ alkyl" represents alkyl of 1 through 4 carbon atoms, (including isomeric forms thereof unless an express indication to the contrary is given). Whenever this single prefix is given, the prefix indicates the entire carbon atom content of the variable being defined. Thus C$_2$–C$_4$ alkoxycarbonyl describes a group CH$_3$—(CH$_2$)$_n$—O—CO— where n is zero, one or two. By the second method the carbon atom content of only each portion of the definition is indicated separately by enclosing the "C$_i$–C$_j$" designation in parentheses and placing it immediately (no intervening space) before the portion of the definition being defined. By this optional convention (C$_1$–C$_3$)alkoxycarbonyl has the same meaning as C$_2$–C$_4$ alkoxy-carbonyl because the "C$_1$–C$_3$" refers only to the carbon atom content of the alkoxy group. Similarly while both C$_2$–C$_6$ alkoxyalkyl and (C$_1$–C$_3$) alkoxy(C$_1$–C$_3$)alkyl define alkoxyalkyl groups containing from 2 to 6 carbon atoms, the two definitions differ since the former definition allows either the alkoxy or alkyl portion alone to contain 4 or 5 carbon atoms while the latter definition limits either of these groups to 3 carbon atoms.

When the claims contain a fairly complex (cyclic) substituent, at the end of the phrase naming/designating that particular substituent will be a notation in (parentheses) which will correspond to the same name/designation in one of the CHARTS which will also set forth the chemical structural formula of that particular substituent.

II. DEFINITIONS

All temperatures are in degrees Celsius.

TLC refers to thin-layer chromatography.

psi refers to pounds/in$^2$.

HPLC refers to high pressure liquid chromatography.

THF refers to tetrahydrofuran.

DMF refers to dimethylformamide.

EDC refers to ethyl-1-(3-dimethylaminopropyl) carbodiimide or 1-(3-dimethylaminopropyl)-3-ethylcarbodiimide hydrochloride.

HOBt refers to 1-hydroxy benzotriazole hydrate.

NMM refers to N-methylmorpholine.

NBS refers to N-bromosuccinimide.

TEA refers to triethylamine.

BOC refers to 1,1-dimethylethoxy carbonyl or t-butoxycarbonyl, —CO—O—C(CH$_3$)$_3$.

CBZ refers to benzyloxycarbonyl, —CO—O—CH$_2$-ϕ.

FMOC refers to 9-fluorenylmethyl carbonate.

TFA refers to trifluoracetic acid, CF$_3$—COOH.

CDI refers to 1,1'-carbonyldiimidazole.

Saline refers to an aqueous saturated sodium chloride solution.

Chromatography (column and flash chromatography) refers to purification/separation of compounds expressed as (support, eluent). It is understood that the appropriate fractions are pooled and concentrated to give the desired compound(s).

CMR refers to C-13 magnetic resonance spectroscopy, chemical shifts are reported in ppm (6) downfield from TMS.

NMR refers to nuclear (proton) magnetic resonance spectroscopy, chemical shifts are reported in ppm (d) downfield from TMS.

IR refers to infrared spectroscopy.

MS refers to mass spectrometry expressed as m/e, m/z or mass/charge unit. MH+ refers to the positive ion of a parent plus a hydrogen atom. EI refers to electron impact. CI refers to chemical ionization. FAB refers to fast atom bombardment.

HRMS refers to high resolution mass spectrometry.

Ether refers to diethyl ether.

Pharmaceutically acceptable refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability.

When solvent pairs are used, the ratios of solvents used are volume/volume (v/v).

When the solubility of a solid in a solvent is used the ratio of the solid to the solvent is weight/volume (wt/v).

BOP refers to benzotriazol-1-yloxy-tris(dimethylamino) phosphonium hexafluorophosphate.

TBDMSCl refers to t-butyldimethylsilyl chloride.

TBDMSOTf refers to t-butyldimethylsilyl trifluorosulfonic acid ester.

Trisomy 21 refers to Down's Syndrome.

The following terms are used (in EXAMPLEs 321 and above) for the amide forming agent (IX):

"PHTH" refers to $(CH_3-CH_2-CH_2-)_2N-CO$-phenyl-CO—OH where the attachment to the -phenyl-ring is 1,3-;

"5-Me-PHTH" refers to $(CH_3-CH_2-CH_2-)_2N-CO-(CH_3-)$phenyl-CO—OH where the attachment to the -phenyl-ring is 1,3- for the carbonyl groups and 5- for the methyl group;

"3,5-pyridinyl" refers to $(CH_3-CH_2-CH_2-)_2N-CO$-(pyridinyl)-CO—OH where the attachment to the -pyridinyl-ring is 3,5- for the carbonyl groups;

"—$SO_2$—" refers to $(CH_3-CH_2-CH_2-)_2CH-SO_2$-phenyl-CO—OH where the attachment to the -phenyl-ring is 1,3-;

"5-OMe-PHTH" refers to $(CH_3-CH_2-CH_2-)_2N-CO-(CH_3-O-)$phenyl-CO—OH where the attachment to the -phenyl-ring is 1,3- for the carbonyl groups and 5- for the methoxy group;

"5-Cl-PHTH" refers to $(CH_3-CH_2-CH_2-)_2N-CO-(Cl-)$phenyl-CO—OH where the attachment to the —phenyl—ring is 1,3- for the carbonyl groups and 5- for the chlorine atom;

"5-F-PHTH" refers to $(CH_3-CH_2-CH_2-)_2N-CO-(F-)$phenyl-CO—OH where the attachment to the —phenyl—ring is 1,3- for the carbonyl groups and 5- for the fluorine atom;

"thienyl" refers to $(CH_3-CH_2-CH_2-)_2N-CO$-thienyl-CO—OH where the attachment to the thiophene ring is -2,5;

"2,4-pyridinyl" refers to $(CH_3-CH_2-CH_2-)_2N-CO$-(pyridinyl)-CO—OH where the attachment to the "pyridinyl" ring is 2,4- for the carbonyl groups;

"4,6-pyrimidinyl" refers to $(CH_3-CH_2-CH_2-)_2N-CO$-(pyrimidinyl-)phenyl-CO—OH where the attachment to the -pyrimidiny-1 ring is 4,6- for the carbonyl groups;

"morpholinyl" refers to morpholinyl-CO-phenyl-CO—OH where the attachment to the —phenyl—ring is 1,3 for the carbonyl groups.

APP, amyloid precursor protein, is defined as any APP polypeptide, including APP variants, mutations, and isoforms, for example, as disclosed in U.S. Pat. No. 5,766,846.

A beta, amyloid beta peptide, is defined as any peptide resulting from beta-secretase mediated cleavage of APP, including peptides of 39, 40, 41, 42, and 43 amino acids, and extending from the beta-secretase cleavage site to amino acids 39, 40, 41, 42, or 43.

Beta-secretase (BACE1, Asp2, Memapsin 2) is an aspartyl protease that mediates cleavage of APP at the amino-terminal edge of A beta. Human beta-secretase is described, for example, in WO00/17369.

A therapeutically effective amount is defined as an amount effective to reduce or lessen at least one symptom of the disease being treated or to reduce or delay onset of one or more clinical markers or symptoms of the disease.

The present invention provides compounds, compositions, and methods for inhibiting beta-secretase enzyme activity and A beta peptide production. Inhibition of beta-secretase enzyme activity halts or reduces the production of A beta from APP and reduces or eliminates the formation of beta-amyloid deposits in the brain.

CHEMICAL EXAMPLES

Exemplary Compounds of the Invention

Examples of compounds that are within the invention include but are not limited to those depicted below.

Example 1, N-[1-(3,5-Difluoro-benzyl)-2-hydroxy-3-(N'-methyl-N'-phenyl-hydrazino)-propyl]-5-methyl-N', N'-dipropyl-isophthalamide

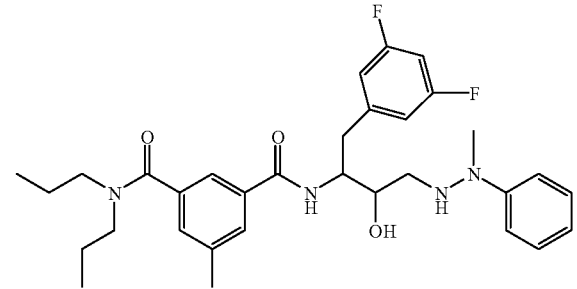

Example 2, N-{1-(3,5-Difluoro-benzyl)-2-hydroxy-3-[N'-methyl-N'-(4-methyl-pentanoyl)-hydrazino]-propyl}-5-methyl-N',N'-dipropyl-isophthalamide

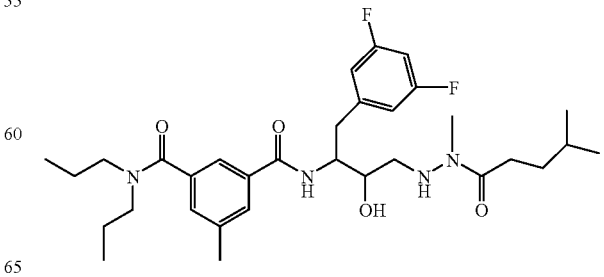

Example 3, N-[1(3,5-Difluoro-benzyl)-2-hydroxy-3-phenoxyamino-propyl]-S-methyl-N',N'-dipropyl-isophthalamide
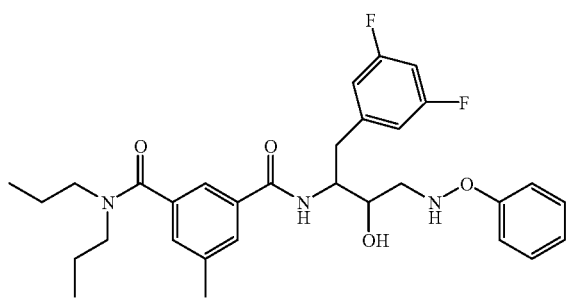
CHART A
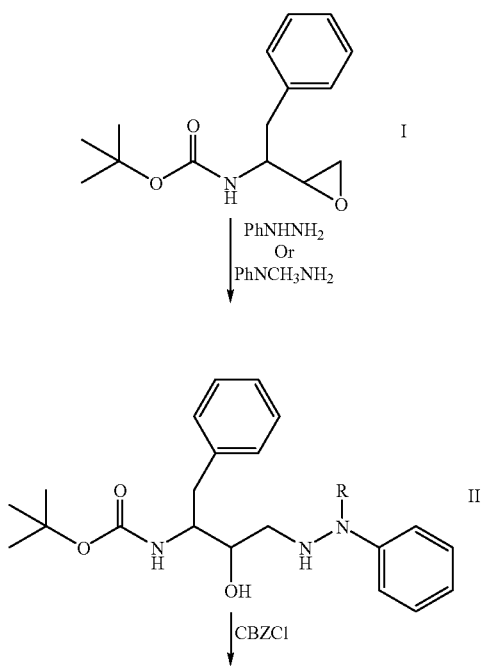
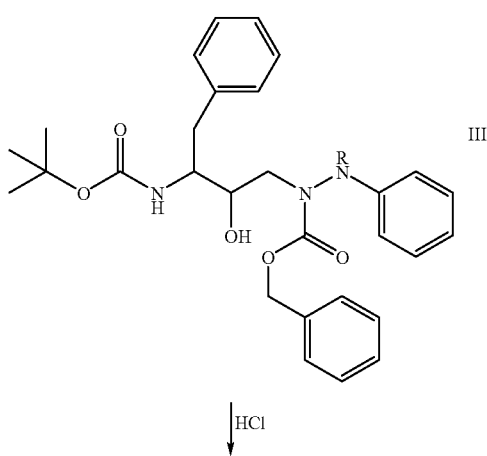
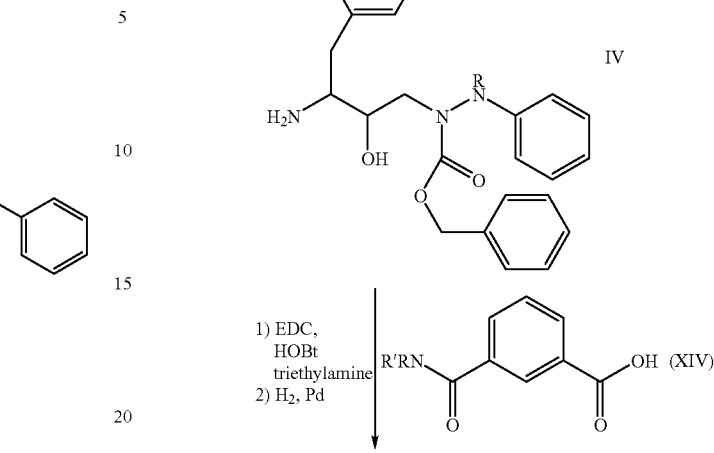
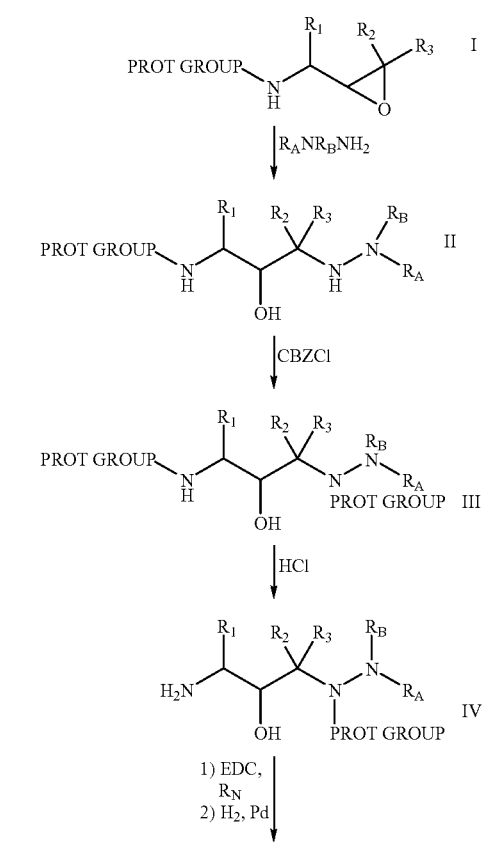
CHART A'

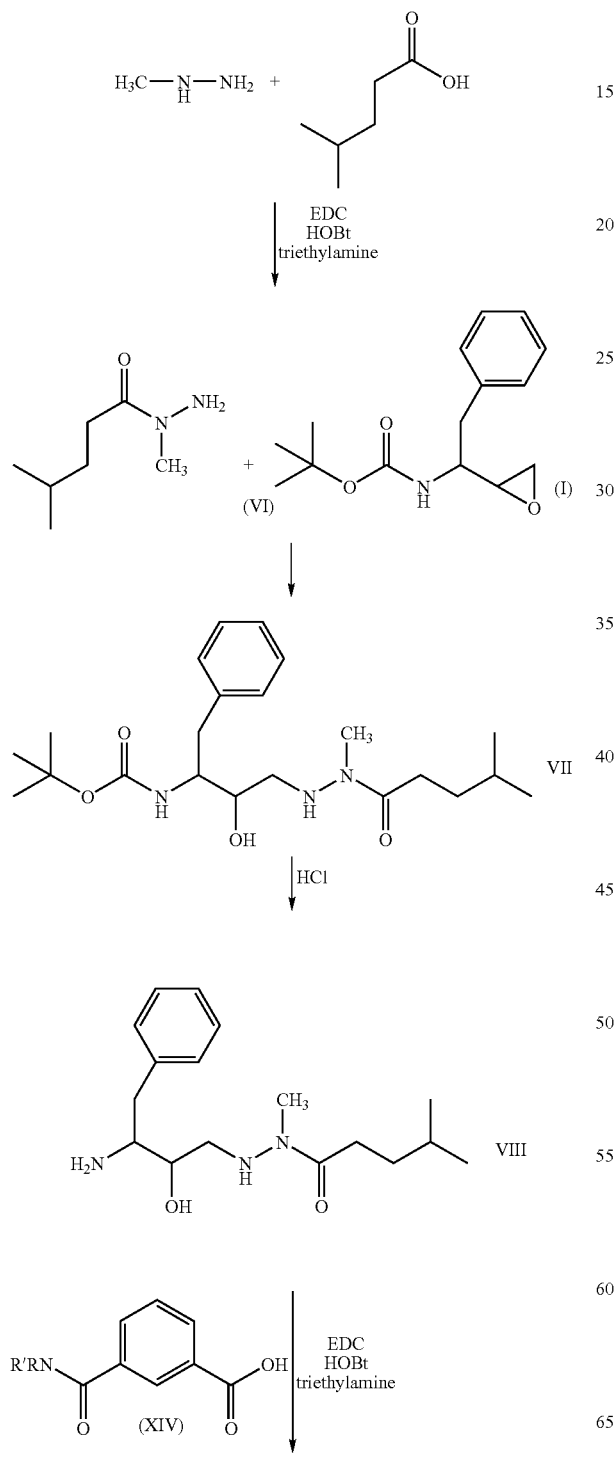

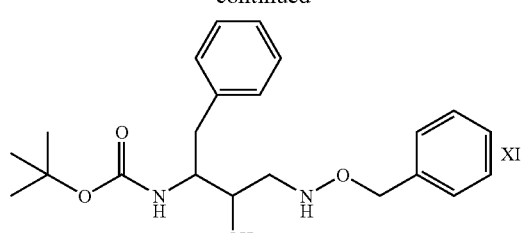

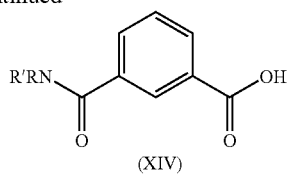

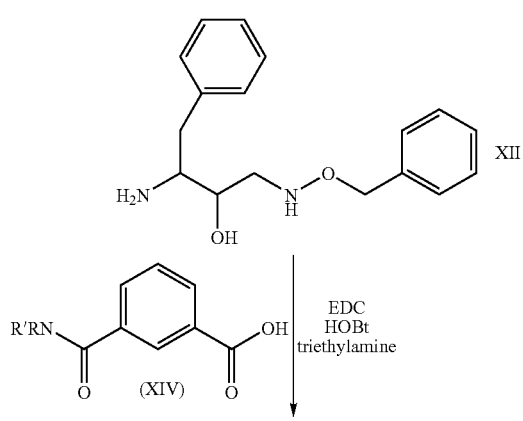

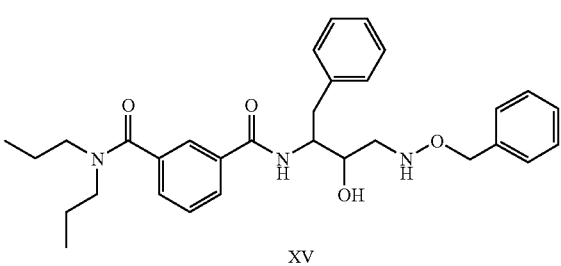

CHART D

CHART D

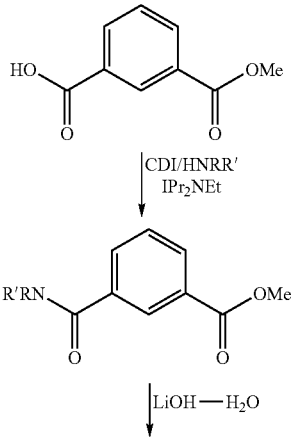

BIOLOGICAL EXAMPLES

Example A

Enzyme Inhibition Assay

The compounds of the invention are analyzed for inhibitory activity by use of the MBP-C125 assay. This assay determines the relative inhibition of beta-secretase cleavage of a model APP substrate, MBP-C125SW, by the compounds assayed as compared with an untreated control. A detailed description of the assay parameters can be found, for example, in U.S. Pat. No. 5,942,400. Briefly, the substrate is a fusion peptide formed of maltose binding protein (MBP) and the carboxy terminal 125 amino acids of APP-SW, the Swedish mutation. The beta-secretase enzyme is derived from human brain tissue as described in Sinha et.al, 1999, Nature 40:537–540) or recombinantly produced as the full-length enzyme (amino acids 1–501), and can be prepared, for example, from 293 cells expressing the recombinant cDNA, as described in WO00/47618.

Inhibition of the enzyme is analyzed, for example, by immunoassay of the enzyme's cleavage products. One exemplary ELISA uses an anti-MBP capture antibody that is deposited on precoated and blocked 96-well high binding plates, followed by incubation with diluted enzyme reaction supernatant, incubation with a specific reporter antibody, for example, biotinylated anti-SW192 reporter antibody, and further incubation with streptavidin/alkaline phosphatase. In the assay, cleavage of the intact MBP-C125SW fusion protein results in the generation of a truncated amino-terminal fragment, exposing a new SW-192 antibody-positive epitope at the carboxy terminus. Detection is effected by a fluorescent substrate signal on cleavage by the phosphatase. ELISA only detects cleavage following Leu 596 at the substrate's APP-SW 751 mutation site.

Specific Assay Procedure

Compounds are diluted in a 1:1 dilution series to a six-point concentration curve (two wells per concentration) in one 96-plate row per compound tested. Each of the test compounds is prepared in DMSO to make up a 10 millimolar stock solution. The stock solution is serially diluted in DMSO to obtain a final compound concentration of 200 micromolar at the high point of a 6-point dilution curve. Ten (10) microliters of each dilution is added to each of two wells on row C of a corresponding V-bottom plate to which 190 microliters of 52 millimolar NaOAc, 7.9% DMSO, pH 4.5 are pre-added. The NaOAc diluted compound plate is spun down to pellet precipitant and 20 microliters/well is transferred to a corresponding flat-bottom plate to which 30 microliters of ice-cold enzyme-substrate mixture (2.5 microliters MBP-C125SW substrate, 0.03 microliters enzyme and 24.5 microliters ice cold 0.09% TX100 per 30 microliters) is added. The final reaction mixture of 200 micromolar compound at the highest curve point is in 5% DMSO, 20 millimolar NaAc, 0.06% TX100, at pH 4.5.

Warming the plates to 37 degrees C. starts the enzyme reaction. After 90 minutes at 37 degrees C., 200 microliters/well cold specimen diluent is added to stop the reaction and 20 microliters/well is transferred to a corresponding anti-MBP antibody coated ELISA plate for capture, containing 80 microliters/well specimen diluent. This reaction is incubated overnight at 4 degrees C. and the ELISA is developed the next day after a 2 hour incubation with anti-192SW antibody, followed by Streptavidin-AP conjugate and fluorescent substrate. The signal is read on a fluorescent plate reader.

Relative compound inhibition potency is determined by calculating the concentration of compound that showed a fifty percent reduction in detected signal ($IC_{50}$) compared to the enzyme reaction signal in the control wells with no added compound. In this assay, the compounds of the invention exhibited an $IC_{50}$ of less than 50 micromolar.

Example B
Cell Free Inhibition Assay utilizing a Synthetic APP Substrate

A synthetic APP substrate that can be cleaved by beta-secretase and having N-terminal biotin and made fluorescent by the covalent attachment of oregon green at the Cys residue is used to assay beta-secretase activity in the presence or absence of the inhibitory compounds of the invention. Useful substrates include the following:

Biotin-SEVNL-DAEFR[oregon green]KK [SEQ ID NO: 1]
Biotin-SEVKM-DAEFR[oregon green]KK [SEQ ID NO: 2]
Biotin-GLNIKTEEISEISY-EVEFRC[oregon green]KK [SEQ ID NO: 3]
Biotin-ADRGLTTRPGSGLTNIKTEEISEVNL-DAEF[oregon green]KK [SEQ ID NO:4]
Biotin-FVNQHLCoxGSHLVEALY-LVCoxGERGFFYTPKA[oregon green]KK [SEQ ID NO: 5]

The enzyme (0.1 nanomolar) and test compounds (0.001–100 micromolar) are incubated in pre-blocked, low affinity, black plates (384 well) at 37 degrees C. for 30 minutes. The reaction is initiated by addition of 150 millimolar substrate to a final volume of 30 microliter per well. The final assay conditions are: 0.001–100 micromolar compound inhibitor; 0.1 molar sodium acetate (pH 4.5); 150 nanomolar substrate; 0.1 nanomolar soluble beta-secretase; 0.001% Tween 20, and 2% DMSO. The assay mixture is incubated for 3 hours at 37° C., and the reaction is terminated by the addition of a saturating concentration of immunopure streptavidin. After incubation with streptavidin at room temperature for 15 minutes, fluorescence polarization is measured, for example, using a LJL Acqurest (Ex485 nm/Em530 nm). The activity of the beta-secretase enzyme is detected by changes in the fluorescence polarization that occur when the substrate is cleaved by the enzyme. Incubation in the presence or absence of compound inhibitor demonstrates specific inhibition of beta-secretase enzymatic cleavage of its synthetic APP substrate. In this assay, compounds of the invention exhibited an IC50 of less than 50 micromolar.

Example C
Beta-secretase inhibition: P26-P4'SW assay

Synthetic substrates containing the beta-secretase cleavage site of APP are used to assay beta-secretase activity, using the methods described, for example, in published PCT application WO00/47618. The P26-P4'SW substrate is a peptide of the sequence:

(biotin)CGGADRGLTTRPGSGLTNIKTEEISEVNLDAEF [SEQ ID NO: 6]

The P26-P1 standard has the sequence:

(biotin)CGGADRGLTTRPGSGLTNIKTEEISEVNL [SEQ ID NO: 7]

Briefly, the biotin-coupled synthetic substrates are incubated at a concentration of from about 0 to about 200 micromolar in this assay. When testing inhibitory compounds, a substrate concentration of about 1.0 micromolar is preferred. Test compounds diluted in DMSO are added to the reaction mixture, with a final DMSO concentration of 5%. Controls also contain a final DMSO concentration of 5%. The concentration of beta secretase enzyme in the reaction is varied, to give product concentrations with the linear range of the ELISA assay, about 125 to 2000 picomolar, after dilution.

The reaction mixture also includes 20 millimolar sodium acetate, pH 4.5, 0.06% Triton X100, and is incubated at 37 degrees C. for about 1 to 3 hours. Samples are then diluted in assay buffer (for example, 145.4 nanomolar sodium chloride, 9.51 millimolar sodium phosphate, 7.7 millimolar sodium azide, 0.05% Triton X405, 6 g/liter bovine serum albumin, pH 7.4) to quench the reaction, then diluted further for immunoassay of the cleavage products.

Cleavage products can be assayed by ELISA. Diluted samples and standards are incubated in assay plates coated with capture antibody, for example, SW 192, for about 24 hours at 4 degrees C. After washing in TTBS buffer (150 millimolar sodium chloride, 25 millimolar Tris, 0.05% Tween 20, pH 7.5), the samples are incubated with strepavidin-AP according to the manufacturer's instructions. After a one hour incubation at room temperature, the samples are washed in TTBS and incubated with fluorescent substrate solution A (31.2 g/liter 2-amino-2-methyl-1-propanol, 30 mg/liter, pH 9.5). Reaction with streptavidin-alkaline phosphate permits detection by fluorescence. Compounds that are effective inhibitors of beta-secretase activity demonstrate reduced cleavage of the substrate as compared to a control.

Example D
Assays using Synthetic Oligopeptide-Substrates

Synthetic oligopeptides are prepared that incorporate the known cleavage site of beta-secretase, and optionally detectable tags, such as fluorescent or chouromogenic moieties. Examples of such peptides, as well as their production and detection methods are described in U.S. Pat. No. 5,942,400, herein incorporated by reference. Cleavage products can be detected using high performance liquid chouromatography, or fluorescent or chouromogenic detection methods appropriate to the peptide to be detected, according to methods well known in the art.

By way of example, one such peptide has the sequence SEVNL-DAEF [SEQ ID NO: 8], and the cleavage site is between residues 5 and 6. Another preferred substrate has the sequence ADRGLTTRPGSGLTNIKTEEISEVNL-DAEF [SEQ ID NO: 9], and the cleavage site is between residues 26 and 27.

These synthetic APP substrates are incubated in the presence of beta-secretase under conditions sufficient to result in beta-secretase mediated cleavage of the substrate. Comparison of the cleavage results in the presence of the compound inhibitor to control results provides a measure of the compound's inhibitory activity.

Example E
Inhibition of Beta-secretase Activity—Cellular Assay

An exemplary assay for the analysis of inhibition of beta-secretase activity utilizes the human embryonic kidney cell line HEKp293 (ATCC Accession No. CRL-1573) transfected with APP751 containing the naturally occurring double mutation Lys651Met52 to Asn651Leu652 (numbered for APP751), commonly called the Swedish mutation and shown to overproduce A beta (Citron et.al., 1992, *Nature* 360:672–674), as described in U.S. Pat. No. 5,604,102.

The cells are incubated in the presence/absence of the inhibitory compound (diluted in DMSO) at the desired concentration, generally up to 10 micrograms/ml. At the end of the treatment period, conditioned media is analyzed for beta-secretase activity, for example, by analysis of cleavage fragments. A beta can be analyzed by immunoassay, using specific detection antibodies. The enzymatic activity is measured in the presence and absence of the compound inhibitors to demonstrate specific inhibition of beta-secretase mediated cleavage of APP substrate.

Example F
Inhibition of Beta-Secretase in Animal Models of AD

Various animal models can be used to screen for inhibition of beta-secretase activity. Examples of animal models useful in the invention include, but are not limited to, mouse, guinea pig, dog, and the like. The animals used can be wild type, transgenic, or knockout models. In addition, mammalian models can express mutations in APP, such as APP695-SW and the like described herein. Examples of transgenic non-human mammalian models are described in U.S. Pat. Nos. 5,604,102, 5,912,410 and 5,811,633.

PDAPP mice, prepared as described in Games et.al., 1995, *Nature* 373:523–527 are useful to analyze in vivo suppression of A beta release in the presence of putative inhibitory compounds. As described in U.S. Pat. No. 6,191,166, 4 month old PDAPP mice are administered compound formulated in vehicle, such as corn oil. The mice are dosed with compound (1–30 mg/ml; preferably 1–10 mg/ml). After time, e.g., 3–10 hours, the animals are sacrificed, and brains removed for analysis.

Transgenic animals are administered an amount of the compound inhibitor formulated in a carrier suitable for the chosen mode of administration. Control animals are untreated, treated with vehicle, or treated with an inactive compound. Administration can be acute, i.e., single dose or multiple doses in one day, or can be chouronic, i.e., dosing is repeated daily for a period of days. Beginning at time 0, brain tissue or cerebral fluid is obtained from selected animals and analyzed for the presence of APP cleavage peptides, including A beta, for example, by immunoassay using specific antibodies for A beta detection. At the end of the test period, animals are sacrificed and brain tissue or cerebral fluid is analyzed for the presence of A beta and/or beta-amyloid plaques. The tissue is also analyzed for necrosis.

Animals administered the compound inhibitors of the invention are expected to demonstrate reduced A beta in brain tissues or cerebral fluids and reduced beta amyloid plaques in brain tissue, as compared with non-treated controls.

Example G
Inhibition of A Beta Production in Human Patients

Patients suffering from Alzheimer's Disease (AD) demonstrate an increased amount of A beta in the brain. AD patients are administered an amount of the compound inhibitor formulated in a carrier suitable for the chosen mode of administration. Administration is repeated daily for the duration of the test period. Beginning on day 0, cognitive and memory tests are performed, for example, once per month.

Patients administered the compound inhibitors are expected to demonstrate slowing or stabilization of disease progression as analyzed by changes in one or more of the following disease parameters: A beta present in CSF or plasma; brain or hippocampal volume; A beta deposits in the brain; amyloid plaque in the brain; and scores for cognitive and memory function, as compared with control, non-treated patients.

Example H

Prevention of a Beta Production in Patients at Risk for AD

Patients predisposed or at risk for developing AD are identified either by recognition of a familial inheritance pattern, for example, presence of the Swedish Mutation, and/or by monitoring diagnostic parameters. Patients identified as predisposed or at risk for developing AD are administered an amount of the compound inhibitor formulated in a carrier suitable for the chosen mode of administration. Administration is repeated daily for the duration of the test period. Beginning on day 0, cognitive and memory tests are performed, for exmple, once per month.

Patients administered the compound inhibitors are expected to demonstrate slowing or stabilization of disease progression as analyzed by changes in one or more of the following disease parameters: A beta present in CSF or plasma; brain or hippocampal volume; amyloid plaque in the brain; and scores for cognitive and memory function, as compared with control, non-treated patients.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

Unless defined otherwise, all scientific and technical terms used herein have the same meaning as commonly understood by one of skill in the art to which this invention belongs.

All patents and publications referred to herein are hereby incorporated by reference for all purposes.

The invention has been described with reference to various specific and preferred embodiments and techniques. However, it should be understood that many variations and modifications may be made while remaining within the spirit and scope of the invention.

What is claimed is:

1. A substituted amine of formula (XV)

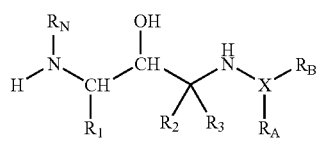

(XV)

or a salt thereof, where $R_1$ is —$(CH_2)_{n1}$—$(R_{1\text{-}aryl})$ where $n_1$ is zero or one and where $R_{1\text{-}aryl}$ is phenyl, optionally substituted with one, two, or three of the following substituents (A) $C_1$–$C_6$ alkyl optionally substituted with one, two or three substituents selected from the group consisting of $C_1$–$C_3$ alkyl, —F, —Cl, —Br, —I, —OH, —SH, —C≡N, —CF$_3$, $C_1$–$C_3$ alkoxy, and —NR$_{1\text{-}a}$R$_{1\text{-}b}$ where $R_{1\text{-}a}$ and $R_{1\text{-}b}$ —H or $C_1$–$C_6$ alkyl, (D) —F, Cl, —Br or —I, (F) —$C_1$–$C_6$ alkoxy optionally substituted with one, two, or three of: —F, (G) —$NR_{N-2}R_{N-3}$ where $R_{N-2}$ and $R_{N-3}$ are as defined below,
(H) —OH,
(I) —C≡N,
(K) —CO—($C_1$–$C_4$ alkyl),
where $R_2$ is:
—H, or $C_1$–$C_3$ alkyl;
where $R_3$ is:
—H or $C_1$–$C_3$ alkyl;
where $R_N$ is $R_{N-1}$—$X_N$— where $X_N$ is selected from the group consisting of:
(A) —CO—,
(B) —$SO_2$—,
(C) —$(CR'R'')_{1-6}$ where R' and R'' are the same or different and are —H or $C_1$–$C_4$ alkyl,
(E) a single bond;
where $R_{N-1}$ is $R_{N-aryl}$ where $R_{N-aryl}$ is phenyl, 1-naphthyl, or 2-naphthyl, each of which is optionally substituted with one, two or three of the following substituents which can be the same or different and are:
(1) $C_1$–$C_6$ alkyl, optionally substituted with one, two or three substituents selected from the group consisting of $C_1$–$C_3$ alkyl, —F, —Cl, —Br, —I, —OH, —SH, —C≡N, —$CF_3$, $C_1$–$C_3$ alkoxy, and —$NR_{1-a}R_{1-b}$ where $R_{1-a}$ and $R_{1-b}$ are as defined above,
(2) —OH,
(3) —$NO_2$,
(4) —F, —Cl, —Br, or —I,
(5) —CO—OH,
(6) —C≡N,
(7) —$(CH_2)_{0-4}$—CO—$NR_{N-2}R_{N-3}$ where $R_{N-2}$ and $R_{N-3}$ are the same or different and are selected from the group consisting of:
 (a) —H,
 (b) —$C_1$–$C_6$ alkyl optionally substituted with one substitutent selected from the group consisting of:
  (i) —OH, and
  (ii) —$NH_2$,
 (c) —$C_1$–$C_6$ alkyl optionally substituted with one to three —F, —Cl, —Br, or —I,
 (d) —$C_3$–$C_7$ cycloalkyl,
 (e) —($C_1$–$C_2$ alkyl)-($C_3$–$C_7$ cycloalkyl),
 (f) —($C_1$–$C_6$ alkyl)-O—($C_1$–$C_3$ alkyl),
(8) —$(CH_2)_{0-4}$—CO—($C_1$–$C_{12}$ alkyl),
(11) —$(CH_2)_{0-4}$—CO—($C_3$–$C_7$ cycloalkyl),
(15) —$(CH_2)_{0-4}$—CO—$R_{N-4}$ where $R_{N-4}$ is selected from the group consisting of morpholinyl, thiomorpholinyl, piperazinyl, piperidinyl, homomorpholinyl, homothiomorpholinyl, homothiomorpholinyl S-oxide, homothiomorpholinyl S,S-dioxide, pyrrolinyl and pyrrolidinyl where each group is optionally substituted with one, two, three, or four of $C_1$–$C_6$ alkyl,
(16) —$(CH_2)_{0-4}$—CO—O—$R_{N-5}$ where $R_{N-5}$ is selected from the group consisting of:
 (a) $C_1$–$C_6$ alkyl,
 (b) —$(CH_2)_{0-2}$—($R_{1-aryl}$) where $R_{1-aryl}$ is as defined above,
 (e) $C_3$–$C_7$ cycloalkyl, and
(21) —$(CH_2)_{0-4}$—N(H or $R_{N-5}$)—CO—O—$R_{N-5}$ where $R_{N-5}$ can be the same or different
(24) —$(CH_2)_{0-4}$—N(—H or $R_{N-5}$)—CO—$R_{N-2}$ where $R_{N-5}$ and $R_{N-2}$ can be the same or different,
(25) —$(CH_2)_{0-4}$—$NR_{N-2}R_{N-3}$ where $R_{N-2}$ and $R_{N-3}$ can be the same or different,
(26) —$(CH_2)_{0-4}$—$R_{N-4}$,
(27) —$(CH_2)_{0-4}$—O—CO—($C_1$–$C_6$ alkyl),
(29) —$(CH_2)_{0-4}$—O—CO—N$(R_{N-5})_2$,
(31) —$(CH_2)_{0-4}$—O—$(R_{N-5})_2$,
(34) —$(CH_2)_{0-4}$—O—($C_1$–$C_6$ alkyl optionally substituted with one, two, three, four, or five —F),
(35) $C_3$–$C_7$ cycloalkyl,
(39) —$(CH_2)_{0-4}$—$C_3$–$C_7$ cycloalkyl,
where $R_4$ is:
(I) —$C_1$–$C_{10}$ alkyl optionally substituted with one, two or three substituents selected from the group consisting of $C_1$–$C_3$ alkyl, —F, —Cl, —Br, —I, —OH, —SH, —C≡N, —$CF_3$, $C_1$–$C_6$ alkoxy, —O-phenyl, —$NR_{1-a}R_{1-b}$ where $R_{1-a}$ and $R_{1-b}$ are as defined above, —OC=O $NR_{1-a}R_{1-b}$ where $R_{1-a}$ and $R_{1-b}$ are as defined above, —$S(=O)_{0-2}$ $R_{1-a}$ where $R_{1-a}$ is as defined above, —$NR_{1-a}$C=O $NR_{1-a}R_{1-b}$ where $R_{1-a}$ and $R_{1-b}$ are as defined above, —C=O $NR_{1-a}R_{1-b}$ where $R_{1-a}$ and $R_{1-b}$ are as defined above, and —$S(=O)_2$ $NR_{1-a}R_{1-b}$ where $R_{1-a}$ and $R_{1-b}$ are as defined above,
(III) —$(CR_{A-x}R_{A-y})_{0-4}$—$R_{A-aryl}$ where $R_{A-x}$ and $R_{A-y}$ are
 (A) —H,
 (B) $C_1$–$C_4$ alkyl optionally substituted with one or two —OH,
 (C) $C_1$–$C_4$ alkoxy optionally substituted with one, two, or three of: —F,
 (D) —$(CH_2)_{0-4}$—$C_3$–$C_7$ cycloalkyl,
 (E) $C_2$–$C_6$ alkenyl containing one or two double bonds,
 (F) $C_2$–$C_6$ alkynyl containing one or two triple bonds,
 (G) phenyl,
(IV) -cyclopentyl, -cyclohexyl, or -cycloheptyl ring fused to $R_{A-aryl}$, where $R_{A-aryl}$ is as defined above where one carbon of cyclopentyl, cyclohexyl, or -cycloheptyl is optionally replaced with NH, $NR_{N-5}$, O, or $S(=O)_{0-2}$, and where cyclopentyl, cyclohexyl, or -cycloheptyl can be optionally substituted with one or two —$C_1$–$C_3$ alkyl, —F, —OH, —SH, —C≡N, —$CF_3$, $C_1$–$C_6$ alkoxy, =O, or —$NR_{1-a}R_{1-b}$ where $R_{1-a}$ and $R_{1-b}$ are as defined above,
(VI) —H,
(VII) —C=O$R_7$,
wherein $R_7$ is:
 $C_1$–$C_6$ alkyl,
 phenyl,
 (aryl)alkyl,
 cycloalkyl,
 cycloalkylalkyl,
 hydroxyalkyl,
 alkoxyalkyl,
 aryloxyalkyl,
 haloalkyl,
 carboxyalkyl,
 alkoxycarbonylalkyl,
 aminoalkyl,
 alkylaminoalkyl,
 dialkylaminoalkyl,
 lower alkenyl,
where X is —N, or —O, with the proviso that when X is O, $R_B$ is absent;
and when X is N,
$R_B$ is:
—$C_1$–$C_{10}$ alkyl optionally substituted with one, two or three substituents selected from the group consisting of $C_1$–$C_3$ alkyl, —F, —Cl, —Br, —I, —OH, —SH, —C≡N, $CF_3$, $C_1$–$C_6$ alkoxy, —O-phenyl, —$NR_{1-a}R_{1-b}$ —OC=O $NR_{1-a}R_{1-b}$ —C=O NR$_{1-a}$R$_{1-b}$ where R$_{1-a}$ and R$_{1-b}$ are as defined above, and S(=O)$_2$ NR$_{1-a}$R$_{1-b}$;
(II) —(CH$_2$)$_{0-3}$—(C$_3$–C$_8$) cycloalkyl where cycloalkyl can be optionally substituted with one, two or three substituents selected from the group consisting of C$_1$–C$_3$ alkyl, —F, —Cl, —Br, —I, —OH, —SH, —C≡N, —CF$_3$, C$_1$–C$_6$ alkoxy, —O-phenyl, —CO—OH, —CO—O—(C$_1$–C$_4$ alkyl), and NR$_{1-a}$R$_{1-b}$; or —H.

2. A substituted amine according to claim 1
where R$_1$ is:
—(CH$_2$)$_{0-1}$-phenyl, wherein the phenyl group is optionally substituted with 1 or 2 groups that are F, Cl, Br, C$_1$–C$_4$ alkoxy, CF$_3$, C$_1$–C$_6$ alkyl optionally substituted with one or two substituents selected from the group consisting of C$_1$–C$_3$ alkyl, —F, —Cl, —Br, —OH, —C≡N, —CF$_3$, C$_1$–C$_3$ alkoxy, and —NR$_{1-a}$R$_{1-b}$ where R$_{1-a}$ and R$_{1-b}$ —H or C$_1$–C$_4$ alkyl,
where R$_N$ is:
R$_{N-1}$—X$_N$— where X$_N$ is selected from the group consisting of:
—CO—, and
—SO$_2$—,
where R$_{N-1}$ is —R$_{N-aryl}$;
where R$_A$ is:
—C$_1$–C$_8$ alkyl,
—(CH$_2$)$_{0-3}$—(C$_3$–C$_7$) cycloalkyl,
—(CR$_{A-x}$R$_{A-y}$)$_{0-4}$—R$_{A-aryl}$,
-cyclopentyl or -cyclohexyl ring fused to R$_{A-aryl}$, or
—C=OR$_7$, where R$_7$ is
C$_1$–C$_6$ alkyl,
phenyl,
phenylalkyl,
cycloalkyl,
cycloalkylalkyl,
hydroxyalkyl,
alkoxyalkyl,
phenyloxyalkyl
haloalkyl,
carboxyalkyl,
where X is —N or —O, with the proviso that when X is O, R$_B$ is absent; and when X is N,
R$_B$ is:
—C$_1$–C$_6$ alkyl.

3. A substituted amine according to claim 2 where R$_1$ is:
benzyl, wherein the phenyl portion is optionally substituted with 1 or 2 groups that are F, Cl, C$_1$–C$_4$ alkoxy, CF$_3$, C$_1$–C$_4$ alkyl optionally substituted with one substituent selected from the group consisting of C$_1$–C$_3$ alkyl, —F, —Cl, —Br, —OH, —C≡N, —CF$_3$, C$_1$–C$_3$ alkoxy, and —NR$_{1-a}$R$_{1-b}$ where R$_{1-a}$ and R$_{1-b}$ —H or C$_1$–C$_4$ alkyl,
where R$_2$ is —H;
where R$_3$ is —H;
where R$_N$ is:
R$_{N-1}$—X$_N$— where X$_N$ is:
—CO—,
where R$_{N-1}$ is phenyl, substituted with one, two or three of the following substituents which can be the same or different and are C$_1$–C$_4$ alkyl, optionally substituted with one or two substituents selected from the group consisting of C$_1$–C$_3$ alkyl, —F, —Cl, —Br, —I, —OH, —SH, —C≡N, —CF$_3$, C$_1$–C$_3$ alkoxy, and NR$_{1-a}$R$_{1-b}$, —OH, —NO$_2$, —F, —Cl, —Br, or —I, —CO—OH, —C≡N, —(CH$_2$)$_{0-4}$—CO—NR$_{N-2}$ R$_{N-3}$, —(CH$_2$)$_{0-4}$—SO$_2$—NR$_{N-2}$R$_{N-3}$, —(CH$_2$)$_{0-4}$—SO—(C$_1$–C$_6$ alkyl), —(CH$_2$)$_{0-4}$—SO$_2$—(C$_1$–C$_6$ alkyl), —(CH$_2$)$_{0-4}$—SO$_2$—(C$_3$–C$_7$ cycloalkyl), —(CH$_2$)$_{0-4}$—O—(C$_1$–C$_6$ alkyl optionally substituted with one, two, three, four, or five —F), C$_3$–C$_7$ cycloalkyl, or —(CH$_2$)$_{0-4}$—C$_3$–C$_7$ cycloalkyl, where R$_{N-2}$ and R$_{N-3}$ are the same or different and are selected from the group consisting of H, and —C$_1$–C$_6$ alkyl optionally substituted with one substituent selected from —OH, and —NH$_2$, —C$_1$–C$_6$ alkyl optionally substituted with one to three —F, —Cl, —Br, or —I, —C$_3$–C$_7$ cycloalkyl, —(C$_1$–C$_2$alkyl)-(C$_3$–C$_7$ cycloalkyl), and —(C$_1$–C$_4$ alkyl)-O—(C$_1$–C$_3$ alkyl);
where R$_4$ is:
—C$_1$–C$_8$ alkyl,
—(CH$_2$)$_{0-3}$—(C$_3$–C$_7$) cycloalkyl,
—(CR$_{A-x}$R$_{A-y}$)$_{0-4}$—R$_{A-aryl}$,
-cyclopentyl or -cyclohexyl ring fused to R$_{A-aryl}$,
-cyclopentyl or -cyclohexyl ring fused to R$_{A-aryl}$,
—C=OR$_7$, where R$_7$ is
C$_1$–C$_6$ alkyl,
phenylalkyl,
cycloalkyl,
cycloalkylalkyl,
hydroxyalkyl,
alkoxyalkyl, or
haloalkyl,
where X is —N or —O, with the proviso that when X is O, R$_B$ is absent;
and when X is N, and
R$_B$ is:
H or —C$_1$–C$_6$ alkyl.

4. A substituted amine according to claim 3, where R$_4$ is: —(CR$_{A-x}$R$_{A-y}$)$_{0-4}$—R$_{A-aryl}$, -cyclopentyl or -cyclohexyl ring fused to R$_{A-aryl}$, or —C=OR$_7$, where
R$_{A-aryl}$ is phenyl, 1-naphthyl, or 2-naphthyl, substituted with one, two or three of the following substituents which can be the same or different and are C$_1$–C$_4$ alkyl, optionally substituted with one or two substituents selected from the group consisting of C$_1$–C$_3$ alkyl, —F, —Cl, —Br, —I, —OH, —SH, —C≡N, —CF$_3$, C$_1$–C$_3$ alkoxy, and —NR$_{1-a}$R$_{1-b}$, —OH, —NO$_2$, —F, —Cl, —Br, or —I, —CO—OH, —C≡N, —(CH$_2$)$_{0-4}$—CO—NR$_{N-2}$R$_{N-3}$, —(CH$_2$)$_{0-4}$—SO$_2$—NR$_{N-2}$R$_{N-3}$, —(CH$_2$)$_{0-4}$—SO—(C$_1$–C$_6$ alkyl), —(CH$_2$)$_{0-4}$—SO$_2$—(C$_1$–C$_6$ alkyl), —(CH$_2$)$_{0-4}$—SO$_2$—(C$_3$–C$_7$ cycloalkyl), —(CH$_2$)$_{0-4}$—O—(C$_1$–C$_6$ alkyl optionally substituted with one, two, three, four, or five —F), C$_3$–C$_7$ cycloalkyl, or —(CH$_2$)$_{0-4}$—C$_3$–C$_7$ cycloalkyl, where R$_{N-2}$ and R$_{N-3}$ are the same or different and are selected from the group consisting of H, and —C$_1$–C$_6$ alkyl optionally substituted with one substituent selected from —OH, and —NH$_2$, —C$_1$–C$_6$ alkyl optionally substituted with one to three —F, —Cl, —Br, or —I, —C$_3$–C$_7$ cycloalkyl, —(C$_1$–C$_2$alkyl)-(C$_3$–C$_7$ cycloalkyl), and —(C$_1$–C$_4$ alkyl)-O—(C$_1$–C$_3$ alkyl);
R$_7$ is C$_1$–C$_6$ alkyl, cycloalkyl, cycloalkylalkyl, alkoxyalkyl, or haloalkyl,
R$_{A-x}$ and R$_{A-y}$ are —H, C$_1$–C$_4$ alkyl optionally substituted with one or two —OH, C$_1$–C$_4$ alkoxy optionally substituted with one, two, or three —F, or phenyl;
where R$_B$ is H or C$_1$–C$_4$ alkyl.

5. A substituted amine according to claim 4, where R$_1$ is benzyl substituted with 2 halogens.

6. A substituted amine according to claim 5 where R$_1$ is benzyl substituted with 2 fluorines.

7. A substituted amine according to claim 6 where $R_1$ is 3,5-difluorobenzyl.

8. A substituted amine according to claim 5 where $R_N$ is —C(O)-phenyl, wherein the phenyl is substituted with one —CO—$NR_{N-2}R_{N-3}$.

9. A substituted amine according to claim 8 where $R_{N-2}$ and $R_{N-3}$ are independently H or $C_1$–$C_6$ alkyl.

10. A substituted amine according to claim 5 where $R_N$ is —C(O)-phenyl, wherein the phenyl is substituted with one methyl group and with one —CO—$NR_{N-2}R_{N-3}$.

11. A substituted amine according to claim 10 where $R_{N-2}$ and $R_{N-3}$ are independently H or $C_1$–$C_6$ alkyl.

12. A substituted amine according to either claim 8 or 10 where $R_A$ is:
—$(CR_{A-x}R_{A-y})_{0-4}$—$R_{A-aryl}$ where $R_{A-aryl}$ is phenyl, which is optionally substituted with one or two substituents selected from the group consisting of $C_1$–$C_3$ alkyl, —F, —Cl, —Br, —I, —OH, —SH, —C≡N, —$CF_3$, $C_1$–$C_3$ alkoxy, and —$NR_{1-a}R_{1-b}$; and wherein the phenyl is optionally fused to a cyclopentyl or cyclohexyl ring; and $R_{A-x}$ and $R_{A-y}$, if present, are both H.

13. A substituted amine according to claim 12 where $R_A$ is phenyl.

14. A substituted amine according to claim 12 where phenyl is mono-substituted at the 3-position or disubstituted at the 3,5-positions.

15. A substituted amine according to claim 12 where $R_A$ is: -cyclohexyl ring fused to a phenyl ring.

16. A substituted amine according to claim 13, where $R_B$ is H or $C_1$–$C_4$ alkyl.

17. A substituted amine according to claim 16 where $R_B$ is H.

18. A substituted amine according to claim 16 where $R_B$ is methyl.

19. A substituted amine according to claim 1, where X is oxygen and $R_B$ is absent.

20. A substituted amine according to claim 1 chosen from the group consisting of:
N-[1-(3,5-Difluoro-benzyl)-2-hydroxy-3-(N'-methyl-N'-phenyl-hydrazino)-propyl]-5-methyl-N',N'-dipropyl-isophthalamide,
N-{1-(3,5-Difluoro-benzyl)-2-hydroxy-3-[N'-methyl-N'-(4-methyl-pentanoyl)-hydrazino]-propyl}-5-methyl-N',N'-dipropyl-isophthalamide, and
N-[1-(3,5-Difluoro-benzyl)-2-hydroxy-3-phenoxyamino-propyl]-5-methyl-N',N'-dipropyl-isophthalamide.

21. A substituted amine according to claim 1 where the pharmaceutically acceptable salt is selected from the group consisting of salts of the following acids acetic, aspartic, benzenesulfonic, benzoic, bicarbonic, bisulfuric, bitartaric, butyric, calcium edetate, camsylic, carbonic, chlorobenzoic, citric, edetic, edisylic, estolic, esyl, esylic, formic, fumaric, gluceptic, gluconic, glutamic, glycollylarsanilic, hexamic, hexylresorcinoic, hydrabamic, hydrobromic, hydrochloric, hydroiodic, hydroxynaphthoic, isethionic, lactic, lactobionic, maleic, malic, malonic, mandelic, methanesulfonic, methylnitric, methylsulfuric, mucic, muconic, napsylic, nitric, oxalic, p-nitromethanesulfonic, pamoic, pantothenic, phosphoric, monohydrogen phosphoric, dihydrogen phosphoric, phthalic, polygalacturonic, propionic, salicyclic, stearic, succinic, sulfamic, sulfanilic, sulfonic, sulfuric, tannic, tartaric, teoclic and toluenesulfonic.

22. A composition comprising a compound of claim 1; and an inert diluent or edible carrier.

23. The composition of claim 22, where said carrier is an oil.

24. A composition comprising a compound of claim 1; and an binder, excipient, disintegrating agent, lubricant, or gildant.

25. A composition comprising a compound of claim 1, disposed in a cream, ointment, or patch.

26. A compound according to claim 9, wherein $R_N$ is of the formula

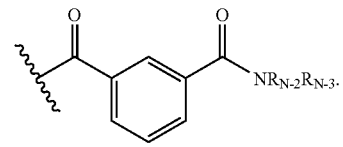

27. A compound according to claim 26, wherein $R_{N-2}$ and $R_{N-3}$ are both $C_3$ alkyl.

28. A compound according to claim 11, wherein $R_N$ is of the formula

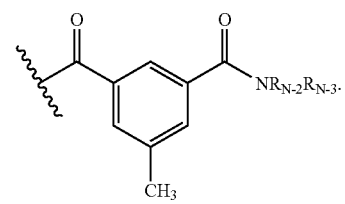

29. A compound according to claim 28, wherein $R_{N-2}$ and $R_{N-3}$ are both $C_3$ alkyl.

30. A compound according to claim 19, wherein
$R_1$ is benzyl, wherein the phenyl portion is optionally substituted with 1 or 2 groups that are F, Cl, $C_1$–$C_4$ alkoxy, $CF_3$, $C_1$–$C_4$ alkyl optionally substituted with one substituent selected from the group consisting of $C_1$–$C_3$ alkyl, —F, —Cl, —Br, —OH, —C≡N, —$CF_3$, $C_1$–$C_3$ alkoxy, and —$NR_{1-a}R_{1-b}$ where $R_{1-a}$ and $R_{1-b}$ —H or $C_1$–$C_4$ alkyl,
$R_2$ is —H;
$R_3$ is —H;
$R_N$ is $R_{N-1}$—$X_N$— where $X_N$ is —CO—, and $R_{N-1}$ is phenyl substituted with one, two or three of the following substituents which can be the same or different and are $C_1$–$C_4$ alkyl, —OH, —$NO_2$, —F, —Cl, —Br, or —I, —CO—OH, —C≡N, —$(CH_2)_{0-4}$—CO—$NR_{N-2}R_{N-3}$, where
$R_{N-2}$ and $R_{N-3}$ are the same or different and are selected from the group consisting of H, and —$C_1$–$C_6$ alkyl optionally substituted with one substituent selected from —OH, and —$NH_2$, —$C_1$–$C_6$ alkyl optionally substituted with one to three —F, —Cl, —Br, or —I, —$C_3$–$C_7$ cycloalkyl, —($C_1$–$C_2$ alkyl)-($C_3$-$C_7$ cycloalkyl), and —($C_1$–$C_4$ alkyl)-O—($C_1$–$C_3$ alkyl).

31. A compound according to claim 30, wherein
$R_A$ is —$(CR_{A-x}R_{A-y})_{0-4}$—$R_{A-aryl}$, or —C═$OR_7$, where $R_{A-aryl}$ is phenyl, 1-naphthyl, or 2-naphthyl, substituted with one, two or three of the following substituents which can be the same or different and are $C_1$–$C_4$ alkyl optionally substituted with one or two substituents selected from the group consisting of $C_1$–$C_3$ alkyl, —F, —Cl, —Br, —I, —OH, —SH, —C≡N, —$CF_3$, $C_1$–$C_3$ alkoxy, and $NR_{1-a}NR_{1-b}$, —OH, —$NO_2$, —F, —Cl, —Br, or —I, —CO—OH, —C≡N, —$(CH_2)_{0-4}$—CO—$NR_{N-2}R_{N-3}$, —$(CH_2)_{0-4}$—$SO_2$—$NR_{N-2}R_{N-3}$, —$(CH_2)_{0-4}$—SO—

($C_1$–$C_6$ alkyl), —$(CH_2)_{0-4}$—$SO_2$—($C_1$–$C_6$ alkyl), —$(CH_2)_{0-4}$—$SO_2$—($C_3$–$C_7$ cycloalkyl), —$(CH_2)_{0-4}$—O—($C_1$–$C_6$ alkyl optionally substituted with one, two, three, four, or five —F), $C_3$–$C_1$ cycloalkyl, or —$(CH_2)_{0-4}$—$C_3$–$C_7$ cycloalkyl, where $R_{N-2}$ and $R_{N-3}$ are the same or different and are selected from the group consisting of H, and —$C_1$–$C_6$ alkyl;

$R_7$ is $C_1$–$C_6$ alkyl;

$R_{A-x}$ and $R_{A-y}$ are —H, $C_1$–$C_4$ alkyl, or phenyl.

32. A compound according to claim 31, wherein $R_1$ is benzyl, wherein the phenyl portion is substituted with 1 or 2 groups that are F, Cl, $C_1$–$C_4$ alkoxy, $CF_3$, or $C_1$–$C_4$ alkyl;

$R_{A-aryl}$ is phenyl substituted with one or two of the following substituents $C_1$–$C_4$ alkyl, optionally substituted with one or two substituents selected from the group consisting of $C_1$–$C_3$ alkyl, —OH, —$NO_2$, —F, —Cl, —Br, or —I, —CO—OH, —C≡N, —$(CH_2)_{0-4}$—CO—$NR_{N-2}R_{N-3}$, and —$(CH_2)_{0-4}$—O—($C_1$–$C_6$ alkyl optionally substituted with one, two, three, four, or five —F, where $R_{N-2}$ and $R_{N-3}$ are the same or different and are selected from the group consisting of H, and —$C_1$–$C_6$ alkyl.

33. A substituted amine according to claim 32 where $R_N$ is —C(O)-phenyl, wherein the phenyl is substituted with one —CO—$NR_{N-2}R_{N-3}$.

34. A substituted amine according to claim 33 where $R_{N-2}$ and $R_{N-3}$ are independently H or $C_1$–$C_6$ alkyl.

35. A compound according to claim 34, wherein $R_{N-2}$ and $R_{N-3}$ are both $C_3$ alkyl.

36. A substituted amine according to claim 32 where $R_N$ is —C(O)-phenyl, wherein the phenyl is substituted with one methyl group and with one —CO—$NR_{N-2}R_{N-3}$.

37. A substituted amine according to claim 36 where $R_{N-2}$ and $R_{N-3}$ are independently H or $C_1$–$C_6$ alkyl.

38. A compound according to claim 37, wherein $R_{N-2}$ and $R_{N-3}$ are both $C_3$ alkyl.

39. A compound according to claim 4, wherein $R_7$ is $C_1$–$C_6$ alkyl;

$R_1$ is benzyl, wherein the phenyl portion is substituted with 1 or 2 groups that are F, Cl, $C_1$–$C_4$ alkoxy, $CF_3$, or $C_1$–$C_4$ alkyl; and $R_N$ is $R_{N-1}$—$X_N$— where XN is —CO—, and $R_{N-1}$ is phenyl substituted with one, two or three of the following substituents which can be the same or different and are $C_1$–$C_4$ alkyl, —OH, —$NO_2$, —F, —Cl, —Br, or —I, —CO—OH, —C≡N, —$(CH_2)_{0-4}$—CO—$NR_{N-2}$ $R_{N-3}$, where $R_{N-2}$ and $R_{N-3}$ are the same or different and are selected from the group consisting of H, and —$C_1$–$C_6$ alkyl optionally substituted with one substituent selected from —OH, and —$NH_2$, —$C_1$–$C_6$ alkyl optionally substituted with one to three —F, —Cl, —Br, or —I, —$C_3$–$C_7$ cycloalkyl, —($C_1$–$C_2$alkyl)-($C_3$–$C_7$ cycloalkyl), and —($C_1$–$C_4$ alkyl)-O—($C_1$–$C_3$ alkyl).

40. A compound according to claim 39, wherein $R_N$ is —C(O)-phenyl, wherein the phenyl is substituted with one —CO—$NR_{N-2}R_{N-3}$.

41. A substituted amine according to claim 40 where $R_{N-2}$ and $R_{N-3}$ are independently H or $C_1$–$C_6$ alkyl.

42. A compound according to claim 41, wherein $R_{N-2}$ and $R_{N-3}$ are both $C_3$ alkyl.

43. A substituted amine according to claim 39 where $R_N$ is —C(O)-phenyl, wherein the phenyl is substituted with one methyl group and with one —CO—$NR_{N-2}R_{N-3}$.

44. A substituted amine according to claim 43 where $R_{N-2}$ and $R_{N-3}$ are independently H or $C_1$–$C_6$ alkyl.

45. A compound according to claim 44, wherein $R_{N-2}$ and $R_{N-3}$ are both $C_3$ alkyl.

* * * * *